US011623058B2

(12) United States Patent
Shantha et al.

(10) Patent No.: US 11,623,058 B2
(45) Date of Patent: Apr. 11, 2023

(54) LOWER JAW THRUSTING, MANDIBULAR PROTRACTING, TONGUE HOLDING, UNIVERSAL OROPHARYNGEAL AIRWAY DEVICE

(71) Applicant: WEDGE THERAPEUTICS, LLC, Saint Paul, MN (US)

(72) Inventors: Totada R Shantha, Stone Mountain, GA (US); Robert Wieden, St. Paul, MN (US)

(73) Assignee: Wedge Therapeutics LLC, St. Paul, MN (US)

( * ) Notice: Subject to any disclaimer, the term of this patent is extended or adjusted under 35 U.S.C. 154(b) by 554 days.

(21) Appl. No.: 16/608,365

(22) PCT Filed: Feb. 12, 2018

(86) PCT No.: PCT/US2018/017812
§ 371 (c)(1),
(2) Date: Oct. 25, 2019

(87) PCT Pub. No.: WO2018/200063
PCT Pub. Date: Nov. 1, 2018

(65) Prior Publication Data
US 2021/0093818 A1    Apr. 1, 2021

Related U.S. Application Data

(60) Provisional application No. 62/490,658, filed on Apr. 27, 2017.

(51) Int. Cl.
*A61M 16/04*    (2006.01)

(52) U.S. Cl.
CPC .... *A61M 16/0493* (2014.02); *A61M 16/0495* (2014.02); *A61M 16/0497* (2013.01)

(58) Field of Classification Search
CPC ............ A61M 16/049; A61M 16/0493; A61M 16/0495
See application file for complete search history.

(56) References Cited

U.S. PATENT DOCUMENTS 3,930,507 A * 1/1976 Berman ................... A61B 1/24
                                              128/207.14
4,495,945 A * 1/1985 Liegner ............ A61M 16/0493
                                              128/200.26
(Continued)

*Primary Examiner* — LaToya M Louis
(74) *Attorney, Agent, or Firm* — Mark David Torche; Patwrite Law

(57) ABSTRACT

A lower jaw thrusting (LJT) mandibular protracting oral airway device including an elongate member with a distal end and a proximal end defining an air passageway channel. The elongate member includes a lip flange, a curved main body, and a bite block. The lip flange is located at the proximal end and has an outwardly projecting surface. The curved main body extends to the distal end. The bite block is disposed between the lip flange and the curved main body. The bite block includes an upper dorsal surface having a first bite portion for maxillary incisor teeth engagement and a lower ventral surface having a second bite portion for mandibular incisor teeth engagement. The bite block includes a mandibular flange projecting downwards from the lower ventral surface located distal to the second bite portion for mandibular incisor teeth engagement and proximal to the first bite portion for maxillary incisor engagement.

19 Claims, 37 Drawing Sheets

(56) References Cited

U.S. PATENT DOCUMENTS

| | | | | |
|---|---|---|---|---|
| 4,553,540 | A * | 11/1985 | Straith | A61M 16/0488 128/200.26 |
| 4,848,331 | A * | 7/1989 | Northway-Meyer | A61M 16/0495 128/200.26 |
| 4,919,126 | A * | 4/1990 | Baildon | A61M 16/0493 128/207.14 |
| 5,590,643 | A * | 1/1997 | Flam | A61M 16/0495 128/200.26 |
| 7,328,698 | B2 * | 2/2008 | Scarberry | A61M 16/0436 128/207.15 |
| 7,658,191 | B2 * | 2/2010 | Takuma | A61M 16/0495 128/207.14 |
| 7,975,695 | B2 * | 7/2011 | Munn | A61M 16/0488 128/207.14 |
| 8,783,261 | B2 * | 7/2014 | Thornton | A61F 5/566 128/848 |
| 10,258,319 | B2 * | 4/2019 | Arden | A61M 16/1005 |
| 2003/0000534 | A1 * | 1/2003 | Alfery | A61M 16/0409 128/207.14 |
| 2008/0078402 | A1 * | 4/2008 | Mongeon | A61M 16/0436 128/207.15 |
| 2010/0132700 | A1 * | 6/2010 | Filipi | A61B 1/00154 128/200.26 |
| 2010/0199998 | A1 * | 8/2010 | Matioc | A61M 16/0488 128/207.14 |
| 2012/0048278 | A1 * | 3/2012 | Yasick | A61F 5/566 128/848 |
| 2012/0234331 | A1 * | 9/2012 | Shantha | A61F 5/566 128/848 |
| 2014/0007868 | A1 * | 1/2014 | Eaton | A61M 16/0495 128/200.26 |
| 2014/0373849 | A1 * | 12/2014 | Akihiro | A61M 16/0493 128/207.14 |
| 2016/0022129 | A1 * | 1/2016 | Colman | A61B 1/24 600/543 |
| 2017/0000641 | A1 * | 1/2017 | Arden | A61M 16/0493 |
| 2017/0266401 | A1 * | 9/2017 | Arden | A61M 16/049 |

\* cited by examiner

LOWER JAW THRUSTING, MANDIBULAR PROTRACTING, TONGUE HOLDING, UNIVERSAL OROPHARYNGEAL AIRWAY DEVICE

RELATED APPLICATION

The present application claims the benefit of U.S. Provisional Application No. 62/490,658 entitled MANDIBULAR PROTRACTING, JAW THRUSTING ORAL AIRWAY DEVICE, filed Apr. 27, 2017, said application being hereby incorporated herein by reference in its entirety.

TECHNICAL FIELD

This disclosure relates to oropharyngeal airway devices for medical use on persons under anesthesia, in unconscious or semi-conscious states, to maintain an open airway. Such devices can be used for any number of medical conditions, fiberoptic procedures and indications to prevent the movement of the tongue and the jaw from blocking air passages, including during cardiopulmonary resuscitation (CPR). Specifically, embodiments disclosed relate to lower jaw thrusting (LJT), mandibular protracting, tongue root pulling forward, oral airway devices.

Devices sometimes referred to as "oropharyngeal airway devices", "oropharyngeal airways", "oral airways", "oral airway devices", and similar devices will generally be referred to broadly throughout this disclosure using the generic term "oral airway device".

SUMMARY

Embodiments relate to an LJT mandibular protracting oral airway device for protracting the lower jaw, for maintaining an oropharyngeal air passage for spontaneously ventilating patients. The LJT mandibular protracting oral airway device is able to press and hold a patient's tongue against the floor of the patient's mouth with a broad ventral surface to provide an unobstructed oropharyngeal air passage. An oropharyngeal air passage is maintained for patients: undergoing sedation for surgical, endoscopic, bronchoscopic, anesthesia related ventilation; during CPR; experiencing a coma; or who are unable to maintain an airway due to any number of afflictions. Afflictions can include those occurring during induction and emerging from anesthesia and fiber optic intubation procedures. Embodiments are designed to provide an LJT mandibular protracting oral airway device for ventilating with a mask, Ambu bag, or mouth-to-mouth resuscitation during various emergency conditions.

More precisely, embodiments are directed to an LJT mandibular protracting oral airway device configured for placement within a mouth between the tongue and palate of a patient. The device creates a passageway between the mouth of a patient and the posterior pharyngeal wall without obstruction due to the movement of the tongue anteriorly with lower jaw movement. In some embodiments, ridges provided on the ventral surface of the LJT mandibular protracting oral airway device prevent easy slipping back of the tongue. The LJT mandibular protracting oral airway device can be used anywhere and everywhere to replace existing common airway devices, and keep patient airways open with the help of its jaw thrusting mechanism.

In general, delivery of artificial ventilation to an unconscious and apneic patient via a mask applied to the patient's face is the most "basic" of airway management. However, bag-valve mask ventilation is not always easy. Upper airway obstruction may be encountered at the level of the nares, soft palate, lips (when the mouth is closed), base of the tongue, tonsillar pillars, epiglottis, or vocal cord inlet. To generate and maintain upper airway patency during artificial breathing, performance of the "triple airway maneuver" is advocated. This includes: moving forward the mandible until the lower teeth are in front of the upper teeth (jaw thrust); lifting the chin and maximally tilting the head backwards (chin lift, head tilt); and maintaining the mouth in an open position. As originally described, these airway maneuvers were performed with the operator positioned behind and at the head of the patient and using two hands. Placement of both hands on the mask, however, necessitates a second operator to squeeze the bag, which may be impractical if performed routinely.

An anesthesiologist may be unable to advance and maintain the mandible forward an adequate distance when using only one hand to hold the jaw. This is particularly important because changes to the retropalatal cross-sectional area differ in response to a jaw thrust between obese and non-obese patients, whereas the retroglossal airway does not. Two-handed mask ventilation generally achieves greater tidal volume during pressure-controlled ventilation than one-handed mask ventilation in anesthetized, non-paralyzed patients with an oral airway device inserted. The need for an oral airway device that can facilitate triple airway maneuvers is recognized and addressed by this disclosure and the embodiments contained herein.

An oral airway device or Guedel-Berman pattern airway are medical devices used in anesthesia, when emerging from anesthesia, during sedation, during CPR and such. An oral airway device is used to maintain patency of an airway path from the mouth of a patient to the pharynx of the patient, then to laryngo and nasopharynx. Oral airway devices are universally made for use in mask ventilation, in unconscious patients, apneic patients, or semi-conscious patients, during CPR or after induction and emerging from anesthesia and many such lifesaving situations. The function of an oral airway device is to provide unobstructed air passage from mouth to naso-oro-laryngo pharynx leading to trachea, bronchial tree and to its final destination—lung alveoli for ventilation.

An oral airway device is a medical airway adjunct device used to open and maintain a patient's oropharyngeal airway passage. An oral airway device acts by preventing the tongue from moving posteroinferiorly towards the pharyngeal wall, and from covering the epiglottis, which could prevent the person from breathing by blocking the oropharynx air passage, which in turn will block the naso-laryngo-pharynx air passages. When a person becomes unconscious, the muscles in the jaw connected to tongue movement and to the tongue muscles become flaccid due to loss of tone. The loss of tone of the genioglossus muscle (prime tongue protruder muscle) results in tongue moving posteriorly and inferiorly with retraction of mandible, resulting in the tongue obstructing the oropharyngeal air passage.

An oral airway device is a simple device used millions of times (an estimated 350-400 million oral airway devices are used annually) every year all over the world to establish an unobstructed ventilator air passage of the mouth in unconscious or semi-conscious patients or during CPR and other emergency situations. The present disclosure and embodiments recognize that oral airway devices in use at present lack a mandibular protracting jaw thrusting effect that pulls the tongue with its protruder genioglossus muscle forward and prevents the blocking of the oropharynx airway and the collapse of the fauces. Further, the present disclosure and embodiments recognize the importance of keeping open the naso-oro-laryngo-pharynx air passages needed for the unobstructed entry of air into the laryngo-tracheobronchial air passages and lung alveoli during breathing or artificial ventilation by mask.

Some existing oral airway devices include: an oral part; a bite block, and a lip flange. The oral part can include an elongated, curved or C-shaped section of polymer tube or hollow body (Guedel) or two channels running on both sides (Berman) from the central vertical spur called the body that is inserted into the mouth of the user and over the tongue. A bite block is generally a straight section that includes a proximally oral part held between the incisor teeth, and the lip flange. A bite block prevents the patient from deforming or breaking the oral airway device accidentally using their teeth. The proximal end of the bite block is connected to a flat, mostly oval, lip flange placed outside the mouth that is open to external air. A lip flange keeps the oral airway device from entering the mouth and oropharynx and causing foreign body obstruction. Distally, the bite block is connected to the oral part (i.e. the body) of the oral airway device.

An effective oral airway device, once placed in the mouth, creates and opens an air passageway between the mouth and the posterior pharyngeal wall and palate. An effective oral airway device establishes a mouth and nose airway that opens to the laryngo-pharynx and lungs for proper ventilation. This disclosure and the embodiments contained herein recognize that commonly used Guedel and Berman airway devices do not meet all the requirements of an effective oral airway device.

On the other hand, a nasopharyngeal airway is similar to the oropharyngeal airway; a bit longer, except that it is extended through the nostril to create a passageway between the nose and the nasopharynx. It is soft and pliable, blindly inserted that results in inferior turbinate damage, and can cause bleeding which can be a problem in those using blood thinners, and bleeding disorders, hence an oral airway device is the device of choice to maintain the air passage open and for artificial mask ventilation in the above enumerated medical conditions.

An oral airway device is a device used in anesthesia to maintain patency of the path from the mouth of a patient to the oropharynx of the patient. Oral airway devices are also utilized in mask ventilation, during CPR or induction or emerging from anesthesia; to facilitate fiber-optic intubation of the trachea ("Seldinger" technique) with an endotracheal tube, endoscopic examination of air passages, lungs, esophagus, and gastrointestinal tract to diagnose and treat conditions as well as to maintain an open oral airway under any medical conditions, where patients are unable to maintain an open oral airway. An oral airway device splints open the incisor teeth providing a conduit between the fixed upper maxilla and lower movable mandible through which a filamentous fiber-optic device may be passed from the mouth and also opens the communication to the oropharynx air passage.

The basic design of conventional oral airway devices is modified from Guedel and Berman designs. The Guedel oral airway is a hollow hard plastic tube, and the Berman oral airway has channels running along the central rib. They are placed between the teeth, utilized as a bite block, and follow a natural curve to the tongue and posterior pharynx to pull the tongue forward to facilitate passage of air. These devices do not pull a patient's jaw forward. A patient's tongue can move back with the mobile lower jaw and obstruct the air passages, which is not uncommon in supine positions in patients who are unconscious or semi-conscious, with flaccidity of tongue muscles. This disclosure and the embodiments contained herein recognize and address the need for an oral airway device that will prevent this type of obstruction. Traditional oral airway devices contain no provisions to hold the protracted lower jaw.

Another condition results when the tongue falls back, not under sleep, but when a patient is unconscious or semiconscious, especially during surgery or other office-based procedures done under sedation or during deep sleep. With decreasing levels of consciousness and increased depth of sedation or anesthesia, the relaxed tongue is flaccid, tends to fall backward with the mandible into the throat and progressively obstructs airflow. If not addressed, this can result in complete airway obstruction with death from suffocation. The tongue falling back to obstruct the airway is akin to obstructive sleep apnea that happens during sleep in millions of people, that can be related to natural sleep, that can be compared to sedation and/or anesthesia/CPR patients under induced coma for any number of reasons.

"Chin lift" and "jaw thrust" pushing the lower jaw (See FIG. 1) at the angle of the mandible are two procedures commonly used in the medical field to maintain an open airway in an unconscious or sedated patient. This may be done before intubation, during anesthesia or emerging from anesthesia, during CPR and other unconscious states due to an endless list of medical conditions including drug overdose and excess alcohol intoxications.

To generate and maintain upper airway patency during artificial breathing, performance of the "triple airway maneuver" is advocated. This includes: advancing the mandible forward until the lower teeth are in front of the upper teeth (jaw thrust); lifting the chin and maximally tilting the head backwards (chin lift, head tilt); and maintaining the mouth in an open position.

As originally described, these airway maneuvers were performed with the operator positioned behind and at the head of the patient and using two hands. In 1958, Safar showed that lay personnel could open the airway by thrusting the jaw forwards and tilting the head backwards. Rescue organizations have slowly adopted this technique. This disclosure and the embodiments contained herein recognize and address the need for a device that will better facilitate this maneuver.

The treatment of acute respiratory failure is simple in principle. It involves restoration of gas exchange across the pulmonary membrane to the unobstructed oropharynx, naso and laryngo pharynx. For this treatment, one needs to have a change of air in the alveoli, and a change of blood in the pulmonary capillaries—the main theme of CPR. One maneuver is generally no good without the other. This is merely another way of saying that artificial respiration will not help a dead or dying man; it has been learned in the last few years that death is not easy to define: certainly, it is not synonymous with cardiac arrest. If an anoxic heart, beating too feebly to produce a perceptible pulse, can still drive a trickle of blood through the pulmonary circulation, and that blood can take part in gas exchange, the myocardium will feel the benefit a few seconds later, and rapid and complete recovery is then a possibility. For a change of air and a change of blood for resuscitation to be effective for proper gas exchange, the airway has to be maintained. This disclosure and the embodiments contained herein recognize and address the need for an oral airway device that works in any CPR event and maintains the airway in the unconscious. This disclosure and the embodiments contained herein recognize and address the need for an oral airway device that thrusts the jaw, prevents the tongue moving back on the pharyngeal wall, and thus keeps the airway open and a rescuer's hands free.

Anatomically, the tongue is attached in front to the mandible by the genioglossus muscle, superiorly to the palatine muscles attached to the bony palate, posteriorly to the styloid processes and its muscles, inferiorly to the hyoid bone through hyoglossus (See FIG. 1E). It is the mandible that plays a major role in protrusion and pulling of the tongue forwards away from the oropharynx airway, hence jaw thrusting to maintain the airway (See FIG. 1). During jaw thrust, the mouth is open (See FIG. 1B), the mandible or lower jaw is protracted by pulling away from the temporo-mandibular joint (See FIG. 1). The maneuver pulls the tongue forward with its muscular genioglossus muscle attachments (See FIG. 1E), so that it minimizes the obstruction of the airway. Jaw thrust not only occupies a significant amount of time for the health care provider, but can also result in physical discomfort including low back pain and fatigue when it is performed for an extended period of time. In general, proposed devices addressing these issues have not been practical to this point. This disclosure and the embodiments contained herein recognize and address the need for a new and simple oral airway device that provides relief to a care provider to keeps an airway open in a variety of life threatening airway obstruction health conditions.

There are certain situations in which moderate to heavy sedation or general anesthesia without endotracheal intubation (insertion of a tube into the trachea through the laryngeal inlet) is desired; for example, a "general anesthetic mask" on a patient for a surgical procedure of short duration. In this situation, it is frequently necessary for the anesthesiologist or anesthetist to use a conventional oral airway device along with a chin lift or jaw thrust to maintain an unobstructed airway. Jaw thrusting also aligns the oropharynx to the mouth air passage to ensure the fiber-optic scope is straight, without much bending. If it is a rigid scope, which was used before, now almost rarely performed, this maneuver is a must. It is important to note that this maneuver is done millions of times in the operating room as the patient is induced or emerging from anesthesia. This requires the anesthesiologist/caregivers to use one hand on the patient's jaw and on the mask at all times, thus limiting his or her mobility and occupies one person's time, completely preventing them from attending to other needed care or they have to ask for a second person to help. Prior art conventional oral airway devices act only on the tongue in holding it back, and not the mandible thrusting to open the airway. If not, the tongue can fall back and cause airway obstruction in spite of the use of an oral airway device. This disclosure and the embodiments contained herein recognize and address the need to free the hands of the caregiver and at the same time maintain the airway as the patient emerges from anesthesia and from other conditions and is unable to maintain the airway by thrusting and maintaining a protracted mandible in that position, and not allowing the mandible with the tongue to retract back till the airway is manually removed.

The basic design of an existing orthodox oral airway device (See FIGS. 1 and 1D) has a rigid oral main body including a C-shaped oral part. The C-shaped oral part extends from the posterior end of a bite block with a somewhat rigid bite block or mouthpiece. The mouthpiece is attached at the forward end to a flange at the anterior end of the bite block and oral part at the posterior part. An annular front lip flange comes out of the mouth and stays in contact with the lips. (See FIG. 1). This disclosure and the embodiments contained herein recognize and address the need for a bite block that is completely different than a "traditional oral airway".

Oral airway devices can have a hollow cavity enclosed (Guedel) or hollow ridges on the sides of central rib (Berman), made of hard plastic when placed in the mouth between the teeth as a bite block, and follows a natural curve to the posterior pharynx to pull the tongue forward and push the palate upwards to facilitate passage of air without obstruction. The jaw can still move back with a flaccid tongue and obstruct the airway. These rigid oral airway devices can induce gagging, vomiting, aspiration, laryngo spasm, damage to teeth (due to patient biting), and damage to lips. If a fitting rigid oral airway device is left in place for a prolonged period of time, sores can develop in the mouth and bleeding may occur. Improper sizing of these oral airways introduces problems as well. Given the rigid nature of oral airway devices, sizing must be done without error. A rigid oral airway device that is too large can close the glottis and cut off an air supply. A too small rigid oral airway device can cause tongue sores and swelling. Prior art oral airway devices include a hard-curved piece of plastic that is often poorly tolerated in conscious and semi-conscious patients. This disclosure and the embodiments contained herein recognize and address the need for a device in which the tongue is pulled forward with the jaw to reduce such complications.

Further, conventional oral airway devices which are used for fiber optic oral intubation and other fiber optic procedures do not protract the mandible, and still frequently require the jaw thrust maneuver and extension of the neck for optimal mask ventilation.

Another problem with existing oral airway devices is that they do not have a short straight channel, which allows manipulation of a fiber-optic intubating stylet. This type of manipulation can be done with an attached endotracheal tube or fiber optic scope which allows insertion through it. These types of devices are also unsuitable for use in an awake or mildly sedated patient because they are relatively large, and their rearward ends pass far into the throat and cause the patient to gag, cough, or even vomit as they are emerging from a semi-conscious state. This disclosure and the embodiments contained herein recognize and address these shortcomings.

Anesthesia practitioners are taught the "tricks of the trade" regarding how to ventilate patients after induction of general anesthesia. These include a variety of physical adjustments to the anesthetized patient such as mandibular protracting jaw thrusting movement with extension of the patient's neck. If the patient cannot be adequately ventilated after induction of general anesthesia, life-threatening problems may develop such as hypoxia, hypercarbia, cardiac arrhythmias and even death. This disclosure and the embodiments contained herein recognize these problems and accordingly, prevent these maneuvers during anesthesia and ventilation including during insertion of fiberoptic scopes.

After general anesthesia has been induced, one of the main impediments to adequately ventilating a patient with positive pressure ventilation, after placement of an oral airway device, is the relaxation of the soft tissue structures in the hypo-pharynx (oropharynx). These structures slope to collapse, consequently obstructing airflow. This inward collapsing occurs both front-to-back and side-to-side, thus greatly decreasing the size of the oral opening through which the anesthesia practitioner may ventilate the patient. Physical characteristics, such as obese patients, greatly increase the difficulty of mask ventilation. Accordingly, it is more difficult to extend the neck and thrust the jaw forwards to establish an easy ventilation airway. The oral airway devices currently available do not adequately address the growing problem of obesity in the population. This disclosure and the embodiments contained herein recognize and address the need for an oral airway device that prevents respiratory obstruction by preventing collapse of the pharyngeal tissues (fauces) and/or obstruction of the pharynx by the tongue by mandibular protracting jaw thrusting oral airway device and holding the tongue in position at the same time keeping the naso-pharyngeal airway open to deliver supplemental oxygen besides keeping oropharynx open leading to laryngo pharynx (See FIG. 1A).

Each of the following U.S. patent references discloses conventional oral airway devices or related features: U.S. Pat. No. 5,024,218 to Ovassapian et al; U.S. Pat. No. 4,338,930 to Williams; U.S. Pat. Nos. 4,067,331, 4,054,135, and 3,930,507 to Berman; U.S. Pat. No. 3,756,244 to Kinnear et. al., U.S. Pat. No. 4,848,331 to Northway-Meyer; U.S. Patent Publication No. 2003/0000534 to Alfery; U.S. Pat. No. 5,590,643 to Flam; U.S. Pat. No. 4,363,320 to Kossove; U.S. Pat. No. 4,919,126 to Baildon; U.S. Pat. No. 7,278,420 to Ganesh et al.; U.S. Pat. No. 8,413,658 to Williams; U.S. Pat. No. 7,171,962 to Bloem; U.S. Pat. No. 4,944,313 to Katz et al; U.S. Pat. No. 5,174,284 to Jackson; U.S. Pat. No. 7,913,687 to Munn; U.S. Pat. No. 8,485,194 to Guerra et al.; and U.S. Pat. No. 9,669,174 to Isenberg et al. Each of these U.S. patent references is hereby incorporated herein by reference. This disclosure and the embodiments contained herein recognize and address the fact that the oral airway devices described in these patent references do not make use of mandibular protracting jaw thrusting to maintain an oro-naso-pharyngeal-laryngeal airway for ventilation to supply needed oxygen.

This disclosure and the embodiments contained herein recognize and address the fact that the oral airway devices discussed in these patent references and others do not thrust the mandible forwards to prevent the tongue moving back, and keep the oropharynx open even with an existing oral airway in the mouth. This disclosure and the embodiments contained herein recognize and address the need for an oral airway device that prevents the jaw and tongue of a patient from falling back by pulling the root of the tongue away from the epiglottis and pharyngeal wall, making the oropharynx-fauces air passage wide open for the easy exchange of gases and prevents any chance of the tongue obstructing the oropharynx-naso-pharynx air passage.

In the USA, more than twenty million surgeries are performed on an outpatient basis and more than fifty million surgeries are performed under anesthesia in the operating room. Regional/local anesthesia and intravenous sedation are growing in popularity as the preferred sedation method. One of the reasons for the increase is that nurses having little or no specialized anesthesia training are administering intravenous sedation for a growing number of procedures. Contrasted to general anesthesia, patients can recover more quickly, experience less postoperative pain, and nausea and vomiting, and rapid discharge to their homes. This disclosure and the embodiments contained herein recognize and address the fact that as patients are sedated and spontaneously breathing, oral airway devices are needed that can be used to provide an intervention to prevent the lower jaw and the tongue to be held protracted without allowing them to move back till the oral airway is removed from the mouth of the awaking patient or by the caregiver.

At present, there are several options to manage the airway of sedated patients: oral endotracheal tubes (OETT); the laryngeal mask airway (LMA); and the cuffed oral pharyngeal airway (COPA) that require advanced training and connection of the device to some external form of supplemental oxygen or an anesthesia circuit, and are not available to the non-anesthesia trained nurse. They are poorly tolerated by patients unless deep sedation or general anesthesia is administered. This disclosure and the embodiments contained herein recognize and address the need for a LJT mandibular protracting oral airway device under anesthesia or otherwise.

Annular mouthpieces/bite blocks are known in the art to maintain the jaw open between the incisors teeth, and to prevent the biting of the tongue. These devices are used for endoscopic examination of the throat, and upper respiratory and gastrointestinal tracts and during electric shock therapy. Prior art mouthpieces and bite blocks are generally unsuitable for use in a moderately sedated or unconscious patient because they are relatively short and do not protract the mandible, nor a major expanse of the tongue.

Taking into consideration existing oral airway devices and contraptions described, this disclosure and the embodiments contained herein recognize and address the need for further improvements in oral airway devices used to protract the jaw and to hold the tongue in position and prevent it from falling back to the oropharynx so as to obstruct the air passage. Further, this disclosure and the embodiments contained herein recognize and address the need to facilitate a fiber-optic medical device to diagnose and treat the respiratory system, esophagus, and GI tract afflictions.

In view of the deficiencies of existing oral airway devices, this disclosure and the embodiments contained herein recognize and address the need for a new LJT mandibular protracting oral airway device that modifies the bite block of prior oral airway devices so that the new modified oral airway device can be used to thrust the jaw forwards and prevent the tongue falling back to cause obstruction in patients during anesthesia, emerging from anesthesia, under sedation, semi-conscious with spontaneous breathing, and with heart and CNS afflictions. Further, this disclosure and the embodiments contained herein recognize and address the need to facilitate introduction of devices for various fiber-optic procedures.

Mask ventilation is considered a "basic" skill for airway management practiced effectively by more than 400 million times all over the globe by medical care providers such as anesthesiologists, PA, EMT, CRNAs and host of other caregivers. The commonly labeled one-handed "EC-clamp" technique is most often used after induction of anesthesia with a two-handed jaw-thrust technique reserved for difficult cases. This is a technique for holding a mask on the face of a manually ventilated patient, in which the thumb and index finger hold the mask down over the nose and mouth of the patient, forming a "C" while the other three fingers of the hand grasp the patient's mandible, forming an "E" (EC-clamp). Many times, caregivers are busy using both hands and not free to attend and provide care to other needs of the unconscious or semi-conscious patients. This disclosure and the embodiments contained herein recognize and address the need for freeing one or both hands of a caregiver with a mask holder that uses a LJT mandibular protracting oral airway device to hold the protracted mask, without the need for mandibular protracting jaw thrusting maneuver, totally freeing both the hands of the caregiver.

Multiple studies have shown that the mandibular protracting jaw thrusting, is important to maintain a proper airway in all CPR and under anesthesia as well as other unconscious or semiconscious states. This disclosure and the embodiments contained herein recognize and address the need for a maneuver that frees the hands of a caregiver to ventilate and attend to other needs of an anesthetized and/or semi or unconscious or critically ill patient.

Research studies have been done on the efficacy of the loss of response to jaw thrust as a clinical test to assess adequate depth of anesthesia for insertion of the laryngeal mask. In one study, after induction of anesthesia with Propofol (infused using a syringe driver), the patients were randomly allocated to one of two groups. In one group, insertion of the laryngeal mask was attempted immediately after the loss of verbal contact and in the other group, after the loss of motor response to a jaw thrust. Conditions for insertion of the laryngeal mask were assessed. The mean dose of propofol required to obtain loss of verbal contact was 1.94 mg·kg−1 (SD 0.39, 95% confidence intervals (CI) 1.79-2.08 mg·kg−1) and that for the loss of response to jaw thrust was 2.55 mg·kg−1 (SD 0.46, 95% CI 2.38-2.72 mg·kg−1). When depth of anesthesia was assessed using jaw thrusting, it was always possible to insert the mask and the conditions were optimal in 87% (95% CI 72-95%) of patients. Neither coughing nor gagging occurred. In contrast, conditions were almost always less than optimal when insertion was attempted after the loss of verbal contact. Conditions were significantly better when jaw thrust was used as a clinical test compared with loss of verbal contact (p=0.001). No marked hemodynamics depression occurred in any patient. Thus, jaw thrust is deemed a reliable clinical test to assess the adequate depth of anesthesia. The present disclosure and the embodiments contained herein recognize and address the need for a LJT mandibular protracting oral airway device for uncomplicated insertion of the laryngeal mask after induction of anesthesia.

Detailed study findings support the notion that the anesthesiologist is unable to advance and maintain the mandible forward an adequate distance when using only one hand to hold the jaw. The present disclosure and the embodiments contained herein recognize and address the fact that changes to the retropalatal cross-sectional area differ in response to a jaw thrust between obese and non-obese patients using embodiments presently disclosed, whereas retroglossal airway devices in common use now do not.

The first oral (oropharyngeal) airway was introduced in the year 1933 by Guedel and later in 1966 by Berman and many others since then. The basic designs are still in use today and all conventional oral airway devices were modified from them. Unfortunately, with what is know today regarding anatomical physiology of the oropharyngeal airway, they are an old "hold over" from the past and continue to be an important overlooked device that does not adequately fulfill all the requirements to carry out the task to maintain the airway in unconscious/semi-conscious patients. This was evidenced by the studies by which showed that just using these common airways are not adequate to maintain the oropharynx airway, and it is important to protract the mandible forwards in adults to maintain the patent airway by using lower jaw thrust. This was further substantiated by various studies on the lower jaw thrust maneuverer such as placement of both hands on the mask. However, this necessitates a second operator to squeeze the bag, which may be impractical if performed routinely. The present disclosure and the embodiments contained herein recognize and address the need for a LJT mandibular protracting oral airway device that frees one hand to provide care without needing a second person with assistance of pressure-controlled ventilation freeing the operator to focus their attention on positioning of the oral airway, and the sealing of the mask.

No study has systematically compared ventilatory effectiveness between one-handed and two-handed mask-hold techniques. Both the maneuvers have been compared, and found that two-handed mask ventilation achieved greater tidal volume during pressure-controlled ventilation than one-handed mask ventilation in anesthetized, nonparalyzed patients with oropharyngeal airway inserted. The present disclosure and the embodiments contained herein recognize and address the need for a LJT mandibular protracting oral airway device that will free the use of one or two hands depending upon the situation.

The lower jaw thrusting maneuver to improve the oropharynx oral airway is further supported by recent studies from all over the world. The studies are increasing on the effect of lower jaw thrust and how it increases the oropharyngeal airway of all age groups.

One study fiber-optically examined the laryngeal aperture during direct laryngoscopy and demonstrated that, in some patients with difficult intubation, the Macintosh laryngoscope could not lift the epiglottis close to the posterior pharyngeal wall sufficiently and could not expand the collapse of the structures around the laryngeal aperture caused by general anesthesia and muscle relaxation. However, when a jaw thrust maneuver was applied to these patients, the epiglottis was lifted, soft tissues around the laryngeal aperture were expanded, and glottic exposure for fiberscopy, and for movement of air to the oropharynx and to the larynx was easily achieved. With the use of a fiberoptic stylet, therefore, a jaw thrust maneuver applied by grasping the jaw with the operator's non-dominant hand, instead of the laryngoscope, can lift the epiglottis and expand the laryngeal aperture tissues. This procedure can facilitate viewing the glottis though the fiberoptic stylet and passing an endotracheal tube of the standard size through the glottis even when a laryngoscope cannot lift the epiglottis sufficiently. The present disclosure and the embodiments contained herein recognize the same phenomenon during endotracheal intubation under video visual control in some patients with difficult intubation.

One study reported that the two-handed jaw thrust facilitated lightwand-guided intubation, and reduced the incidence and severity of postoperative sore throat compared to the single-handed chin lift. They reported that the jaw-thrust increased tidal volume, minute ventilation, and peak tidal inspiratory and expiratory flows significantly in all infants studied (mean±SEM age=8±2 months). CPAP increased peak tidal inspiratory and expiratory flows by more than twice the coefficient of variation of baseline measurements. In view of this, the present disclosure and the embodiments contained herein recognize and address the need for a LJT mandibular protracting oral airway device.

Another study evaluated the effects of three airway manipulation maneuvers: (a) conventional (single-handed chin lift); (b) backward, upward and right-sided pressure (BURP) maneuver; and (c) modified jaw thrust maneuver (two-handed aided by an assistant) on laryngeal view and intubation time using the Clarus Video System in patients undergoing general anesthesia with orotracheal intubation showed that the modified jaw thrust improved the laryngeal view, and the BURP maneuver worsened the laryngeal view, using the Clarus Video System. Therefore, intubation time with the modified jaw thrust maneuver was shorter than with either the conventional or the BURP maneuver. Their study showed that modified jaw thrust pulled the epiglottis and the posterior laryngeal tissue in a more upward direction, in contrast to the BURP maneuver. Although overall success rates were high, the time to intubation was significantly faster with the modified jaw thrust maneuver. The present disclosure and embodiments can provide this and accordingly, recognize and address the need for a LJT mandibular protracting oral airway device.

Literally every patient after induction of anesthesia and waking up from anesthesia is provided with a jaw thrust as they wake up to prevent the tongue falling back and obstructing the airway. Almost every patient intubated is provided with an oral airway device to prevent biting of the soft endotracheal tube and tongue. Both of these procedures involve protracting the mandible or lower jaw by pulling it forward relative to the maxilla or upper jaw. This jaw thrusting is also done during all CPR procedures and for those who are choking (See FIG. 1, 1A-D).

The present disclosure and the embodiments contained herein recognize and address the need for proper oral airway device usage, with a protracted mandible (lower jaw thrust forwards) using the offset of the maxillary teeth and mandibular teeth as a fulcrum. Spontaneous ventilation is maintained and can save lives before, during, and after surgery procedure under anesthesia, sedation, in critical care and CPR. Further, the present disclosure and the embodiments contained herein recognize and address the fact that in current Guedel and Berman oral airway devices, there are no proportional dimensional standards being employed to the length change in the bite block and the radius of the C curve back body in relation to how it would impact the oropharyngeal area. The present disclosure and the embodiments contained herein recognize and address this with an oral airway device that overcomes the shortcomings of the historically designed, disproportionately-sized oral airways and that incorporates new design elements that can advance how airway management is currently being conducted across the globe. The present disclosure and the embodiments contained herein introduce multiple versions of a LJT and tongue restraining oral airway device that can increase the oropharynx airway with uniform dimensional standards.

In previous existing oral airway devices, there are no provisions made to connect the oral airway devices to a mechanical ventilator to further free the hands of the caregiver. The present disclosure and embodiments can provide this and accordingly, recognize and address the need for a device where the lower jaw-thrust mechanism can be incorporated in other existing oral airway devices, such as Ovassapian, Williams, etc., for better management of an airway.

In view of this, the present disclosure and the embodiments contained herein recognize and address the need for a LJT mandibular protracting oral airway device design that establishes an easy ventilation airway for the overweight or obese patient population. Using the present disclosure and the embodiments contained herein will allow ease of breathing. This includes obese patients who have breathing problems, and in patients with macroglossia. This patient population increases the difficulty of mask ventilation since they tend to have larger, thicker necks and tongues, along with more redundant soft tissue in the oropharyngeal area. Therefore, it is more difficult to extend the neck and thrust the jaw forwards to establish an easy ventilation airway since surrounding structures are being forced to collapse due to an oversized tongue, narrow fauces, fatty tissue and gravity.

In view of this, the present disclosure and the embodiments contained herein recognize and address the need for a LJT mandibular protracting oral airway device that incorporates uniformity, standardization, and a jaw-thrust mechanism that holds the lower jaw forwards pulls the genioglossus muscle of the tongue and prevents it from falling back to limit the obstruction of the oropharyngeal airway. In combination, present disclosure and the embodiments of oral airway devices referenced herein lift the Hyoglossus muscle with the root of the tongue, and the epiglottis, opening the pharyngeal airway. The present disclosure and the embodiments of oral airway devices referenced herein improve the functionality to open the oropharyngeal airway, ventilate through the naso-pharyngeal airway, open the fauces and increases a practitioner's ability to provide better ventilation directed to the larynx and respiratory passages of the lungs, and at the same time, provide for improved patient care.

In an experimental model, which bypassed the retropalatal airway with the use of an OPA, the ability to decrease upper airway resistance would have been totally dependent on changes in the retroglossal airway, moving the epiglottis away from the posterior pharyngeal wall, and the diameter of the vocal cord inlet. Relief of obstruction at these sites has been demonstrated with use of mandibular advancement with or without the application of continuous positive end-expiratory pressure in various studies. Because positive end-expiratory pressure was not used, maintenance of upper airway patency was totally dependent on simple mechanical interventions. In view of this, the present disclosure and the embodiments contained herein recognize and address the need for a LJT mandibular protracting oral airway device that automatically provides jaw lift and thrust automatically.

Oropharyngeal airways are generally indicated only in unconscious people, because of the likelihood that the device would stimulate a gag reflex in conscious or semi-conscious persons. This could result in vomit and potentially lead to an obstructed airway. Nasopharyngeal airways are mostly used instead as they do not stimulate a gag reflex. In general, oral airway devices need to be sized and inserted correctly to maximize effectiveness and minimize possible complications, such as oral trauma, otherwise the following problems can result: If the person has a gag reflex, they may vomit; When a device is too large, it can close the glottis and thus close the airway; Improper sizing can cause bleeding in the airway. The device is removed when the person regains swallow reflex and can protect their own airway, or it is substituted for an advanced airway. It is removed simply by pulling on it without rotation.

Presently used oral airway devices (Guedel and Berman) have been examined. It was discovered that the buccal bite block and mouth part of these do not match with size variation proportions. In general, the bite block and mouth pieces curve and length for these devices do not match. The present disclosure and the embodiments contained herein recognize and address the need for Guedel and Berman and other types of oral airway devices to have a proportionate bite block length and breadth in relation to the mouth piece, and in relation to overall oral airway device sizes. Further, the present disclosure and the embodiments contained herein recognize and address the need for standardization of oral airway device sizes.

When using prior art oral airway devices, the root of the tongue can move back. The present disclosure and the embodiments contained herein recognize and address the need for an oral airway device having a projection at the distal end of the ventral plate that will prevent the movement of the root of the tongue from moving backwards on the epiglottis and the posterior wall of the pharynx.

Embodiments can include an LJT mandibular protracting oral airway device including an elongate member having a distal end and a proximal end defining an air passageway channel therebetween. The elongate member is sized for insertion in a patient's mouth such that the distal end is disposed adjacent the patient's tongue root while the proximal end remains disposed outside the patient mouth. The elongate member includes a lip flange, a curved main body and a bite block. The lip flange is located at the proximal end of the elongate member having an outwardly projecting surface configured to overlie lips of the patient. The curved main body extends to the distal end of the elongate member. The curved main body provides downward and inferior tongue pressure resistive to backward tongue movement. The bite block is disposed between the lip flange and the curved main body. The bite block includes an upper dorsal surface having a first bite portion for maxillary incisor teeth engagement and a lower ventral surface having a second bite portion for mandibular incisor teeth engagement. The bite block includes a mandibular flange projecting downwardly from the lower ventral surface. The mandibular flange is located distal to the second bite portion for mandibular incisor teeth engagement and proximal to the first bite portion for maxillary incisor engagement.

Embodiments can include an LJT mandibular protracting oral airway device wherein the upper dorsal surface provides a depression surface at the first bite portion and the lower ventral surface provides a depression surface at the second bite portion.

Embodiments can include an LJT mandibular protracting oral airway device wherein the bite block includes a maxillary flange upwardly projecting from the upper dorsal surface, the maxillary flange located distal to the mandibular flange along the elongate member.

Embodiments can include an LJT mandibular protracting oral airway device wherein the air passageway channel of the elongate member is generally substantially acruate and tubular in shape.

Embodiments can include an LJT mandibular protracting oral airway device wherein the air passageway channel of the elongate member is C-shaped and defines openings along the curved main body.

Embodiments can include an LJT mandibular protracting oral airway device wherein the upper dorsal surface and lower ventral surface of the bite block comprise resilient material.

Embodiments can include an LJT mandibular protracting oral airway device wherein the curved main body includes a round nub near the distal end of the elongate body that is configured to engage the patient's tongue root in front of the epiglottis thereby restricting distal backward movement of the tongue root.

Embodiments can include an LJT mandibular protracting oral airway device wherein the curved main body includes a pair of lateral extensions extending along the sides of the ventral plate that restrict tongue movement.

Embodiments can include an LJT mandibular protracting oral airway device wherein the curved main body includes a ventral plate of oval or rectangular shape with expanded transverse ridges configured to engage the patient's tongue thereby restricting distal and side-to-side tongue movement.

Embodiments can include an LJT mandibular protracting oral airway device wherein the lip flange is comprised of an upper lip flange and a lower lip flange. In some embodiments, the lower lip flange can extend in a tear drop shape on both sides all the way to the base of the ventral bite block surface, just above the lower lip flange junction at the lower end of the bite block.

Embodiments can include an LJT mandibular protracting oral airway device wherein the mandibular flange is located 0.25 to 1 inch proximal from the upper lip flange as to extend the mandibular jaw. In some embodiments the mandibular flange is located 0.25 to 0.75 inch proximal from the upper lip flange. In some embodiments, the mandibular flange is located at the same level from the upper lip flange.

Embodiments can include an LJT mandibular protracting oral airway device wherein the curved main body includes a dorsolateral plate containing a plurality of holes.

Embodiments can include an LJT mandibular protracting oral airway device wherein the bite block contains a second mandibular flange projecting outwardly from the lower ventral surface, the mandibular flange and the second mandibular flange forming a pocket surrounding the second portion for mandibular incisor teeth engagement.

Embodiments can include an LJT mandibular protracting oral airway device wherein the bite block contains a pair of maxillary flanges outwardly projecting from the upper dorsal surface, the pair of maxillary flanges forming a pocket surrounding the first portion for maxillary incisor teeth engagement.

Embodiments can include an LJT mandibular protracting oral airway device further including an extension attachment that accommodates a ventilating opening in the lip flange surrounded by an external opening in the oral airway device for connecting to a mechanical ventilator or an Ambu bag.

Embodiments can include an LJT mandibular protracting oral airway device wherein the air passageway channel is generally oval or rectangular in cross section.

Embodiments can include an LJT mandibular protracting oral airway device wherein the elongate member is semi-rigid distal to the lip flange and resistant to collapse.

Embodiments can include an LJT mandibular protracting oral airway device wherein the mandibular flange permits proximally forward pulling that enhances thrusting of the lower jaw, along with the root of the tongue. Once the lower jaw is thrust, the mandibular flange won't allow the mandible and the attached tongue and the genioglossus muscle attached to the genoid turbercle of the mandible to move backwards.

Embodiments can include an LJT mandibular protracting oral airway device wherein the lip flange includes at least one hole adapted for nasal oxygen delivery or delivery tubing tethered to a placement hook.

Embodiments include an LJT mandibular protracting oral airway device wherein the curved main body has a short length, large diameter configuration that accommodates fiber optic examination or intubation.

Embodiments include an LJT mandibular protracting oral airway device wherein the lip flange incorporates liquid transfer tubing of different lengths running above or below the bite block, that can be attached to a three-way stopcock outside the patient's mouth, to transport therapeutic agents or mouth rinsing fluids under or above the patient's tongue.

Embodiments can include an LJT mandibular protracting oral airway device including an elongate member having a distal end and a proximal end defining an air passageway channel therebetween. The elongate member is sized for insertion in a patient's mouth such that the distal end is disposed adjacent the patient's tongue root while the proximal end remains disposed outside the patient mouth. The elongate member includes a lip flange, a curved main body and a bite block. The lip flange can be located at the proximal end of the elongate member and include an upper lip flange and a lower lip flange. The upper lip flange and lower lip flange can each include a vertically-disposed member generally projecting outwardly relative to a central opening of the air passageway channel. The upper lip flange has a first distal surface that is generally vertically-disposed for proximal placement relative to an upper lip of the patient's mouth. The lower lip flange has a second distal surface that is generally vertically disposed for proximal placement relative to a lower lip of the patient's mouth. The first distal surface of the upper lip flange is located distal to the second distal surface of the lower lip flange. The curved main body extends to the distal end of the elongate member. The curved main body provides downward and inferior tongue pressure resistive to backward tongue movement. The bite block is disposed between the lip flange and the curved main body and includes an upper dorsal surface for maxillary incisor teeth engagement and a lower ventral surface for mandibular incisor teeth engagement. The bite block includes a mandibular flange projecting downwardly from the lower ventral surface. The mandibular flange having a vertical surface located proximal to the first distal surface of the upper lip flange.

Embodiments can include a LJT mandibular protracting oral airway device having a rigid main body with or without a soft, not stiff, non-irritating end with a non-collapsible mouthpiece portion at the forward end. The mouthpiece portion acts as a bite block where the incisor teeth come in contact and hold the mandible in jaw thrust position using a front flange. The bite portion extends a short distance rearwardly, which is generally oval shaped in the transverse cross section and has an annular rear flange at the rear end thereof. The bottom wall of the bite portion extends to the rear from the rear flange and curves downwardly in a flat, generally C-shaped tongue retractor oral portion. A resilient annular sleeve is mounted between the front and rear flanges and encircles the bite portion. The bite block that comes in contact with the maxillary incisor teeth has a flange that prevents the movement of the maxillary teeth forwards or backwards. When properly positioned in the mouth of a patient, the upper and lower teeth are retained in their incisor teeth receptacles, the upper jaw retracted back, the mandible thrust forward thus pulling the root of the tongue away from the oropharyngeal opening thus prevent the obstruction during sleep and/or under unconscious state.

In various embodiments, after the LJT mandibular protracting oral airway device has been inserted in the mouth between the upper and lower jaws, there is no need for continuous manual chin lift or jaw thrust by anesthesiologists, anesthetists or caregivers attending and providing CPR. The mouthpiece portion functions as a bite block and the oval-shaped or rectangular opening through which the bite portion functions as an intubation guide to facilitate insertion of endoscopes and related medical instruments, such as a fiber-optic scope, intubating stylet with an attached endotracheal tube and suctioning the oropharynx secretions and stomach regurgitate to prevent aspiration.

Embodiments can include a LJT mandibular protracting oral airway device which maintains the airway of an unconscious (under anesthesia) or sedated patient who is unable maintain their own airway due to any number of health afflictions.

Embodiments can include a LJT mandibular protracting oral airway device which protracts the mandible or lower jaw relative to the fixed maxilla or upper jaw and pulls the tongue forward with its genioglossus muscle attachment at its root.

Embodiments can include a LJT mandibular protracting oral airway device which eliminates the need for an anesthesiologist/caregiver to perform continuous manual chin lift or jaw thrust, thus frees the hands of the anesthesiologist/anesthetist/caregiver for other tasks.

Embodiments can include a LJT mandibular protracting oral airway device which maintains the airway of an unconscious or heavily sedated patient open to possible spontaneous or controlled ventilation, while allowing relatively rapid, unencumbered oral fiber-optic intubation using a fiber-optic stylet in patients who cannot be intubated using traditional direct laryngoscopy.

Embodiments can include a LJT mandibular protracting oral airway device which maintains the airway of a patient with a small and compact oral airway device than can be easily tolerated by an awake or mildly sedated or semiconscious spontaneously breathing patient or sleeping person and to reduce the possibility of gagging, coughing, or vomiting during its use.

Embodiments can include a LJT mandibular protracting oral airway device which functions as a bite block for endoscopic examination of the upper gastrointestinal and respiratory tracts and also functions to maintain the straight airway passage of a spontaneously breathing, sedated or unconscious patient during introduction of these scopes and procedures.

Embodiments can include a LJT mandibular protracting oral airway device with entry openings on both sides of the flange to insert a delivery connector, that is further linked to proximal part of the connector on the lip flange when a Guedel type (center opening) airway is used to facilitate the fiber optic and endotracheal tubes introduction. Such a device can be used: with a suction catheter to clear a patient's mouth; for a mouth irrigation system; to deliver therapeutic agents to a patient's oral cavity to treat mouth afflictions and such; or to provide oxygen through a nasal cannula inserted into the openings secured by a hook on the lip flange.

Embodiments can include a LJT mandibular protracting oral airway device with an entry opening on the flange to insert a nasogastric tube to deliver fluids, therapeutic agents, and nutrition to the patients who are unconscious and need to be fed.

Embodiments can include a LJT mandibular protracting oral airway device which is simple in construction, economical to manufacture, made up of non-reacting hypoallergic material, is safe and reliable to use and can be disposable or sterilized for reuse.

Embodiments can include a LJT mandibular protracting oral airway device with a tear drop plate extension placed ventrally lower to the end of the curved part of the airway which provides enhanced support to the tongue laterally, thus increasing the side to side dimensions of oral airway opening. This is can be especially useful in patients with a large tongue.

Embodiments can include a LJT mandibular protracting oral airway device to construct an oral airway device from medical grade materials and that have the necessary rigidity, or are reinforced, so as to prevent a collapse when the oral airway device is bitten down upon by a patient.

Embodiments can include a LJT mandibular protracting oral airway device to construct a latex free oral airway.

Embodiments can include a LJT mandibular protracting oral airway device in a variety of sizes ranging from neonatal to large adult sizes and that the airways preferably are color coded so as to indicate size upon quick visual observation.

Embodiments can include a LJT mandibular protracting oral airway device that incorporates soft pliable non-collapsible material to the distal third of the oral piece to prevent gagging, coughing, and vomiting as the patient is awake or waking up due to the rigid oral airway device end coming in contact with the epiglottis and posterior third of the tongue.

Embodiments can include a LJT mandibular protracting oral airway device having a breathing and carbon dioxide monitor attached to the front flange collar running along inside the oral airway device body, which will monitor the rate of breathing and the carbon dioxide content, and if there is snoring sound and/or arrest of breathing will make noise to warn the user or caregiver.

Embodiments can include a LJT mandibular protracting oral airway device incorporate gas sampling or a delivery cannula to monitor breathing especially during endoscopy procedures.

Embodiments can include a LJT mandibular protracting oral airway device maintain a patent airway, to provide for oxygen supplementation and end tidal air $CO_2$ (ETC02) monitoring in spontaneously ventilating, sedated patients as well as to allow the placement and use of scopes in various medical procedures.

Embodiments can include a LJT mandibular protracting oral airway device which can be used by non-anesthesia trained medical providers. In another aspect, embodiments can include a LJT mandibular protracting oral airway device having a main airway lumen having a straight passageway allowing accommodation of endoscopes and bronchoscopes with lower jaw thrust forwards Embodiments can include a mandibular flange, as disclosed herein, of the LJT mandibular protracting oral airway device on other popular oral airway devices such as Guedel and Berman, Ovassapian, Williams oral airway devices and such, to provide enhanced oral airway devices by introducing a mandibular protracting jaw thrusting feature described herein.

Embodiments are contemplated in which an oral airway device is provided with a mandibular protracting jaw thrusting flange on the bite block with a maxillary fulcrum nub instead of a flange.

In various embodiments, once the oral airway device is inserted, a special connecter is placed on the proximal opening of the oral airway device and mechanical ventilator operation tubing is connected, thus freeing both hands of a caregiver. Tidal volume can be increased to compensate for leakage. If needed, the jaw can be held by a jaw holder strap to prevent any air leak. The oral airway device can also be connected to the Ambu bag away from the face with tubing, to be ventilated by another person if needed. Once a patient's other needs are met, the caregiver can attend to malignance of the airway by endotracheal tube or mask ventilation as needed.

Embodiments can include a LJT mandibular protracting oral airway device having measurements of a bite block, C-curve, and other dimensions that correlate with the changes in the dimensional length size.

The above summary is not intended to describe each illustrated embodiment or every implementation of the subject matter hereof. The figures and the detailed description that follow more particularly exemplify various embodiments.

BRIEF DESCRIPTION OF THE FIGURES

Subject matter hereof may be more completely understood in consideration of the following detailed description of various embodiments in connection with the accompanying figures, in which.

Figure 1:
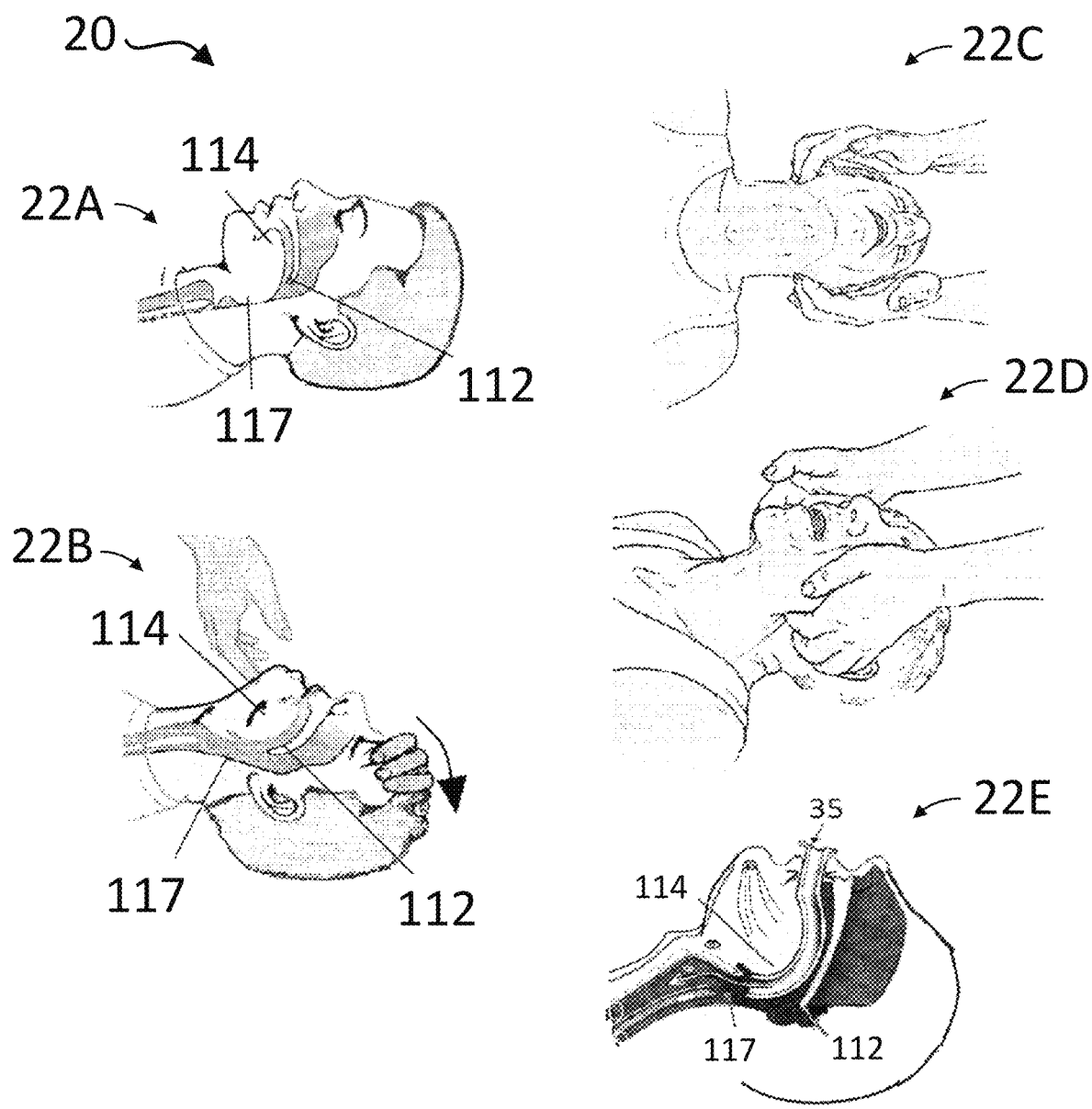
FIG. 1 is a diagram of existing mandibular protracting jaw thrusting manual procedures and devices to maintain an airway in unconscious or semiconscious patients.

While various embodiments are amenable to various modifications and alternative forms, specifics thereof have been shown by way of example in the drawings and will be described in detail. It should be understood, however, that the intention is not to limit the claimed subject matter to particular embodiments described. On the contrary, the intention is to cover all modifications, equivalents, and alternatives falling within the spirit and scope of the subject matter as defined by the claims.

DETAILED DESCRIPTION

Embodiments described herein are related to LJT mandibular protracting oral airway devices to prevent the obstruction to an airway due to the backward (postero-inferior) movement of the tongue with the lower jaw, palate towards the air passage of the fauces, and oro-naso-laryngo pharynx due to any number of reasons from under anesthesia, semiconscious, cardiac arrest, cerebral accidents, narcotic and alcohol overdose, with many number of systemic diseases and such.

Figure 1A:
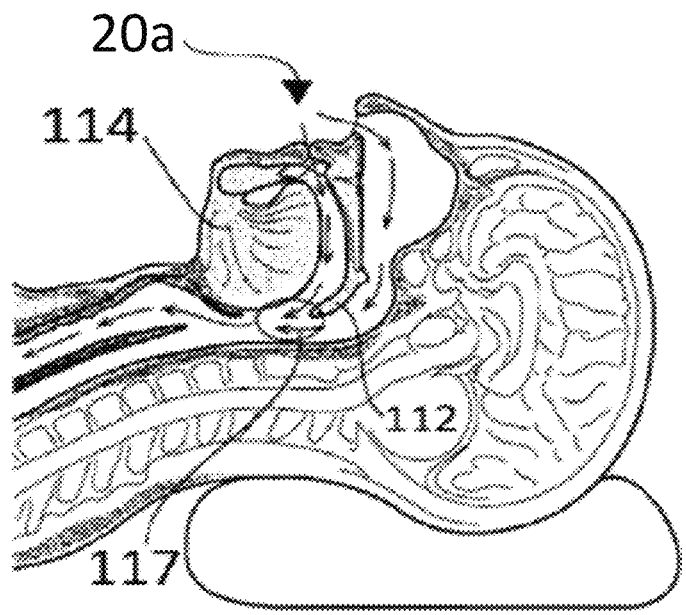
FIG. 1A is a diagram of a normal airway and the position of the tongue, palate, and oropharynx of a patient.
Figure 1B:
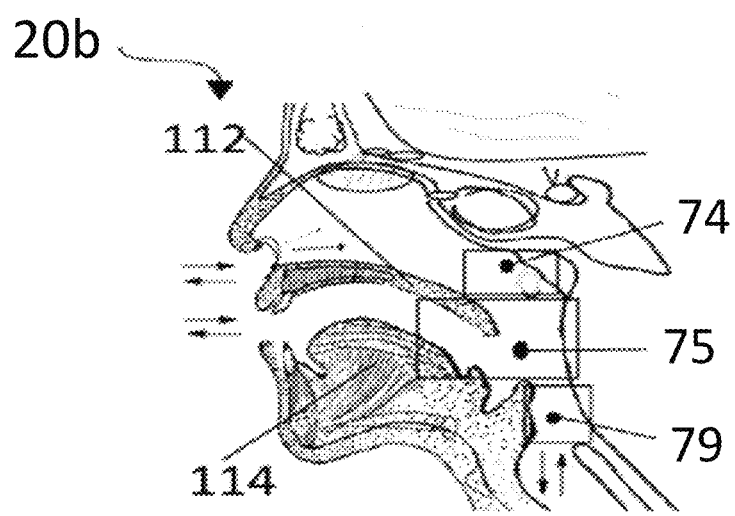
FIG. 1B is a diagram of the anatomical structures of a normal airway of a patient.
Figure 1C:
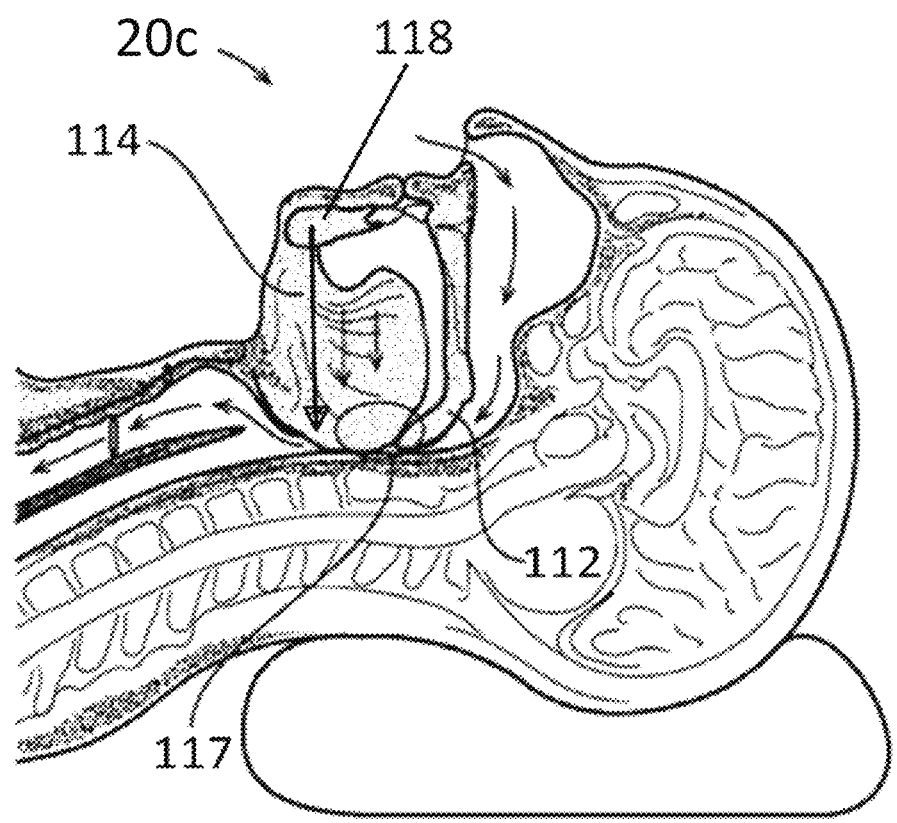
FIG. 1C is a diagram of an oropharynx airway that is obstructed in an unconscious or semiconscious patient due to the movement of the tongue and the lower jaw movement backwards.
Figure 1D:
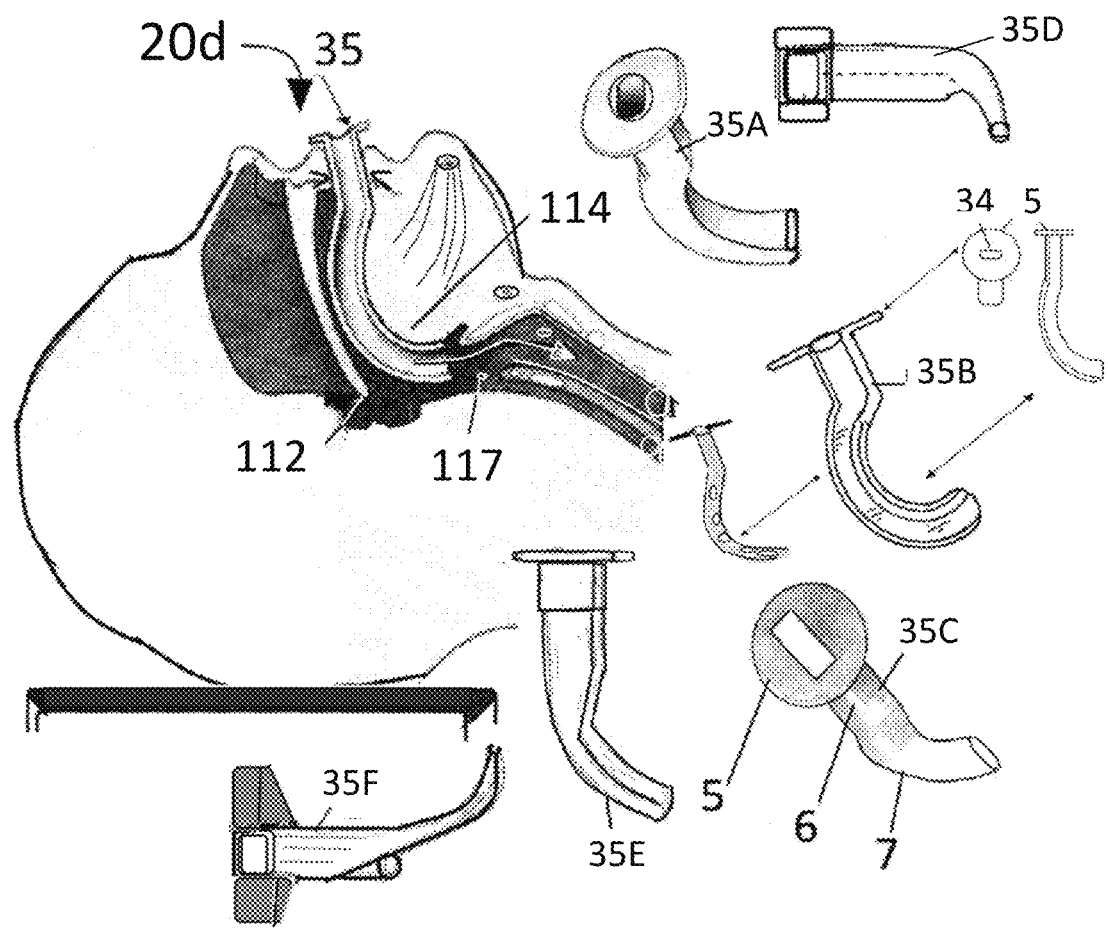
FIG. 1D is a diagram of various different types of existing oral airway devices.
Figure 1E:
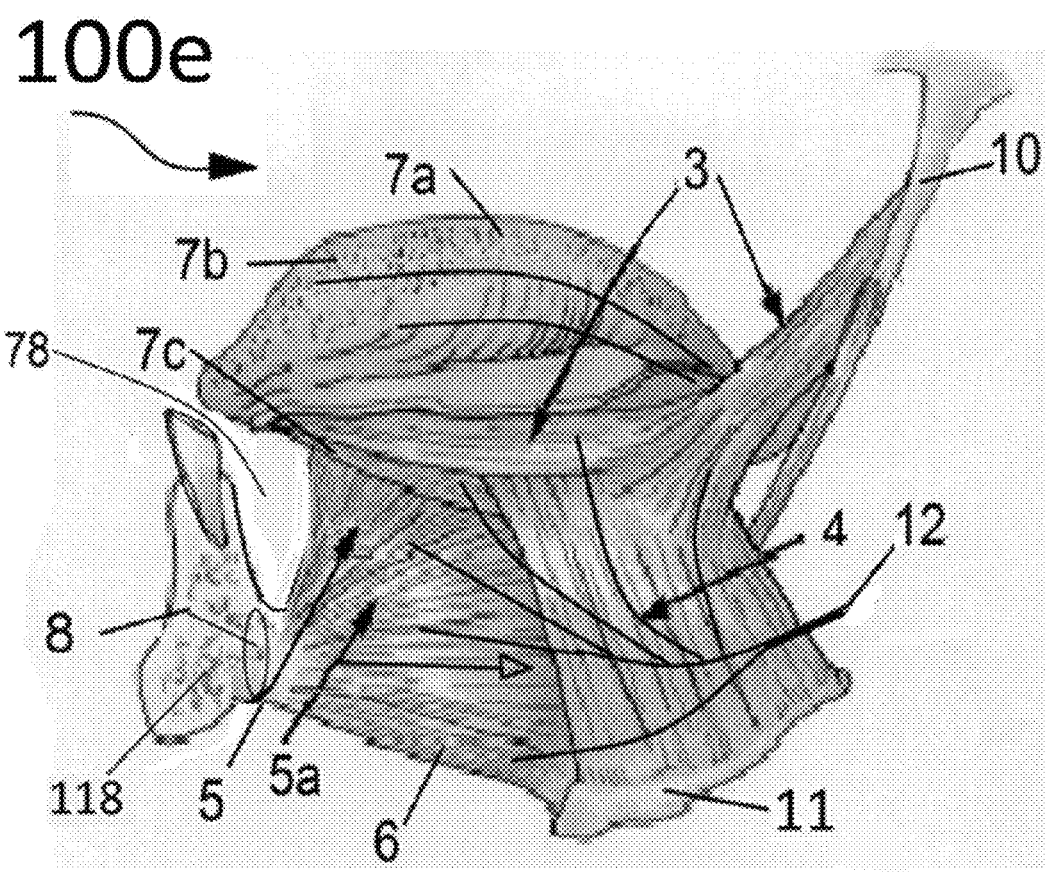
FIG. 1E is a diagram showing the muscles of the tongue and palate involved in the movement of the tongue that block the oral airway under a conscious state.
Figure 1F:
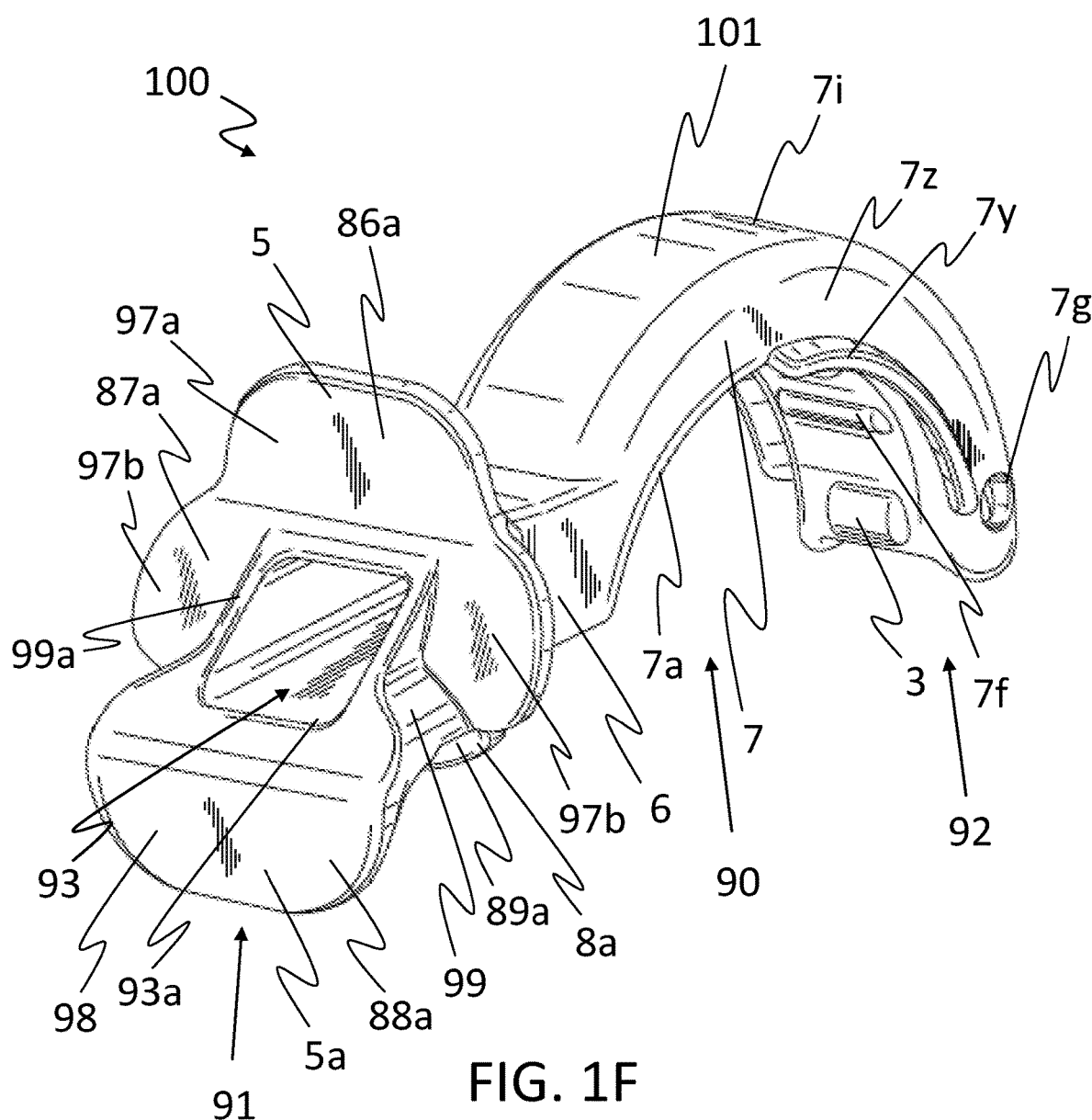
FIG. 1F shows a top perspective view of an LJT mandibular protracting oral airway device, according to an embodiment.

FIGS. 1 through 1E generally relate to various existing known oral airway devices, procedures, and related anatomic information. Specifically, FIG. 1 shows a diagram 20 of existing mandibular protracting jaw thrusting manual procedures and devices to maintain an airway in an unconscious or semiconscious patient. Diagram 20 shows a series of configurations 22A-E showing procedures performed on a subject having an obstruent airway and establishing it back during unconscious-semiconscious states, and CPR. Configuration 22A shows a subject with a tongue 114 falling back against palate 112 blocking the air passage or oropharyngeal airway 117 and accordingly, blocking ventilation. It is taught that during CPR, the movement used to clear an airway obstruction, is to tilt the head back as shown in configuration 22B, pull the chin and thrust the jaw forwards as shown in configurations 22C and 22D, and hold the jaw pulled out as shown with a thrust applied to the angle of the mandible. This will pull the tongue 114 away from the oropharyngeal airway 117 and palate 112, establishing the airway as shown in configuration 22B. Note how both the hands are busy providing the care to the airway. It is here, that embodiments of the LJT mandibular protracting oral airway device of the present disclosure, as later described, will free the hands of a practitioner to otherwise care for the patient. These maneuvers are done millions of time all over the US and around the globe, as the patient is put to sleep and as they emerge from anesthesia and during CPR and such. Once the maneuver is over, most of the time, a prior art ordinary oral airway device 35 is inserted as shown at configuration 22E. This type of oral airway device 35 does not prevent the jaw retraction and the tongue 114 and palate 112 still can move back and block the oropharynx airway 117. On the other hand, embodiments of the LJT mandibular protracting oral airway device of the present disclosure, as later described, will prevent the lower jaw retracting back, tongue and palate moving towards oropharynx. As later described, the LJT mandibular protracting oral airway device of the present disclosure will maintain the oropharyngeal airway 117 of a subject and, at the same time, free both the hands of the caregiver.

FIG. 1A is a diagram of a normal airway 20a with the soft palate 112 and tongue 114 of a subject not obstructing the airway passage 117. This allows the free flow of air from the mouth and the nose to the larynx as the person sleeps on a pillow in supine position. The airflow does not produce a physical force like a narrow air stream.

FIG. 1B is a diagram of a normal airway 20b, and the airway at the back of the nose and tongue as well as larynx. The diagram shows the soft palate 112 and tongue 114 situated at the inlet into the oropharynx 75, also called as faucial isthmus, which is obstructed due to narrowing of the passage and falling back of the back of the tongue and soft palate during sleep, and in unconscious or semiconscious patients. The oropharynx 75 is continuous with nasopharynx 74 and laryngopharynx 79 for unobstructed movement of air either from an oral airway device or those spontaneously breathing.

FIG. 1C is a diagram of an airway 20c of a subject with a soft palate 112 and tongue 114 completely retracting back of the lower jaw 118. This arrangement obstructs the air passage 117 by not allowing the free flow of air from the mouth, and the nose to the larynx, through the oropharyngeal air passageway to the laryngeal inlet as the subject sleeps. This is due to relaxation of the soft palate 112 and the tongue 114 becoming flaccid and falling back with mandible due to reduced skeletal muscle tone on the wall of the oropharynx along with backward movement of the lower jaw 118 with the tongue, creating obstruction to the passage of air. This change in the air passages results in obstructive sleep apnea.

FIG. 1D shows a diagram 20d of many types of existing oral airway devices 35. The oral airway device 35 shown in the subject's mouth demonstrates how it prevents interference by the tongue 114 and palate 112 with its curved body to ward off obstruction at oropharynx airway 117. Diagram 20d shows six kinds of frequently used prior art oral airway devices 35 (individually referred to as oral airway devices 35A, 35B, 35C, 35D, 35E, 35F).

The various oral airway devices 35 each has a rigid C-shaped main body 7, connected to a mouthpiece/bite block 6, that in turn is attached at its forward end to a front lip flange 5, that holds the oral airway device 35 inside the oral cavity of a subject with the help of lip and teeth clenching. Lip flange 5 is a projecting flat rim, collar, or rib on the front part of the bite block 6 of the oral airway device 35. Lip flange 5 serves to strengthen to maintain position of the oral airway device 35 in the mouth without being drawn inside the oral cavity.

Once the jaw thrusting maneuver is performed, most of the time, an existing ordinary oral airway device 35 is inserted. This does not prevent jaw retraction and the tongue 114 and palate 112 still can retract back, pull the mandible backwards and block the oropharynx airway 117. On the other hand, when the LJT mandibular protracting oral airway device of the present disclosure (as later described) is inserted, it will prevent the lower jaw retracting back, tongue and palate moving towards the oropharynx and thus maintain the oropharynx airway 117, and also at the same time free both the hands of the caregiver.

As shown in FIG. 1D, existing oral airway devices 35 come in a number of different sizes and shapes so as to accommodate the anatomical features of any number of different sized individuals. The two most widely used oral airway devices are the Guedel and Berman devices, each named for its inventor designer. The Berman oral airway device, shown generally as oral airway device 35B, has channels along each side of central rib that allow a suction catheter or endotracheal tube to slide into the pharyngeal space. The Guedel oral airway device, shown generally as oral airway device 35C, is a tubular device, having a central lumen that can be used for suctioning. Oral airway device 35C cannot support an ET tube.

Each oral airway device 35 generally has three parts: a lip flange 5, a bite block 6 for placement between a subject's teeth, and a C-shaped main body 7 which curls around a subject's tongue and ends in a tip in front of the epiglottis at the root of the tongue. When properly inserted, the lip flange 5 is the piece that protrudes from the mouth and rests against the lips, preventing the device 35 from suctioning into the pharynx. A central breathing window 34 can typically be located in the lip flange 5. The C-shaped main body 7 follows the contour of the roof of the mouth and surface of the tongue 114, and will curve over and rest on top of the tongue 114 and the distal end, or tip, sits at the base of the tongue. Traditional oral airway devices, including Guedel and Berman devices, 35A, 35B, 35C, 35D, 35E and 35F, will not perform mandibular protracting jaw thrusting movement. A subject's lower jaw and tongue can move backwards towards oropharynx and obstruct the oral airway in spite of these oral airway devices 35 in the mouth unless the jaw is held protracted.

FIG. 1E is a diagram 20e showing the muscles of the tongue and their hypoglossal nerve supply 112 responsible for the movement of the tongue back, resulting in the blockage of the oropharyngeal air passage. It shows the hypoglossal nerve 112 coursing along the Hyoglossus muscle, and branching to supply various muscles of the tongue. This twelfth cranial nerve supplies all the muscles of the tongue except palatoglossus supplied by the ninth cranial nerve. FIG. 1E shows the tongue retractor muscles Styoglossus 103 and Hyoglossus 104. Then it shows the important tongue protruder muscle genioglossus oblique 105 and genioglossus horizontal 105a fibers that prevent the retraction of the tongue. It also shows the geniohyoid 106 which can pull the root of the tongue forwards. The tongue has four muscles and none of them are attached to the bones, hence the tongue can move in all directions depending upon the pull from the root of the tongue. The tongue has superior longitudinal 107a, transverse, and vertical fibers 107b and inferior longitudinal 107c without attachments to the bone. They are innervated by the hypoglossal nerve also arising posteriorly as shown in FIG. 1E. These strong muscles, do not tire or give up, no matter how much they are used for speaking or masticating.

The genioglossus muscle is the primary upper airway dilator and tongue protrusor which the later disclosed, LJT mandibular protracting oral airway device of the present disclosure, automatically restrains by pulling the tongue and jaw back. On the other hand, the hyoglossus and Styoglossus are tongue retrusor muscles that contribute to airway collapse. It is believed that these muscles pull back the root of the tongue against the palate and oropharynx leading to an increase in the weight of the tongue due to flaccidity and obesity in the unconscious, resulting oropharynx airway obstruction.

LJT Mandibular Protracting Oral Airway Device

FIGS. 1F-17 of this disclosure relate to various embodiments of an LJT mandibular protracting oral airway device 101. The LJT mandibular protracting oral airway device can be referred to generically by numeral "101". Additionally, various specific embodiments of LJT mandibular protracting oral airway devices associated with one of the FIGS. can be referred to by numeral "101" followed by an alphanumeric reference character (i.e. 101a, 101b, 101c, etc.). At times, an LJT mandibular protracting oral airway device may be more concisely referred to as an "LJT oral airway device", "oral airway device", or similar variation, for convenience and shorthand purposes.

FIGS. 1F-1J show various views of a first embodiment 100 of LJT mandibular protracting oral airway device 101. Specifically, top perspective, bottom perspective, side, top, and front views are respectively shown. The LJT mandibular protracting oral airway device 101, can be generally understood to relate to an elongate member 90 having a varied, curved shape. The elongate member 90 has a proximal end 91 and a distal end 92 defining an air passageway 93 channel therebetween. Further, the air passageway channel 93 of the elongate member 90 is generally curved, rectangular in cross-section, C-shaped, and can include openings at its ends or along its curved main body 7. In some embodiments, air passageway channels 93 are shown to be partially arcuate and/or tubular in shape. As discussed below, elongate member 90 generally includes a lip flange (i.e. upper lip flange 5 and lower lip flange 5a collectively or individually), a bite block 6, and a curved main body 7.

In FIGS. 1F-1J, the entire device shown is referred to as an elongate member 90. The proximal end 91 is the end associated with the lip flange or flanges (i.e. an upper lip flange 5 and a lower lip flange 5a). The distal end 92 is the end of the device opposite the proximal end 91, at the terminal end of the main body 7. The air passageway channel 93 is only partially visible, but should be understood as extending between these ends as a lumen or partially-defined passage for airflow. Although the elongate member 90, proximal end 91, distal end 92, and air passageway channel 93 are generally not each specifically and individually labeled in the other figures of this disclosure, the location of these features should be readily understood to be generally applicable to or consistent with all figures and embodiments herein, based upon the general description presently being discussed. LJT oral airway devices 101 disclosed are understood to be sized for insertion in a patient's mouth such that the distal end 92 is disposed adjacent the patient's tongue root while the proximal end 91 remains disposed outside the patient mouth.

Figure 1G:
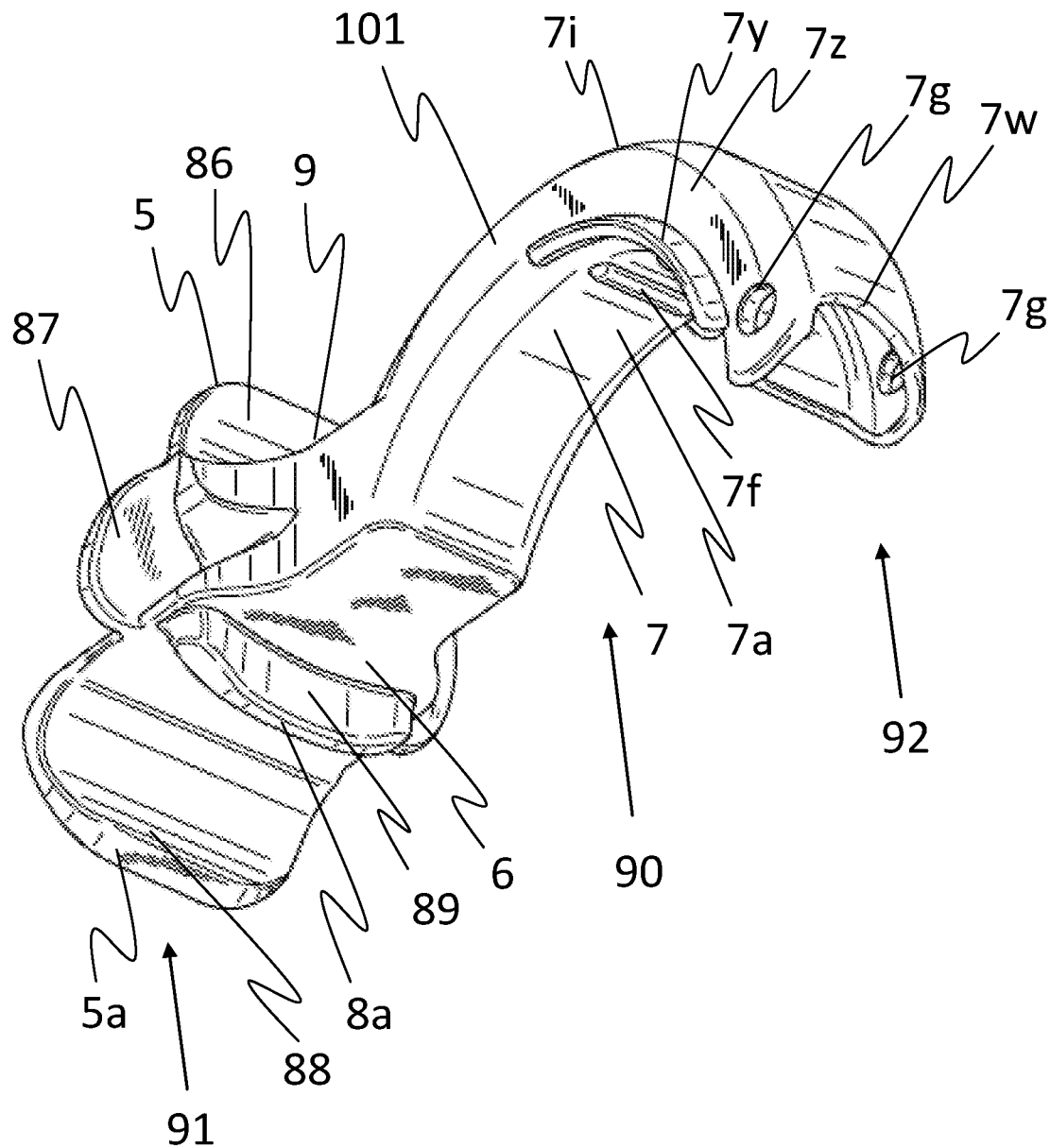
FIG. 1G shows a bottom perspective view of an LJT mandibular protracting oral airway device of FIG. 1F, according to an embodiment.
Figure 1H:
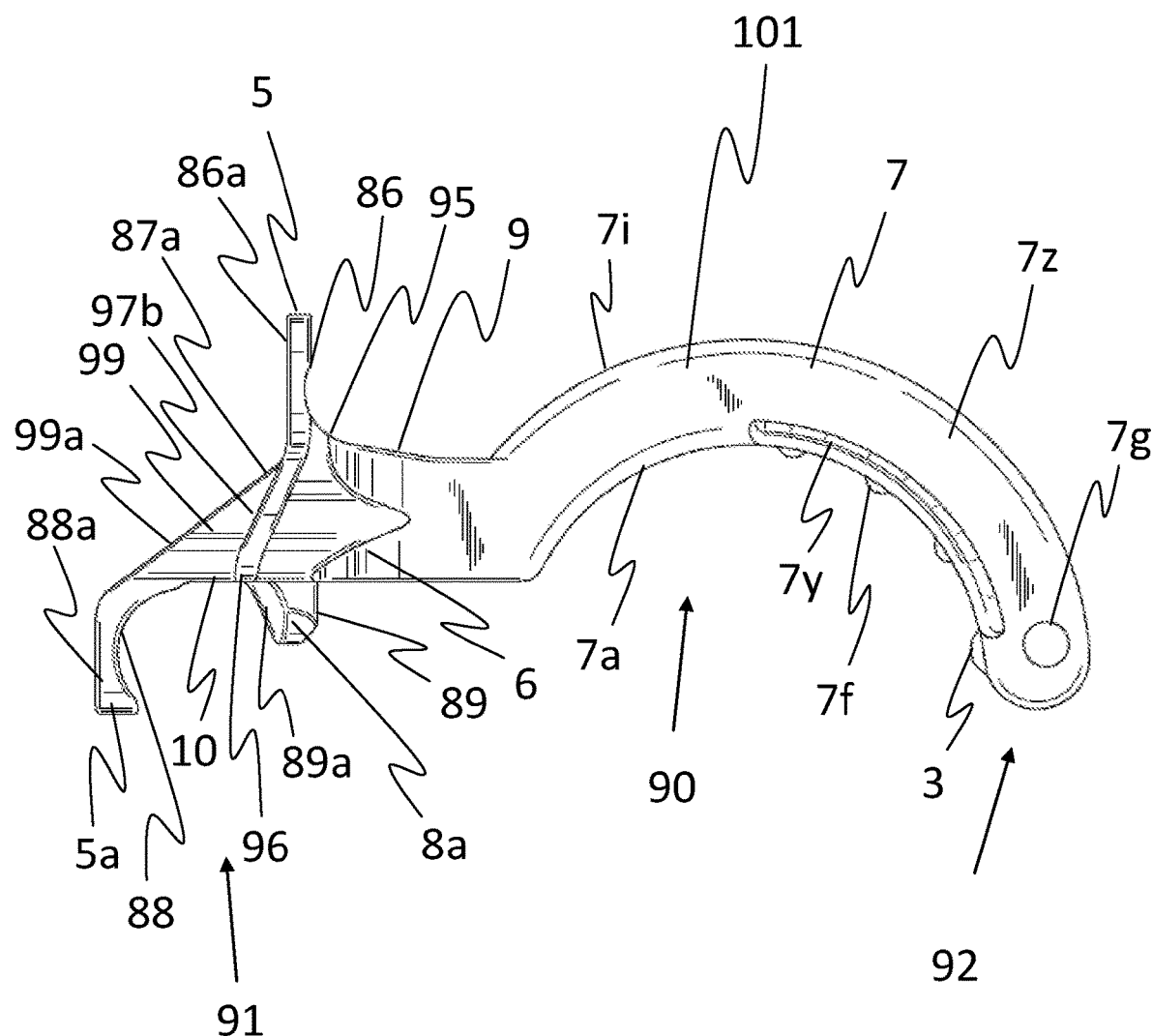
FIG. 1H shows a side view of an LJT mandibular protracting oral airway device of FIG. 1F, according to an embodiment.
Figure 1I:
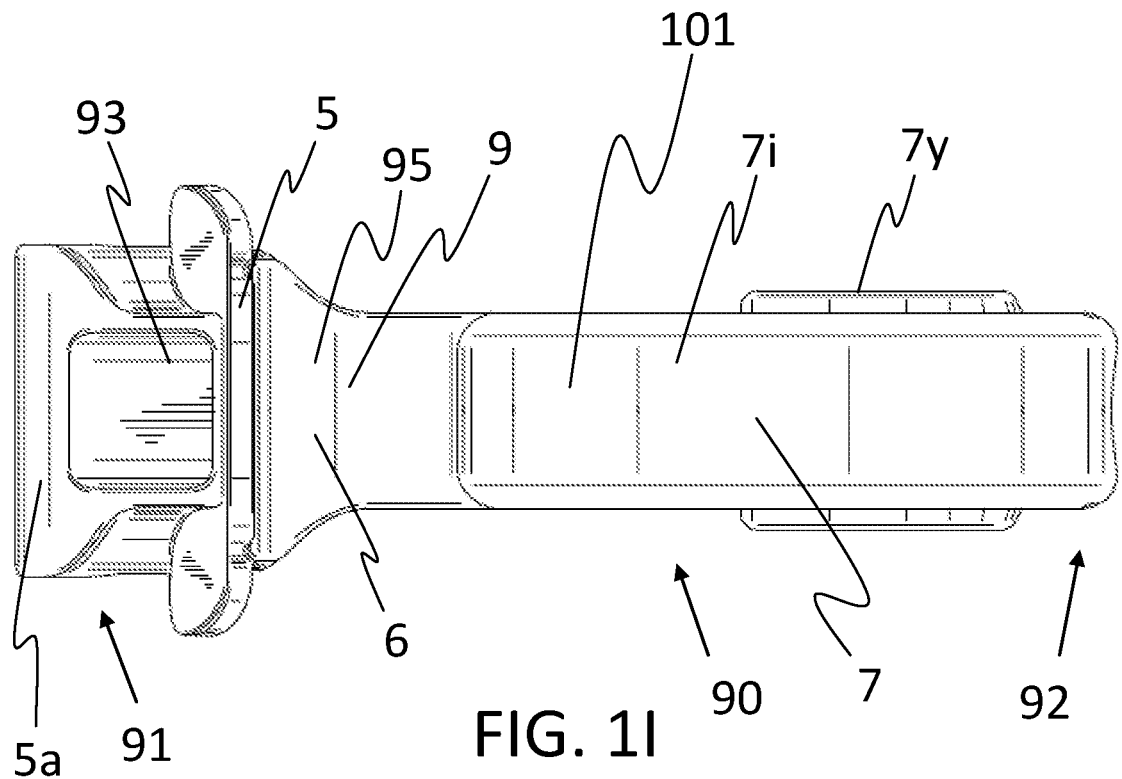
FIG. 1I shows a top view of an LJT mandibular protracting oral airway device of FIG. 1F, according to an embodiment.
Figure 1J:
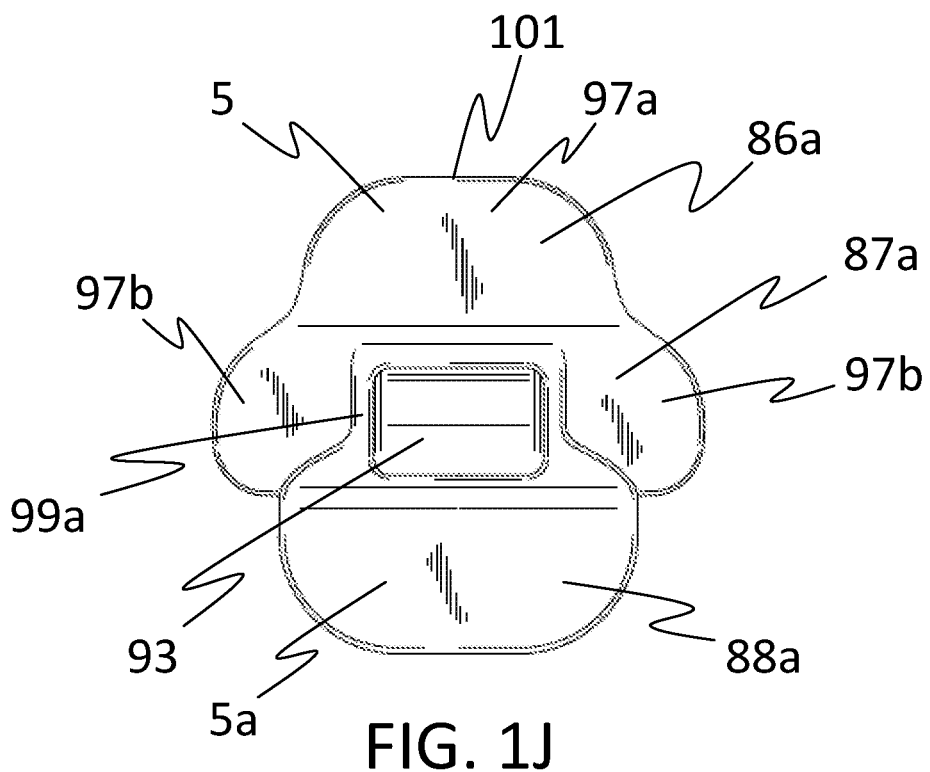
FIG. 1J shows an end view of an LJT mandibular protracting oral airway device of FIG. 1F, according to an embodiment.

As referenced above, the elongate member 90 includes a lip flange (collectively upper lip flange 5 and lower lip flange 5a in FIGS. 1F-1J). The lip flange (5 and 5a), is located at the proximal end of the elongate member 90 having outwardly projecting surfaces configured to overlie the lips of the patient. In general, each of the upper lip flange 5 and lower lip flange 5a is a vertically-disposed member generally projecting outwardly relative to a central opening 93a of the air passageway channel 93. FIGS. 1F-1J depicts a two-part lip flange having an upper lip flange 5 and a lower lip flange 5a. Upper lip flange 5 includes a central flange section 97a and side flange sections 97b. These sections 97a and 97b each have a first distal surface 86 or 87 and an opposing a first proximal surface 86a or 87a. Accordingly, upper lip flange 5 has a first distal surface 86 that is generally vertically-disposed for proximal placement relative to an upper lip of the patient's mouth. Directions such as "vertically-disposed" should be interpreted as being oriented in a up and down direction relative to the device as shown in FIG. 1H, for example. Terms such as "vertically-disposed" should be broadly interpreted and not limited to a narrow entirely vertical angle of orientation or straight/flat surface, for example. For example, the central flange section 97a of upper flange 5, and its surfaces 86 and 86a, are considered vertically-disposed, although not entirely straight or perpendicular to the device orientation. The side flange sections 97b of the upper flange 5, and its surfaces 87 and 87a, are disposed in a generally inclined arrangement. Accordingly, the upper flange 5 provides a barrier which can project around and overlie the lips of the patient. In general, distal surfaces 86 of the upper flange 5 provide a structure to help obstruct and resist maxillary forward movement. Side flange sections 97b of upper lip flange 5 extend downwards to the level of the lower ventral surface 10 of the bite block 6, in front of the mandibular flange 8a. Accordingly, the upper flange 5 can help to seal a patient's mouth opening superiorly and laterally. See FIG. 1H, for example.

The lower lip flange 5a includes a lower central flange section 98. Lower central flange section 98 has a second distal surface 88 and an opposing a second proximal surface 88a. The lower central section 98 is largely vertically disposed and provides a barrier to project in front of the lower lips and mandible of the patient on which it is being used. Accordingly, lower lip flange 5a has a second distal surface 88 that is generally vertically disposed for proximal placement relative to a lower lip of the patient's mouth. Distal surface 88 of the lower lip flange 5a provides a structure that can limit and define proximal movement of the mandible.

In the embodiment of FIGS. 1F-1J, as well as many of the embodiments disclosed throughout this disclosure, the lower lip flange 5a is generally offset from the upper lip flange 5 such that the lower lip flange 5a is located proximal to the upper lip flange 5. Specifically, distal surface 86 of the upper lip flange 5 is distally located compared to the distal surface 88 of the lower lip flange 5a. This offset arrangement of the upper lip flange 5 and lower lip flange 5a assists in restricting and placing a patient's mouth into a lower jaw thrusting position when utilized. Accordingly, a two-piece, lip flange with distally offset upper and lower surfaces with respect to one another, is disclosed. This offset arrangement accordingly, aids in lower jaw thrusting and is disclosed for various embodiments. Accordingly, in various embodiments, the first distal surface 86 of the upper lip flange 5 is located distal to the second distal surface 88 of the lower lip flange 5a.

Further, as shown in FIGS. 1F-1J, an angled connecting region 99 extends between the upper lip flange 5 and lower lip flange 5a and is disposed around a central air passage channel 93. Specifically, an angled surface 99a, of the angled connecting region 99, extends between the proximal surfaces 86a and 88a of the upper lip flange 5 and lower lip flange 5a. Central to this angled surface 99a is an opening 93a to the channel comprising air passageway 93.

Throughout this disclosure, various embodiments may be directed to include a single continuous lip flange 5 or alternatively to a lip flange with an upper lip flange 5 and a lower lip flange 5a. References to a "lip flange" should generally be read broadly to encompass either configuration, unless otherwise specified. Although the outwardly projecting surface(s) such as 86, 86a, 87, 87a, 88, and 88a is/are not specifically labeled in certain figures, these features should be readily understood for all figures and embodiments herein, where applicable, based upon the preceding general description of components.

As referenced above, the elongate member 90 includes a curved main body 7. The curved main body 7 can be understood as extending to the distal end 92 of the elongate member 90. The curved main body 7 is for depressing the tongue and provides downward and inferior tongue pressure that is resistive to backward tongue movement. In some embodiments, the curved main body 7 can be C-shaped.

In FIGS. 1F-1J, the curved main body 7 includes a round nub 3 near the distal end 92 of the elongate body 90 that is configured to engage the patient's tongue root in front of the epiglottis thereby restricting distal backward movement of the tongue root. Further, the curved main body 7 is shown to include a ventral plate 7a on the bottom side of the body. In some cases, as discussed with respect to FIG. 2, for example, the ventral plate 7a may have an oval or rectangular shape. In some cases, the ventral plate 7a may include expanded transverse ridges 7f (or 7b, for example), configured to engage the patient's tongue thereby restricting distal side-to-side tongue movement. Additionally, a pair of lateral extensions 7y can extend along the sides of the ventral plate to aid in restricting tongue movement as well. Lateral extensions 7y can be limited to extension along the distal end of the main body 7 in some embodiments.

LJT oral airway device 101 can also be understood to have an upper member disposed along the top side of the body that is referred to as a dorsal plate 7i. Additionally, plates referred to as dorsolateral plates 7z extend along the sides. Accordingly, the LJT oral airway device 101 has a curved main body 7 that includes a dorsal plate 7i, a bottom ventral plate 7a, and dorsolateral plates 7z extending therebetween. In some embodiments, dorsolateral plate 7z may contain a plurality of holes 7g at the distal end 92 of the main body 7. These holes 7g can be useful in preventing airway obstruction. The distal end 92 of the main body 7, may further contain an opening with a rounded or setback edge 7w to help avoid obstruction and facilitate unrestricted access to the air passage 93.

As referenced above, the elongate member 90 includes a bite block 6. Bite block 6 is disposed between the lip flange (5 and 5a) and the curved main body 7. Bite block 6 includes an upper dorsal surface 9 (or upper depression surface) having a first bite portion 95 for maxillary incisor teeth engagement and a lower ventral surface 10 (or lower depression surface 10) having a second bite portion 96 for mandibular incisor teeth engagement. The bite block 6 includes a mandibular flange 8a projecting downwardly (i.e. outwardly) from the lower ventral surface 10 (or lower depression surface). The mandibular flange 8a is located distal to the second bite portion 96 for mandibular incisor teeth engagement and proximal to the first bite portion 95 for maxillary incisor teeth engagement. The mandibular flange 8a includes a pair of vertically oriented surfaces 89 and 89a on its opposing distal and proximal sides. In some embodiments, the mandibular flange 8a and its surfaces 89 and 89a can have a slight transverse curvature from side to side, as shown in FIG. 1G, to accommodate the shape of a patient's mouth. In the various embodiments, at least vertical surface 89a is located proximal to the first distal surface 86 of the upper lip flange 5. Based on the relationship of these surfaces, advantageous lower jaw thrusting is facilitated by the LJT oral airway device 101.

First bite portion 95 should generally be understood to refer to the portion of the upper dorsal surface 9 adjacent and distal to the vertically-disposed distal surface 86 of the upper lip flange 5. First bite portion 95 corresponds to the location of maxillary incisor teeth engagement as the upper mouth of a patient can be generally urged toward the surface 86 of upper lip flange 5. Second bite portion 96 should generally be understood to refer to the portion of the lower ventral surface 10 that is proximal and adjacent to the proximal surface 89a of the mandibular flange 8a. Second bite portion 96 corresponds to the location of mandibular incisor teeth engagement as the lower jaw of a patient generally will be urged proximally forward by the mandibular flange 8a and its proximal surface. Although the first bite portion 95 and second bite portion 96 are not each specifically labeled in each figure in this disclosure, the these features and locations should be readily understood for all figures and embodiments herein, based upon the preceding general description of components.

In the configuration of FIGS. 1F-1J, maxillary teeth act as a fulcrum and do not move due to a fixed upper jaw in the skull. In other embodiments, as depicted in other figures, a maxillary flange 8 upwardly (i.e. outwardly) projecting from the upper dorsal surface 9 can be included as well to ensure non-movement of the maxillary teeth (e.g., FIG. 2). For example, in such embodiments, the maxillary flange 8 can be located distal to the mandibular flange 8a along the elongate member 90. However, in embodiments like FIGS. 1F-1J, a maxillary flange 8 will not be considered necessary and only a mandibular flange 8a is used to protract and thrust the mandible.

Further, in some embodiments, the bite block 6 of the LJT oral airway device 101, has an upper dorsal surface 9 that provides a depression at the first bite portion 95 and the lower ventral surface 10 that provides a depression at the second bite portion 96. (e.g., see FIG. 3H). Although not specifically depicted in FIGS. 1F-1J, in some embodiments, the upper dorsal surface 95 and lower ventral surface 96 of the bite block 6 can be made up of resilient material.

Similar to the embodiment 100 and LJT mandibular protracting oral airway device 101 of FIGS. 1F-1J, each of the embodiments described throughout this disclosure and figures, can each be generally understood to relate to an LJT mandibular protracting oral airway device 101 (i.e. 101a, 101b, . . . ) comprised of an elongate member having a varied, curved shape, having a distal end and a proximal end defining an air passageway channel therebetween. Any descriptions related to FIG. 1F-1J that can be deemed general in nature should be deemed applicable to any other potentially applicable embodiments referenced or discussed throughout this disclosure. Diagram 100 and LJT mandibular protracting oral airway device 101 should not be viewed as a limiting embodiment with respect to reference numerals only specifically appearing in this figure, for example.

Figure 1K:
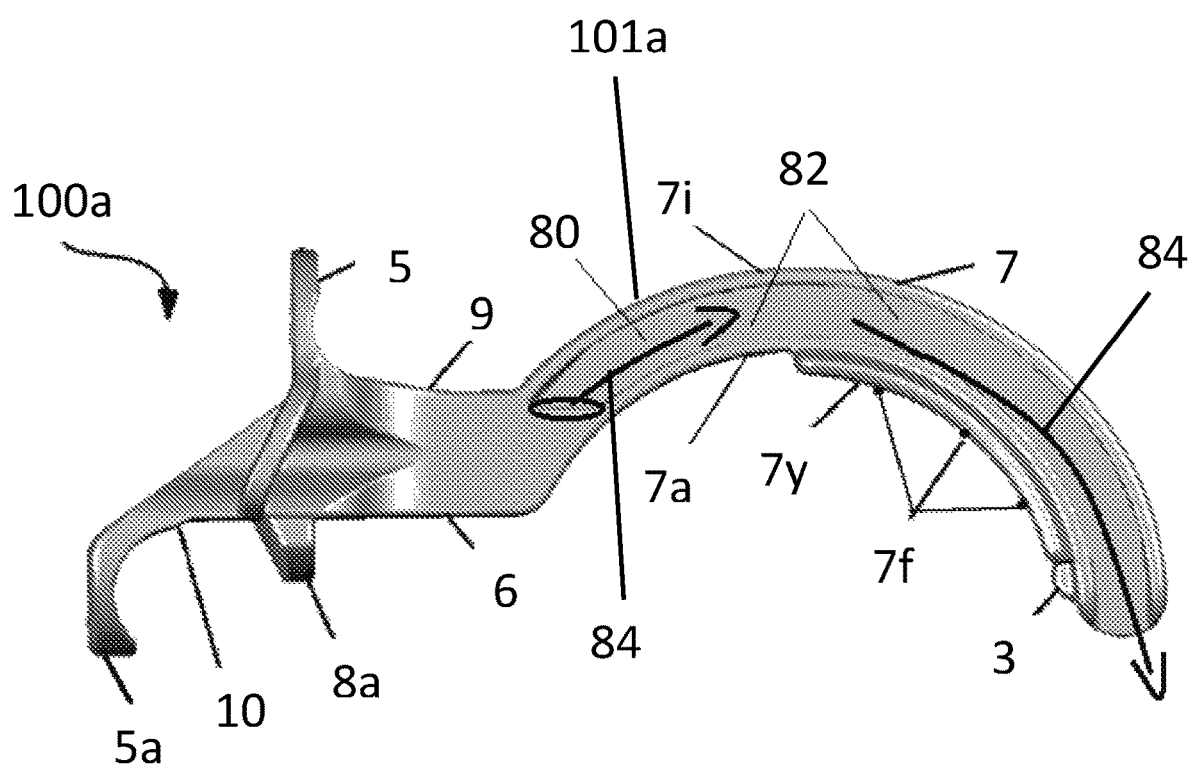
FIG. 1K shows a side view of an LJT mandibular protracting oral airway device, according to an embodiment.

FIG. 1K is a diagram 100a showing an embodiment of an LJT mandibular protracting oral airway device 101a. The LJT mandibular protracting oral airway device 101a shown is generally similar to device 101 of FIGS. 1F-1J and is shown with a side view similar to that of FIG. 1H. The primary difference between the device 101a of FIG. 1K and the previous embodiment 101, relates to the open channels 80 extending along the sides of the main body 7. In this embodiment, main body 7 largely comprises a central rib 82 extending down the middle of the device. The central rib 82 generally extends between a dorsal plate 7i and a ventral plate 7a. Such an arrangement can provide additional airflow and movement for certain procedures and applications. Arrows 84 generally depict air movement through the device 101a.

Figure 1L:
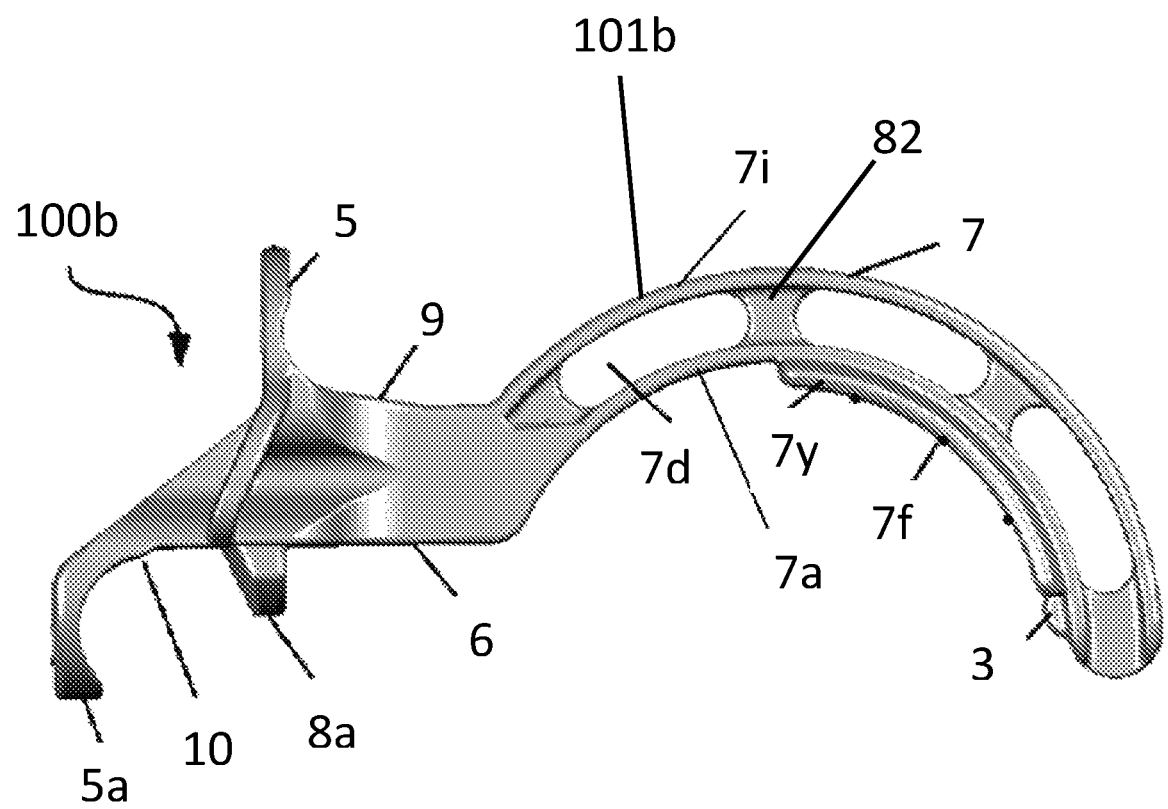
FIG. 1L shows a side view of an LJT mandibular protracting oral airway device, according to an embodiment.

FIG. 1L is a diagram 100b showing an embodiment of an LJT mandibular protracting oral airway device 101b. The LJT mandibular protracting oral airway device 101a shown is generally similar to device 101 of FIG. 1K except that openings 7d are provided in the central rib 82 between the dorsal plate 7i and ventral plate 7a. These openings 7d allow ventilating air and allow secretions to travel from one side to the other, for easy removal by suctioning.

Figure 1M:
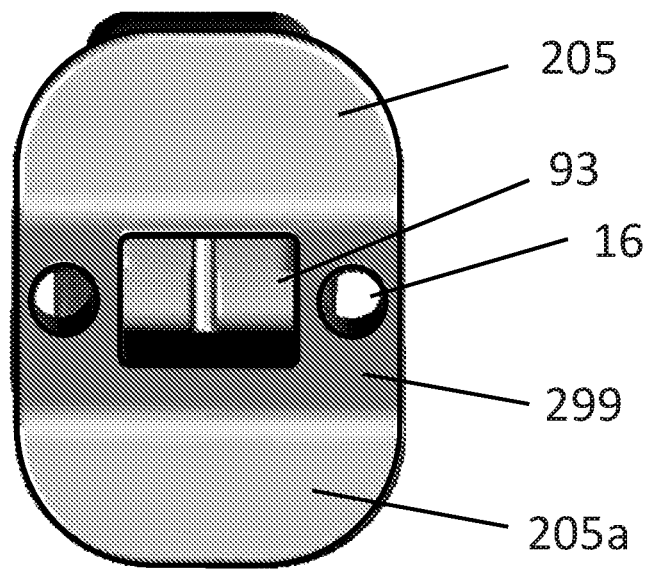
FIG. 1M shows an end view of an LJT mandibular protracting oral airway device, according to an embodiment.

FIG. 1M shows an end view of an alternate lip flange and bite block for an LJT mandibular protracting oral airway device 101, according to an embodiment. In general, an upper lip flange 205 and lower lip flange 205a is shown which is joined by an inclined section 299. Upper lip flange 205 is generally located distal to the lower lip flange 205a. Air passageway channel 93 is centrally located in the inclined section 299 and openings 16 are found on both sides of passageway 93 in the inclined section 299 as well.

Upper lip flange 205 and lower lip flange 205a make up a lip flange which is generally slimmer that the lip flanges 5 and 5a shown in FIGS. 1F-1J. No side flange sections are included as part of upper lip flange 5, for example.

Figure 1N:
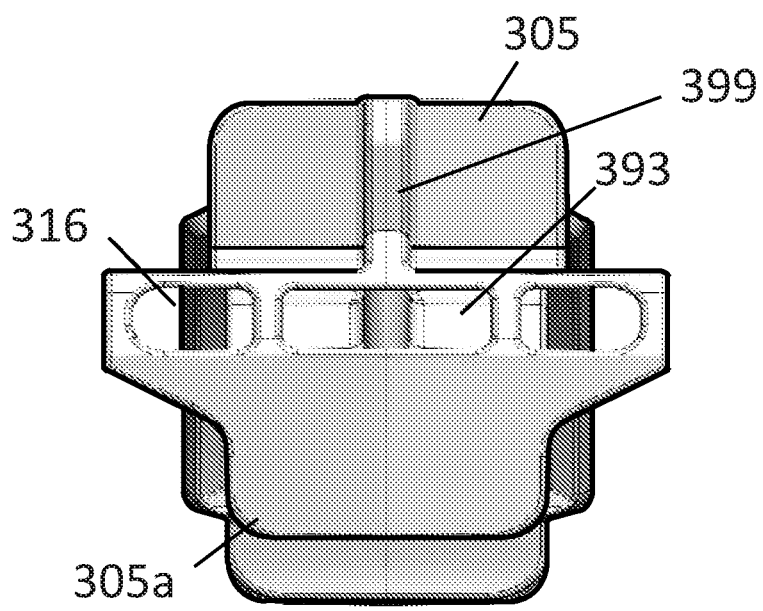
FIG. 1N shows an end view of an LJT mandibular protracting oral airway device, according to an embodiment.

FIG. 1N shows an end view of an alternate lip flange and bite block for an LJT mandibular protracting oral airway device 101, according to an embodiment. In general, an upper lip flange 305 and lower lip flange 305a is shown which is joined by an inclined central section 399. Upper lip flange 305 is generally located distal to the lower lip flange 305a. The front lip flanges 305 and 305a are attached to the front of the bite block 6.

Lower lip flange include a centrally located feature having a plurality of connector holes 316 and a main airway passage perforation 393. Connector holes 316 accommodate prongs to deliver the nasal oxygen. Main airway perforation 393 is located in the center between the upper lip flange 305 and lower lip flange 305a lip flanges. Connector holes 316 that can be used to connect the LJT oral airway device 101 to a supply of supplementary air or medical gas such as oxygen and anesthetic gases as needed. The connector holes 316 also act as inlets for suctioning of the mouth before extricating the oral airway device 101.

Figure 2:
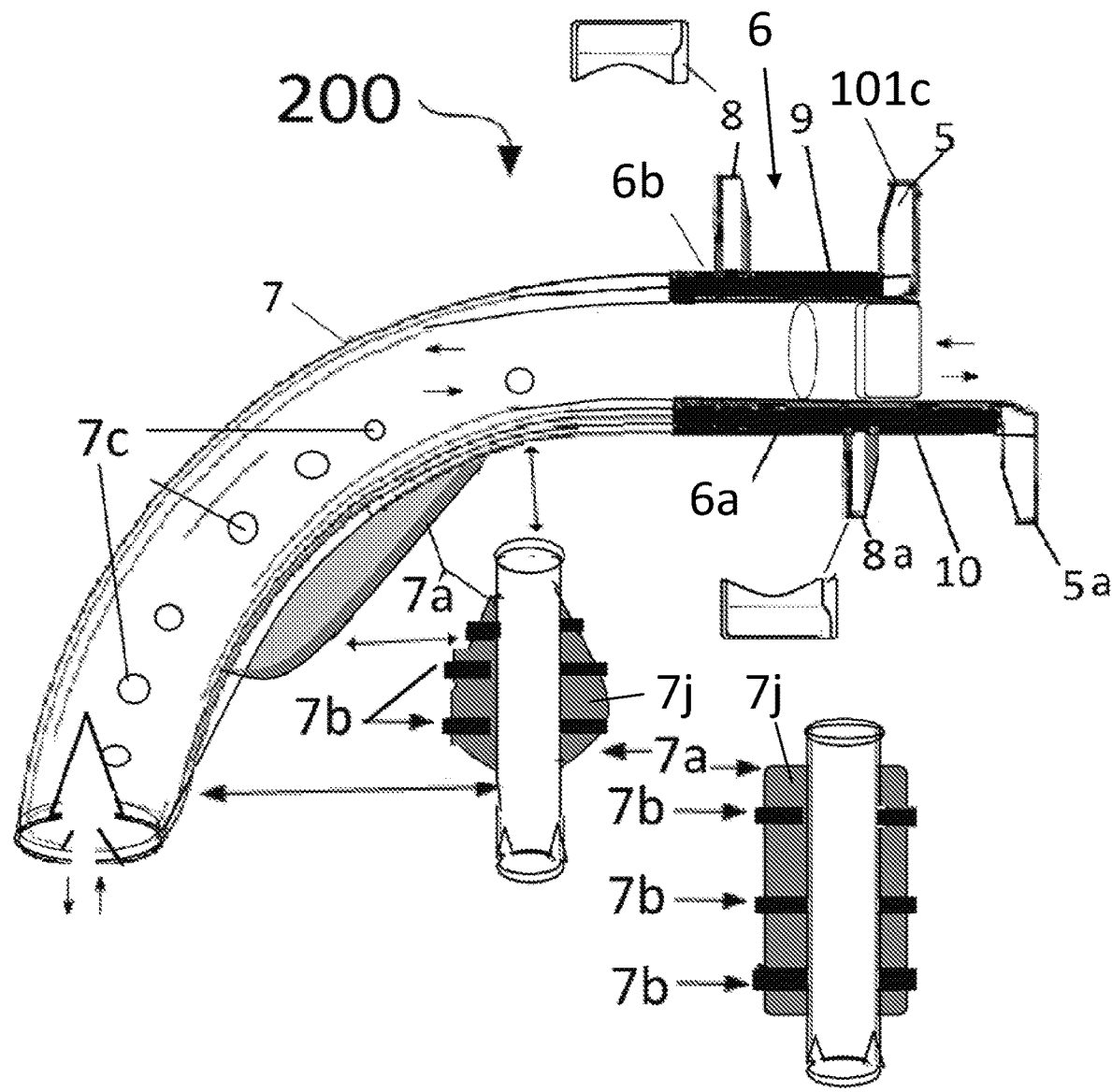
FIG. 2 is a diagram of an LJT mandibular protracting oral airway device with mandibular protracting and maxillary fixing, according to an embodiment.

FIG. 2 shows diagram 200 with the LJT mandibular protracting oral airway device 101c for preventing airway obstruction of the tongue and palate by protracting the lower jaw. This LJT oral airway device 101c is different than the existing oral airway devices 35, as set forth in FIGS. 1 and 1D for example, which are used all over the world. The LJT oral airway device 101c shown in FIG. 2 includes a bite block 6. The bite block 6 is spilt into a longer mandibular part 6a and short maxillary part 6b. The bite block 6 prevents a patient from deforming or biting a portion of the LJT oral airway device 101c accidentally by using their incisor teeth. Such risks are eliminated as the LJT oral airway device 100c does not allow the upper and lower incisors teeth to come in opposition to exert sufficient pressure into the bite block 6. This LJT oral airway device 100c has a rigid main body 7 with a rigid mouthpiece (bite block) 6 attached at the forward end to upper lip flange 5, and longer lower lip flange 5a. The C-shaped, circumferential wall of the mouth piece main body 7 extends from distal end of the bite block 6 located at the mouth of a patient to the distal end of the device, located proximate to the epiglottis of a patient when inserted.

Bite block 6 is completely different than those in traditional oral airways. Bite block 6 has a mandibular flange 8a (or mandible protruder/thruster holder flange 8a) with space (i.e. pocket) for mandibular incisor teeth proximate an adjacent surface 10, to hold the teeth in position and prevent the subject's jaw from moving backward. Thus, the jaw is thrust forward, freeing the hands of a medical caregiver to attend to other care of the unconscious/afflicted. For example, the mandibular flange 8a can be located about ±0.25 inches to 1 inch in front of the upper lip flange 5 of the oral airway device 101c so as to hold the mandible protruded and is held in position by pulling the jaw in position to pull the patient's tongue forward to open the patient's oropharyngeal airway (see FIG. 1). The upper maxillary flange 8 has a surface 9 (i.e. pocket) for maxillary teeth and can hold the maxillary teeth firmly behind the thrusted mandible, as it acts as a fulcrum. In some embodiments, the maxillary flange 8 can be short or absent due to fixed maxilla with incisor teeth.

It has been noted that patients undergoing general anesthesia have infrequent difficulties maintaining their airway and the ability to ventilate. This has happened even after proper placement of the recommended size of Guedel and Berman oral airway devices due to a flopping tongue on one of the sides of the airway to another. In various embodiments of oral airway device 101c, as shown in FIG. 2, there is an oval or rectangular plate 7j with smooth edges extending up to 5 mm beyond the edges of the ventral surface 7a of main body 7. Further, in various embodiments, one to three cross ridges 7b are provided that are raised from the ventral surface 7a so as to press a tongue down and posteriorly to prevent any waggling side-to-side movement or slipping around the endotracheal tube if one is in place.

The Guedel type oral airway device (see device 35C in FIG. 1D) has a disadvantage in that although it holds the oropharyngeal passage open, it does not hold the patient's naso-pharyngeal passage open and in some conditions, may obstruct the naso-pharyngeal passage from its dorsal surface. The maintenance of the naso-pharyngeal passage at the distal end of a Guedel oral airway device can be necessary to maintain the availability of oxygen at the pharynx if the patient is receiving oxygen supplementation through the nose, for example by nasal prongs of a nasal cannula at low flow rates or at higher flow rates or through the oral airway.

Prevention of a nasopharyngeal airway blockage can be accomplished by using an LJT mandibular protracting oral airway device 101c with naso-pharyngeal ventilating holes 7c along the mid-lateral position of a Guedel type, LJT oral airway device 101c on one or both sides. This arrangement replaces the need to use nasal prongs with high flow of oxygen. If ventilating holes are placed in the center sagittal line on the dorsum of the oral airway, they can be obstructed by a flaccid palate. The prongs of a nasal oxygen delivery catheter are positioned on the delivery holes 16. When an oral airway device 101 is positioned in the throat of a patient, at least one aperture in the airway tube allows fluid, such as air or medical gas, to pass through the nasopharyngeal passage. Positioning at least one aperture near the distal end of the airway tube facilitates transfer of gas through the naso-pharyngeal passage.

In contrast to devices that obstruct or do not hold a patient's naso-pharyngeal passage open, the mandibular protracting LJT oral airway device 101c is provided with multiple ventilating holes 7c on the dorsal surface and/or mid lateral wall facing nasopharynx, to keep open the nasopharynx supplied with oxygen delivery and allow the use of fiber optic scopes through this oral airway device 101c, thus overcoming the above-mentioned problems. A slit 7m on the mid-lateral position shown in FIG. 2B also serves the same purpose. The LJT oral airway device 101c can be made of polyethylene or PVC, among other materials, for example. These materials provide the stability of the tube and allow for it to be positioned within the oral cavity and the throat of a patient.

Accordingly, embodiments provide modifications of oral airway devices in the market which will provide better depressive pressure on the tongue against the floor of the mouth by way of: 1) a longer middle support distance which increases the distance the tongue is elevated against the floor of the mouth thus increasing the anterior-posterior dimension of the oral airway opening; 2) a greater width of the curved lower member of the curved section of the oral airway which will give better suppressive support to the tongue laterally, thus increasing the side-to-side dimension of the airway opening; 3) horizontal ridges (See FIGS. 2 and 3H) on the ventral surface of the Guedel and Berman type airways that prevent backward movement of the slippery tongue; 4) mandibular protracting jaw thrusting movement created and maintained by oral airway device 101. This pulls away the tongue from collapse of the faucial isthmus and prevents the tongue from moving back to obstruct from lean to obese patients and keep the airway open to ventilate during induction of anesthesia, and as they emerge from anesthesia and other conditions including during CPR; 4) pulling the root of the tongue away from the epiglottis.

The Guedel and Berman oral airway devices 35C and 35B, as well as other existing oral airway devices in use, are not wide enough ventrally to provide side-to-side support for the slippery tongue of the obese and short people and those with macroglossia and those who suffer from pituitary gland tumors or myxedema. Hence, oval or teardrop shaped thick plastic plates 7j have been added, as shown in the FIG. 2, including ridges 7b. Plates 7j can be located on the ventral surface of Guedel, Berman or any other type of oral airway device. The plate edges extend about 1 to 5 millimeters beyond the lateral surface of the oral airway device 101 on the distal part of the oral airway device 101. The smooth edges of this addition will prevent sliding back of the tongue completely from side to side and prevents its slippage to one or the other side and at the same time open the airway to ventilate by mask or breath spontaneously. This addition will provide additional support for the tongue that is needed to open the airway. This plate 7j will provide greater width of the curved lower member of the curved section of the oral airway, which will give better support to the tongue laterally, thus increasing the side-to-side dimension of the airway opening. Embodiment can also be provided with horizontal ridges to prevent the backward sliding of the tongue. These additions will not alter the length or the radius of the curve of the airway. These embodiments (see FIGS. 2, 3H, for example) will give better tongue support and therefore a larger opening of the patient's airway to facilitate easier ventilation of the patient. This can be especially helpful in obese patients with large tongues or due to any number of medical conditions. This can also be useful for all patients being administered general anesthesia during induction and waking up as well as in semi-conscious patients under sedation.

The LJT oral airway device 101c also serves many functions. The flange and mouth bite block 6 can be made of hard plastic of non-allergic, non-reacting synthetic or semi-synthetic material, for example. On the other hand, the body of the oral airway can be rigid as used in popular oral airway devices and can incorporate soft plastic in the distal one third or so of the body, that is not irritable in people emerging form unconsciousness who are spontaneously breathing and does not elicit gag, coughing, and vomiting reflex when it comes in contact with the epiglottis and sensitive posterior third of the tongue.

Figure 2A:
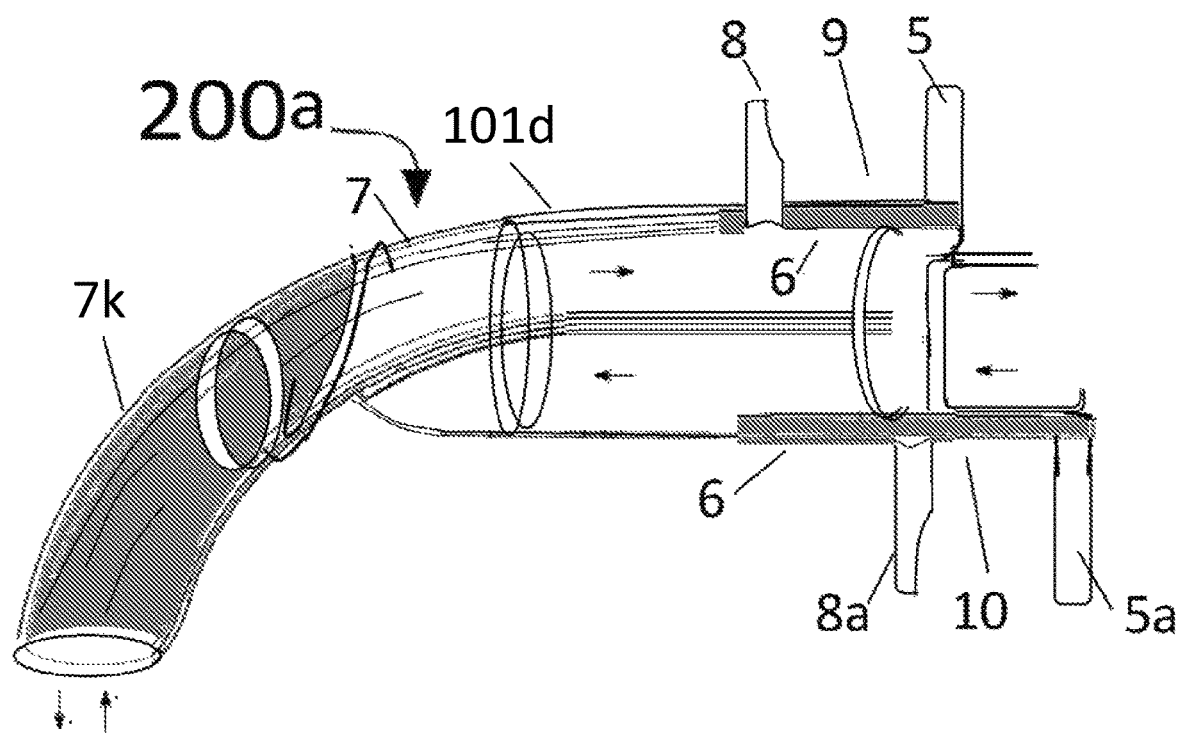
FIG. 2A is a diagram of an LJT mandibular protracting oral airway device with mandibular and maxillary flanges, according to an embodiment.

FIG. 2A shows a diagram 200a of a LJT mandibular protracting oral airway device 101d for preventing obstruction of an airway by the tongue and palate. This oral airway device 101d also is different than the existing oral airway devices 35, such as those shown in FIGS. 1 and 1D, for example. The explanations of FIG. 2A should be understood to be generally consistent with those of FIG. 2. The main body 7 extending from the oral bite block 6 is larger in diameter to allow the easy introduction of fiber-optic scopes to examine, biopsy, and treat respiratory and the esophagus gastrointestinal system. The upper flange 8 of the bite block 6 is placed behind the mandibular flange 8a on the top of the bite block 6, to use the maxilla as a fulcrum to hold the lower jaw forward and control the tongue to introduce scopes including endotracheal tubes.

Oral airway devices are often used in patients undergoing sedation by anesthesia to provide an airway from the mouth to the oropharynx. The standard oral airway device is made of a hard plastic. The use of a typical hard plastic airway is nevertheless sometimes used with intravenous sedation, during which the patient is breathing on his or her own, and does not need an endotracheal tube. It is uncomfortable and can create gag reflex, coughing and vomiting when the patient is less sedated and is emerging from anesthesia, breathing on their own spontaneously. Hence in this LJT oral airway device 101d, the oral piece main body 7 is made of hard/rigid plastic up to the middle of the bite block 6 (2nd molar teeth level), and the rest of the main body posterior 7k is made of soft plastic or silicone that does not collapse on the air passage, and at the same time is non-irritating, malleable and soft to prevent gag reflex as the patients are emerging from anesthesia or sedation.

The oral airway device 101d may be either a 110 mm, 100 mm, 90 mm, 80 mm, 70 mm, 60 mm, 50 mm, or 40 mm size like standard oral airway device sizes used all over the world. These sizes are roughly correlated to general anatomic dimension described as the distance from the exterior of the front teeth to the back of the oropharynx marked at ear lobe and posterior end of the mandible. So, correspondingly, a 40 mm oral airway device is an appropriate size for a premature infant whereas a 110 mm oral airway device is probably appropriate for a large adult, and a 90 mm oral airway device is generally used on a medium adult patient. Obese patients have a thick tongue and have a large quantity of soft tissue in the oropharynx, hence need a larger airway than the measurements indicate.

Figure 2B:
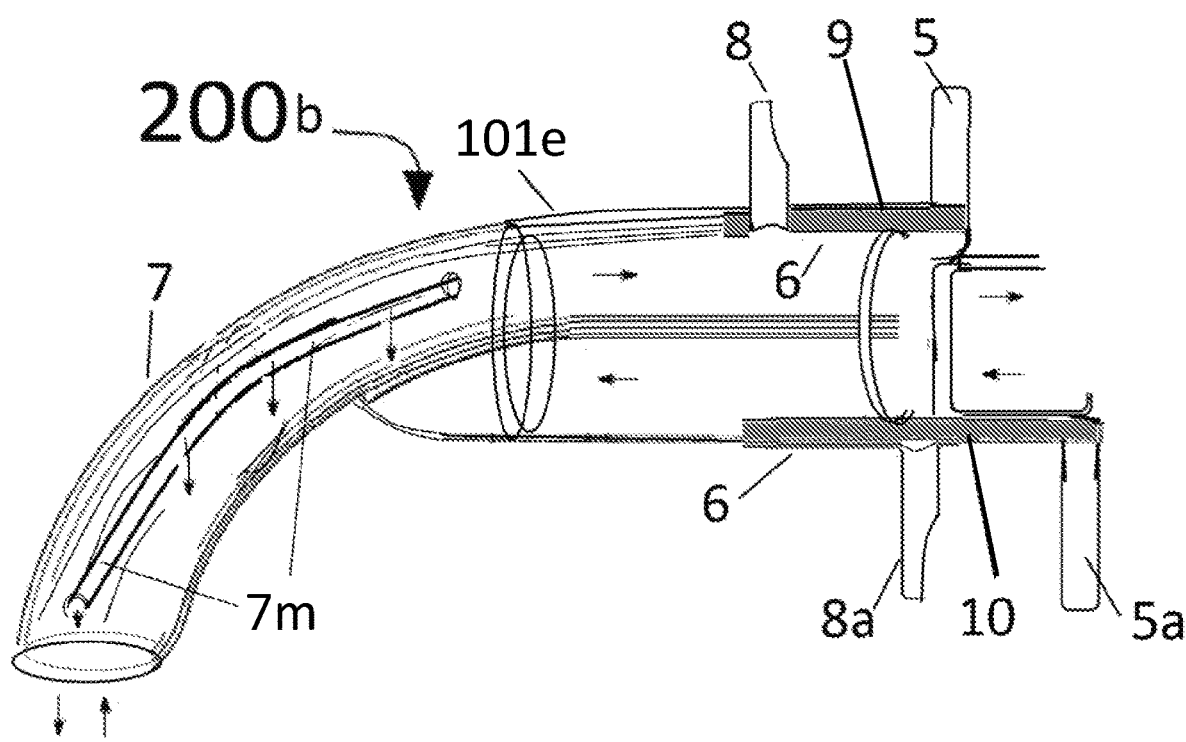
FIG. 2B is a diagram of an LJT mandibular protracting oral airway device, according to an embodiment.

FIG. 2B shows a diagram 200b of a LJT mandibular protracting oral airway device 101e for preventing obstruction of an airway by the tongue and palate. This oral airway device 101e also is different than the existing oral airway devices 35, such as those shown in FIGS. 1 and 1D. This LJT oral airway device 101e has at least one slit 7m along the longitudinal axis of the LJT oral airway device 101e which provides an aperture through the circumferential sidewall of the airway tube. Thus, at least one slit 7m allows the passage of air or medical gas from outside of a patient to the lungs of a patient through the nasopharyngeal passage besides the oropharynx-pharyngeal air passage in case it is obstructed. The advantage of one or two slits on one or both mid-lateral surface slits in the airway tube provides a large surface area that can be used for fluid and supplemental oxygen flow. The tube can be formed from a suitably rigid material such that the presence of at least one slit does not have an effect on the structural integrity of the oral airway tube. Different sizes of slit 7m in the airway tube may be beneficial in different situations, for example larger slits may be beneficial if a high level of oxygenation is required. The explanations of FIG. 2B should be understood to be generally consistent with those of FIG. 2.

Figure 3:
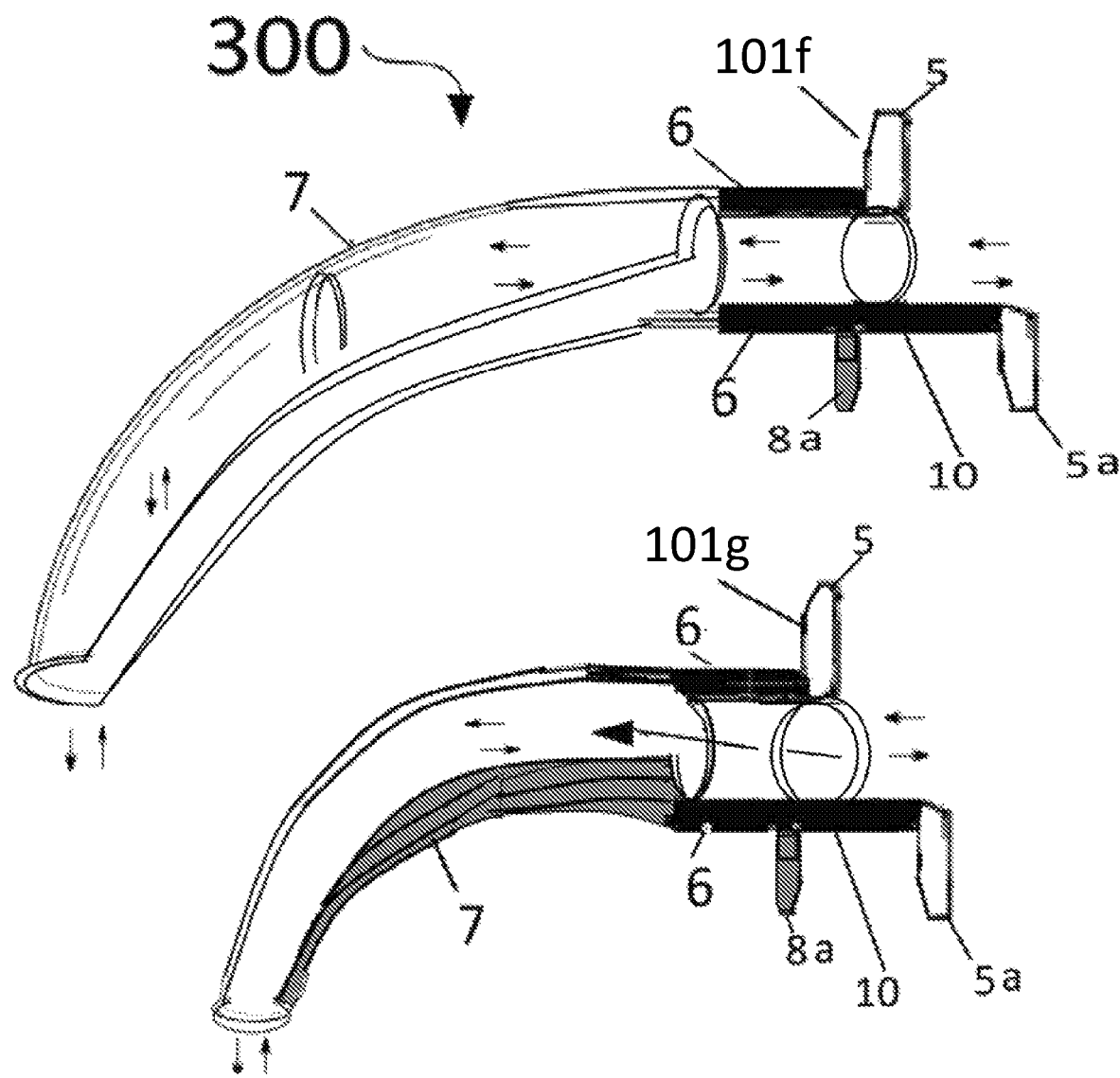
FIG. 3 is a diagram of LJT mandibular protracting oral airway devices having an open ventral dorsal surface on the oral part with a mandibular flange on the bite block, according to an embodiment.

FIG. 3 shows a diagram 300 of a LJT mandibular protracting oral airway device 101f without a dorsal or ventral plate. This is a modified Guedel Airway by Miller with an open or cut away distal end. The open distal end permits placement and movement of the fiber optic scope while providing a bite block. A Williams intubator fiber optic scope facilitator can also be used as an oral airway device. The device 101g generally shows the same device as the LJT oral airway devices 101 in FIG. 2, except that the dorsal cover of the mouth palate restrainer is open to the roof of the mouth. This is explained by the Ovassapian airway, which is a modified oral airway device designed for use with a flexible fiberoptic laryngoscope. The LJT oral airway device 101f may be removed without disconnecting or displacing the endotracheal tube, and the oral airway device has only half a ventral body, like a trough. The Miller and Ovassapian existing oral airway devices facilitate the intubation of fiber optic insertion and still lacks the mandibular protracting jaw thrusting embodiment of LJT oral airway device 101. Hence, one embodiment of the oral airway device 101f provides a modification to these oral airway devices. Oral airway devices 101f and 101g only have a mandibular flange 8a. The partial mandibular surface of the oral part is rigid and holds the tongue restrained preventing its retrograde movement. The main body 7 is a trough that can be reversed to an arrangement in which the ventral surface of the oral part is deficient instead of the dorsal part. The explanations are generally the same for FIGS. 2 and 3 except that the device in FIG. 3 does not have a maxillary teeth restrainer, because the maxilla and its incisor teeth are fixed.

A number of designs of bite block and introducer devices for bronchoscopes and laryngoscopes, such as the Ovassapian, Miller, or Berman airway, have been developed which have ventral and dorsal deficiencies and channels within them. However, these devices are not suitable for use as a routine oral airway device due to their lack of mandibular protracting jaw thrusting effect, even though these oral airway devices can facilitate the passage of some scopes, endotracheal tube and fiberoptic insertion as well as suction catheters and nasal oxygen delivery canula. The LJT mandibular protracting oral airway device 101 overcomes these impediments and obstacles by incorporating a mandibular flange on the ventral surface of the bite block 6, which will improve functioning of the device, which will hold the protracted mandible firmly in position for easy intubation and fiberoptic examination of the air and laryngeal passages including tracheobronchial tree.

Figure 3B:
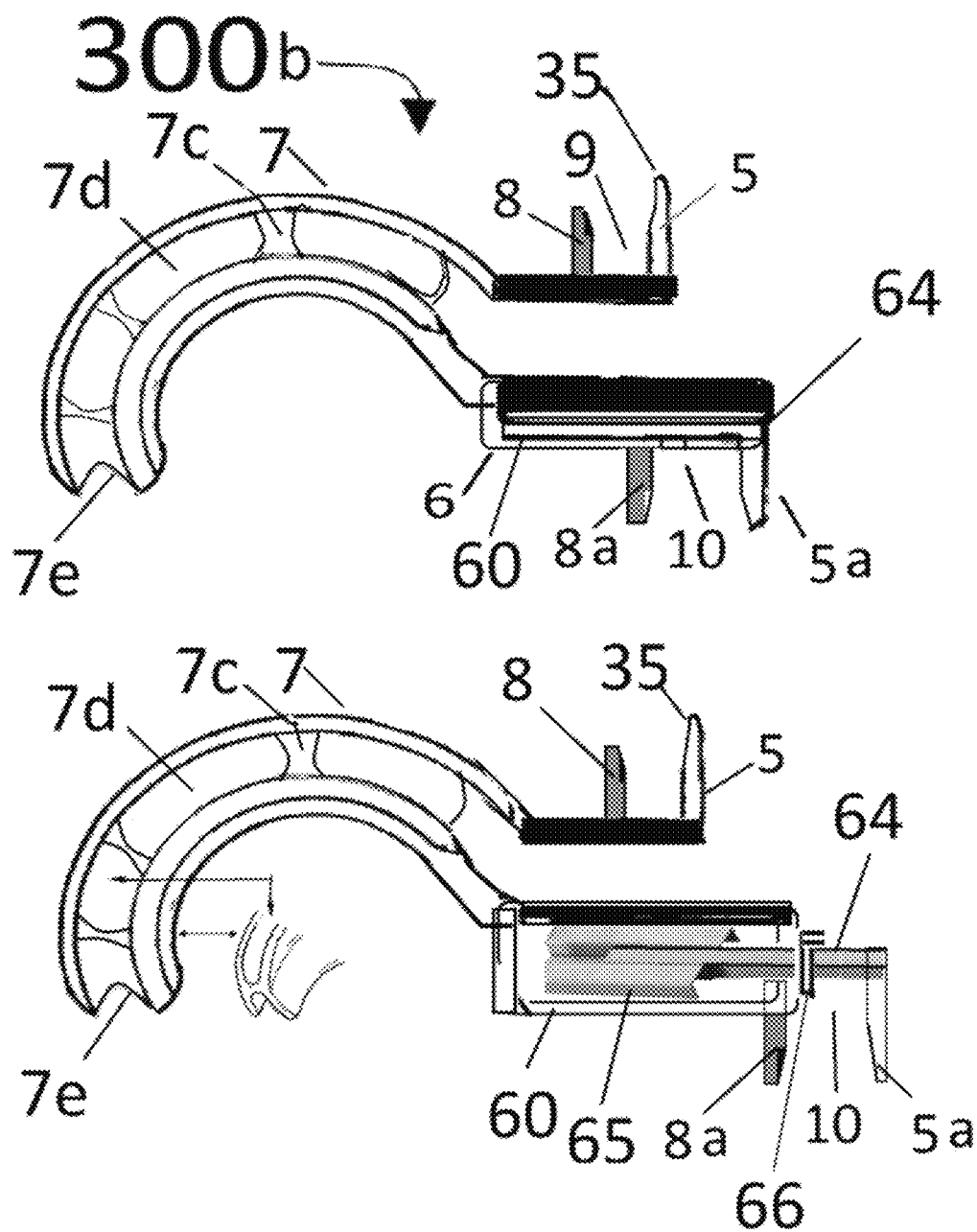
FIG. 3B is a diagram of LJT mandibular protracting oral airway devices having a moving adjustable mandibular flange, according to an embodiment.

FIG. 3B shows a diagram 300b of LJT mandibular protracting oral airway devices 101h and 101i describing how a device with a protracted lower jaw holder prevents the tongue and palate from retracting back to keep the oropharynx airway open. In general, the explanations should be understood to be the same as those of FIGS. 2 and 3 except that the bite block 6 is split into two parts. The lower half 60 of the bite block 6 can be moved forward or backwards from a track 64 on a track 65 with the mandibular teeth receptacles to fit and adjust the length of its movement to fit any mouth size and any degree of mandible protraction. In general, the distance between the maxillary incisors and the incisors of the fully protracted mandible can be between one third of an inch to almost one inch. Some people can protrude their jaw even farther. After placing the incisors in the receptacle or depression on surface 10, the oral airway device 101 is inserted, and the mandibular lower half 60 is protracted to the maximum, so as to have the maximum protraction with tongue pulled away on the moving track 64 to prevent blocking the oropharynx airway with free movement of air without obstruction. Once the mandibular retractor is pulled, it is held in place with a clip restrainer 66. This keeps the oral airway open with lower jaw fully protracted to the maximum.

During the time an airway is in place in the oral cavity, mucous, saliva and other body fluids incline to accumulate in the oral cavity. Guedel type airways having a tube tend to be occluded on both sides. On the other hand, the Berman type airway has a central rib that also prevents the suction of secretions on both sides. This central ridge also prevents an adequate air flow communication. Hence, the LJT mandibular protracting oral airway devices 101h and 101i are provided with openings 7d for communication between the right and left channel through the central rib 7n, and holes or a slit in the Guedel type airway as shown in the FIGS. 2, 2B, and 3C, for example.

Figure 3C:
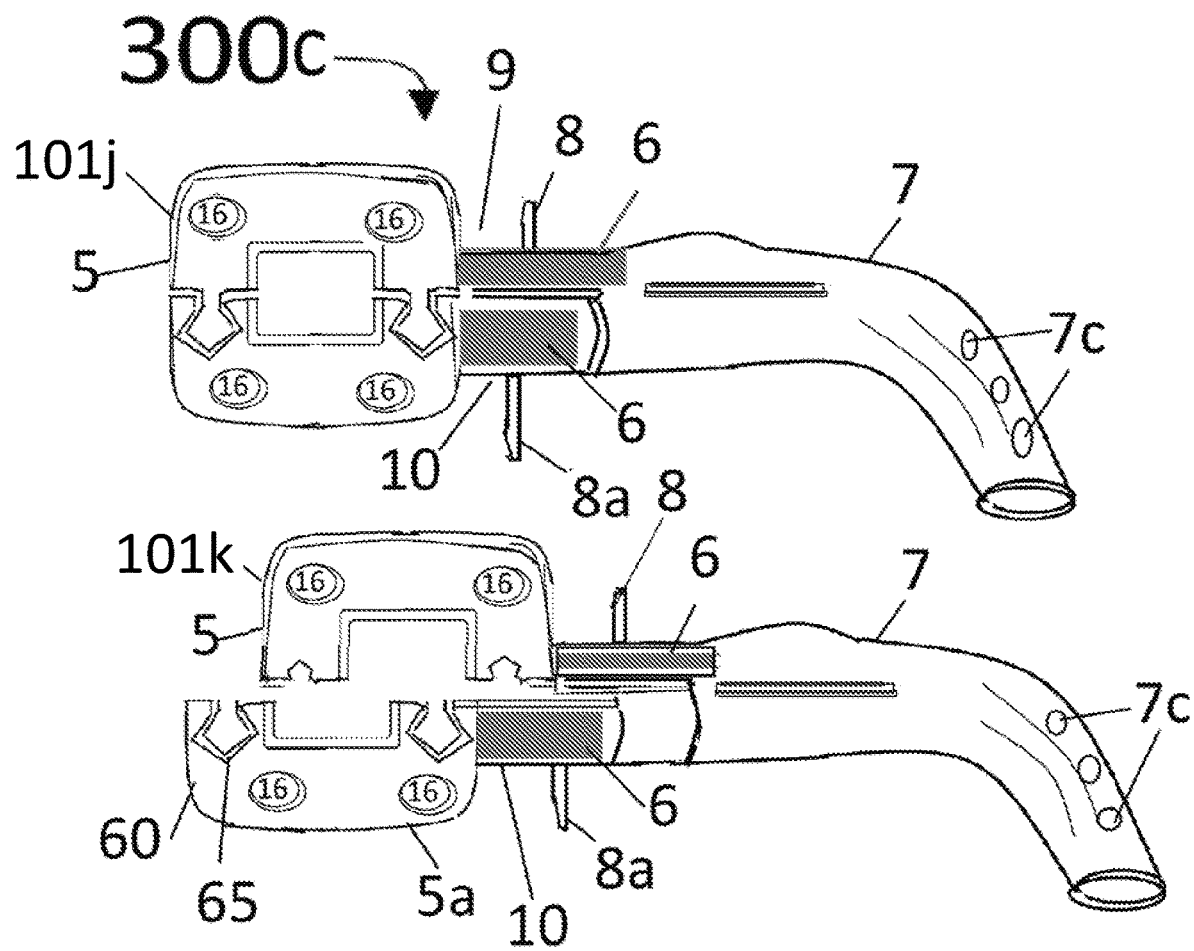
FIG. 3C is a diagram of LJT mandibular protracting oral airway devices having a moving adjustable mandibular protracting flange, according to an embodiment.

FIG. 3C shows a diagram 300c of LJT mandibular protracting oral airway devices 101j and 101k, respectively, for preventing a patient's tongue and palate from blocking the oropharynx airway. The explanations should generally be understood to be the same as those for FIGS. 2 and 3, except that the bite block 6 is split into two parts. The lower half 60 of the bite block 6 can be moved forward on a track 65 incorporated in the bite block 6 of the oral airway device having a flange 5. The flange 5 of the mouth guard with the mandibular teeth receptacles 8a can fit and adjust the length of its movement of the jaw to fit any protrusion length of the lower jaw and to fit any degree of mandibular protraction.

Figure 3D:
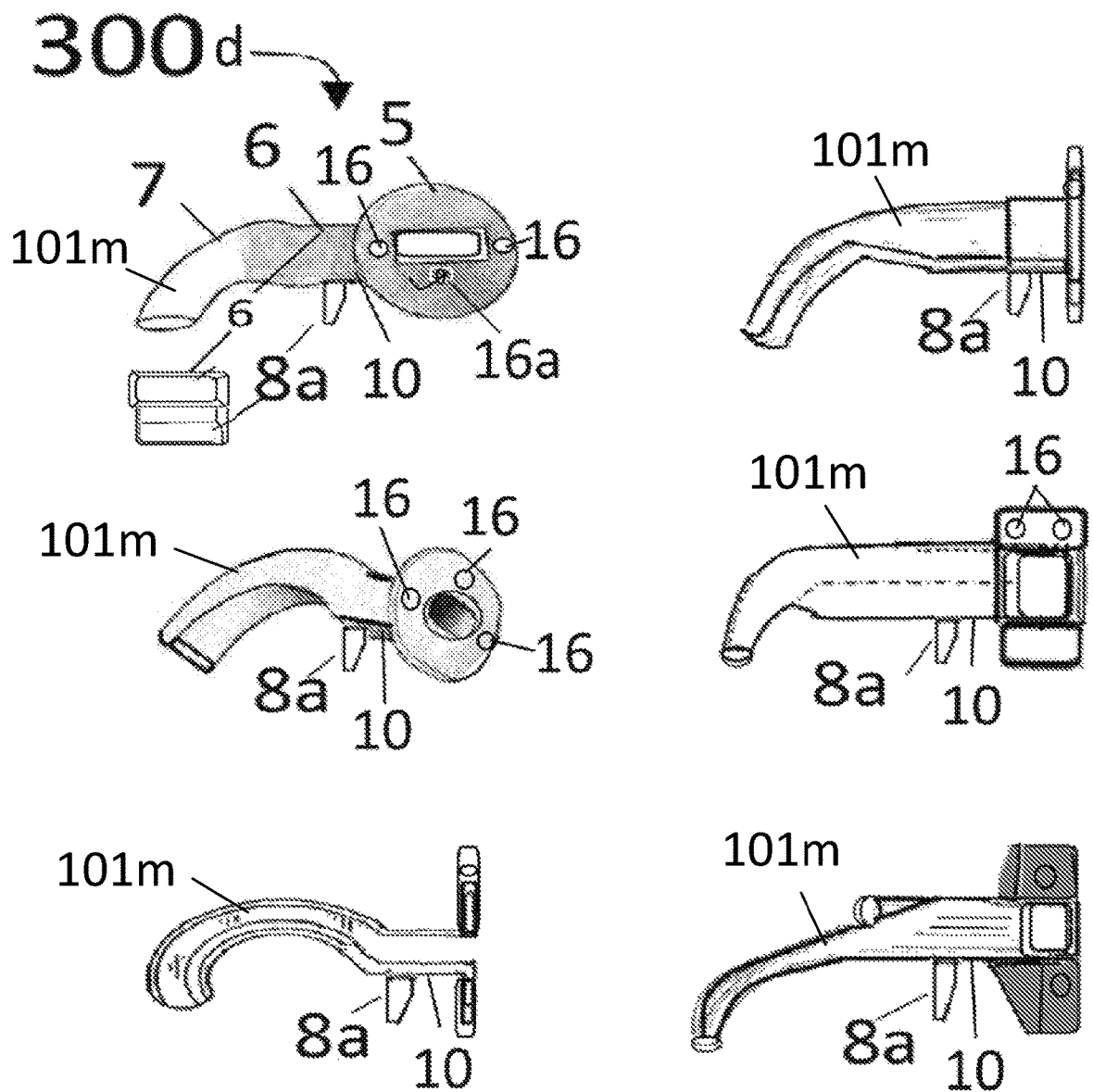
FIG. 3D is a diagram of many types of LJT mandibular protracting oral airway devices, with various configurations, each including a mandibular protracting flange, according to an embodiment.

FIG. 3D shows the diagram 300d with many types of modified oral airway devices 101m adapted from some commonly used in various hospitals, emergency centers, and medical clinics. These oral airway devices 101m each have a rigid C-shaped main body 7 connected to a rigid oval bite block 6 of a certain length, after which the airway is attached to a lip flange 5 that remains outside the mouth when inserted and covers both lips in the center of the oral cavity. The presently disclosed LJT mandibular protracting oral airway device 101m has modified these airways and added a mandibular protracted holding flange 8a under the bite block piece 6, a certain distance behind the lip flange 5. The mandibular flange 8a, with a space and surface 10 for mandibular incisor teeth between this mandibular flange 8a and the lip flange 5, acts as a receptacle and receives mandible protracted teeth and the lower lips, holds oral airway device 101m in position. The fixed maxilla and its incisor teeth act as a fulcrum and thus prevent the lower jaw from moving backward once the airway is positioned in the mouth and in the space and on surface 10 behind the flange. Thus, a patient's jaw is thrust forward when using the oral airway device 101m, freeing the hands of the caregiver to attend to care for the unconscious. The mandibular flange 8a is located about ±0.25 to 1.00 inches behind the lower lip flange 5 of these oral airway devices 101m so as to hold the mandible protruded and in position, pulling the jaw as in jaw thrusting to pull the tongue forward to open the oropharyngeal airway during CPR and in the unconscious and semiconscious patients and during any mask ventilation. Embodiments of the oral airway devices 101m can be provided with a round hole 16 to be used with a nasal oxygen delivery tube with a hook 16a to hold it in position and can also be used also to introduce suction catheter to remove secretions of the oral cavity, regurgitates, keep the tongue wet, introduce NG tube and deliver therapeutic agents or deliver the irrigate fluid.

Figure 3E:
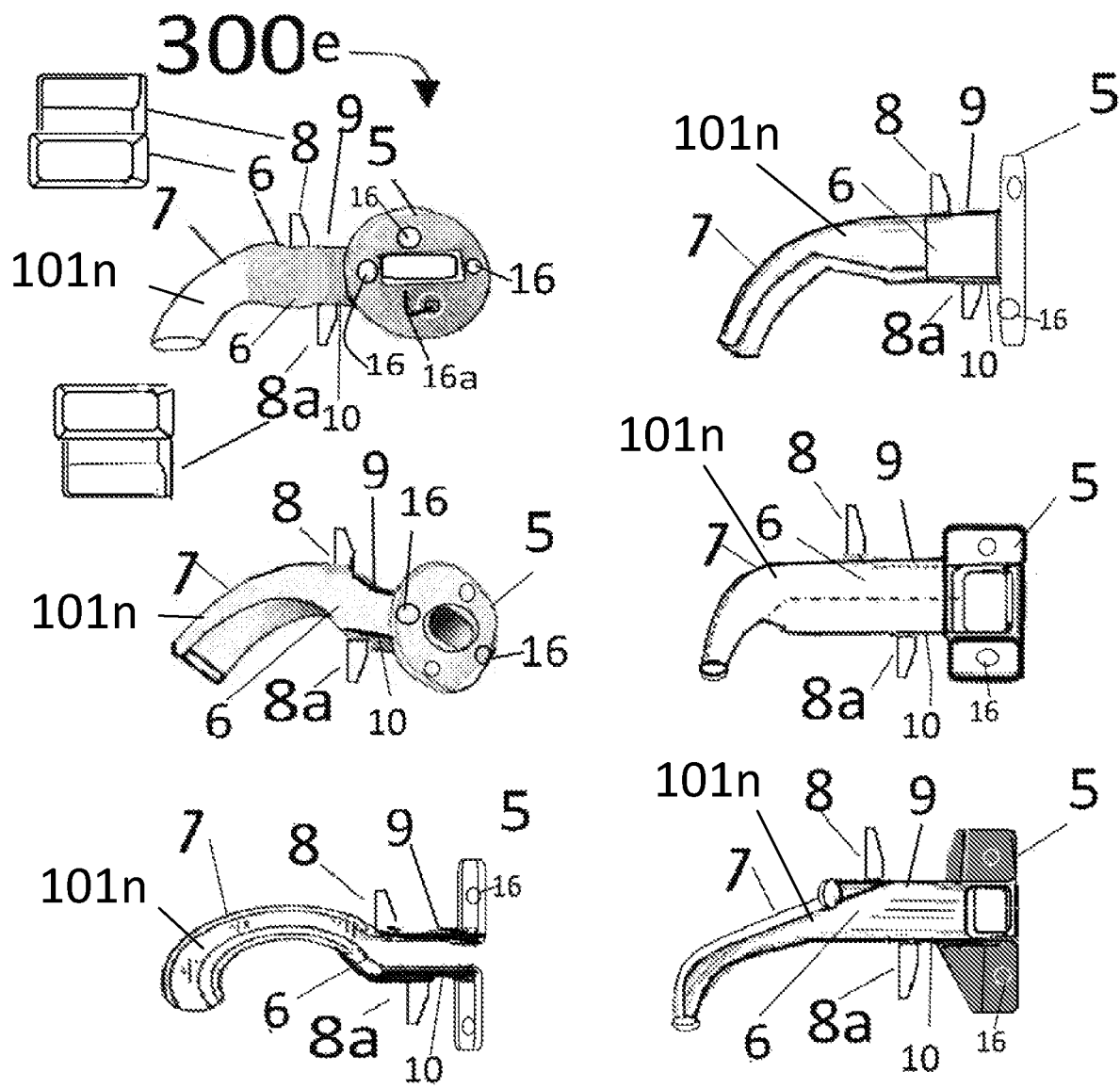
FIG. 3E is a diagram of many types of LJT mandibular protracting oral airway devices, with various configurations, each including a mandibular protracting flange and a maxillary flange, according to an embodiment.
Figure 3F:
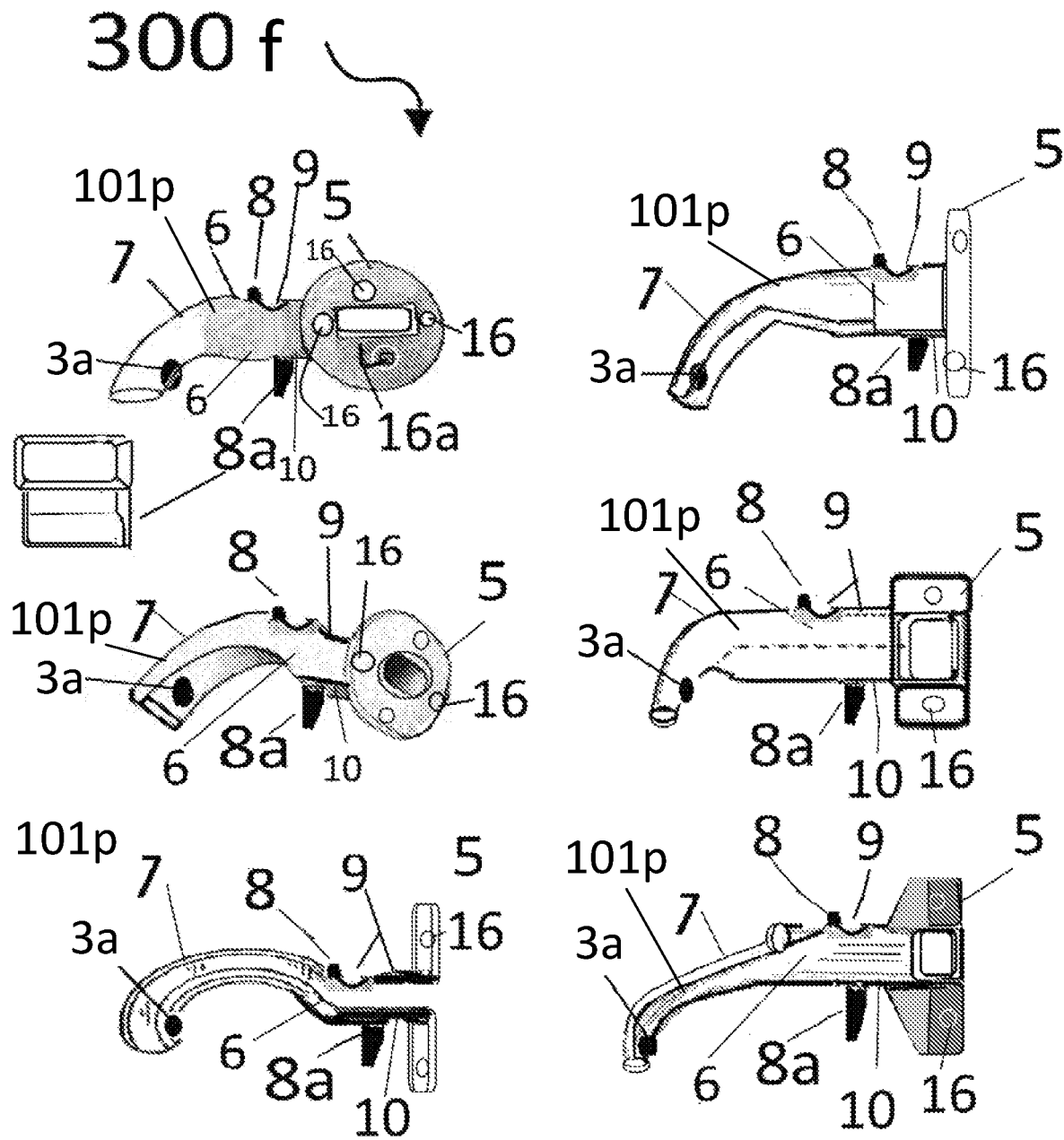
FIG. 3F is a diagram of many types of LJT mandibular protracting oral airway devices, with various configurations, each including a mandibular protracting flange and a maxillary flange, according to an embodiment.

FIGS. 3E and 3F show the diagrams 300e and 300f with many types of modified oral airway devices 101n and 101p adapted from some commonly used in various hospitals, emergency centers, and medical clinics. There are many modifications made, but each oral airway device 101n and 101p has a rigid C-shaped main body 7 connected to rigid oval bite block 6 of the mouthpiece portion of certain length. Attached to the bite block 6 is a flange 5 that is located outside a patient's mouth when inserted and which covers both lips in the center of oral cavity. The LJT mandibular protracting oral airway devices 101n, are generally modified airway devices that add a protracting mandibular flange 8a under the bite block 6, a certain distance behind the lip flange 5. The mandible flange 8a is a protruder/thruster holder and has a space and surface 10 for mandibular incisor teeth between this mandibular post of flange 8a and lip flange 5. The space and surface 10 that acts as receptacle and receives mandible protracted teeth and the lower lips. Thus, the jaw is thrust forward using the oral airway devices 101n, freeing the hands of the caregiver to care for the unconscious. The mandible thruster 8a is located about ±0.25 to 1.00 inches at the level of the upper lip flange 5 of this airway so as to hold the mandible protruded and held in position pulling the jaw in position as we do jaw thrusting to pull the tongue forward to open the oropharyngeal airway. In addition to the above embodiments, these airways are provided with a maxillary flange 8 as a post situated at the top of the bite block 6 of the mouth piece. The maxillary flange is a selected distance behind the flange 5, creating a space and surface 9 for receiving the maxillary incisors which acts as a fulcrum to hold the mandibular protracting jaw thrusting in position with this oral airway device and the upper lip. The maxillary flange 8 is farther from the lip flange 5 compared to mandibular post 8a, so that this flange 8 also acts as a fulcrum to hold the lower jaw protracted. Note these flanges 8 and 8a are slanted anteriorly to accommodate anatomic slanting of the upper and lower jaws with incisor teeth without any pressure trauma to these anatomical parts being restrained. The flange 5 is provided with round holes 16 to be used for a nasal oxygen delivery tube with a hook 16a to hold it in position. The holes 16 can also be used to introduce a suction catheter to remove secretions of the oral cavity, keep the tongue wet, introduce NG tube and deliver therapeutic agents (to treat oral afflictions as well as treat halitosis) as described below as well as facilitate introductions of scopes.

Explanations of the oral airway device 101n of FIG. 3E should be understood to apply and correspond to the oral airway devices 101p of FIG. 3F, except that the maxillary flange 8 shown in FIG. 3E is a maxillary nub with a depression surface 9 in front to hold the incisor teeth firmly in place, that also acts as a fulcrum. The ventral plate of the oral airway device is provided with a slight oval elevation 3a which will prevent the root of the tongue falling back on the epiglottis and posterior pharyngeal wall, thus keeping the oropharynx and laryngopharynx open for unobstructed airflow from lips, mouth, oropharynx and laryngeal passage, then to tracheobronchial passage to lung alveoli. It is noted that distal the wall tip, adapted to fit into the vallecular space described just in front of the epiglottis, is not anatomically correct to open up the laryngo oropharynx. Any slight movement of the tongue with laxed genioglossus muscle and mandible movement backwards will push the epiglottis backwards and downwards to shut down the laryngo pharyngeal air passage resulting in obstruction to the air passage. For this reason, an oval elevation 3a is located just above the ventral tip of the oral airway device 101p, away from the epiglottic vallecular junction, to prevent such a movement and will not allow the epiglottis to move backward to block the laryngeal airway inlet.

Figure 3G:
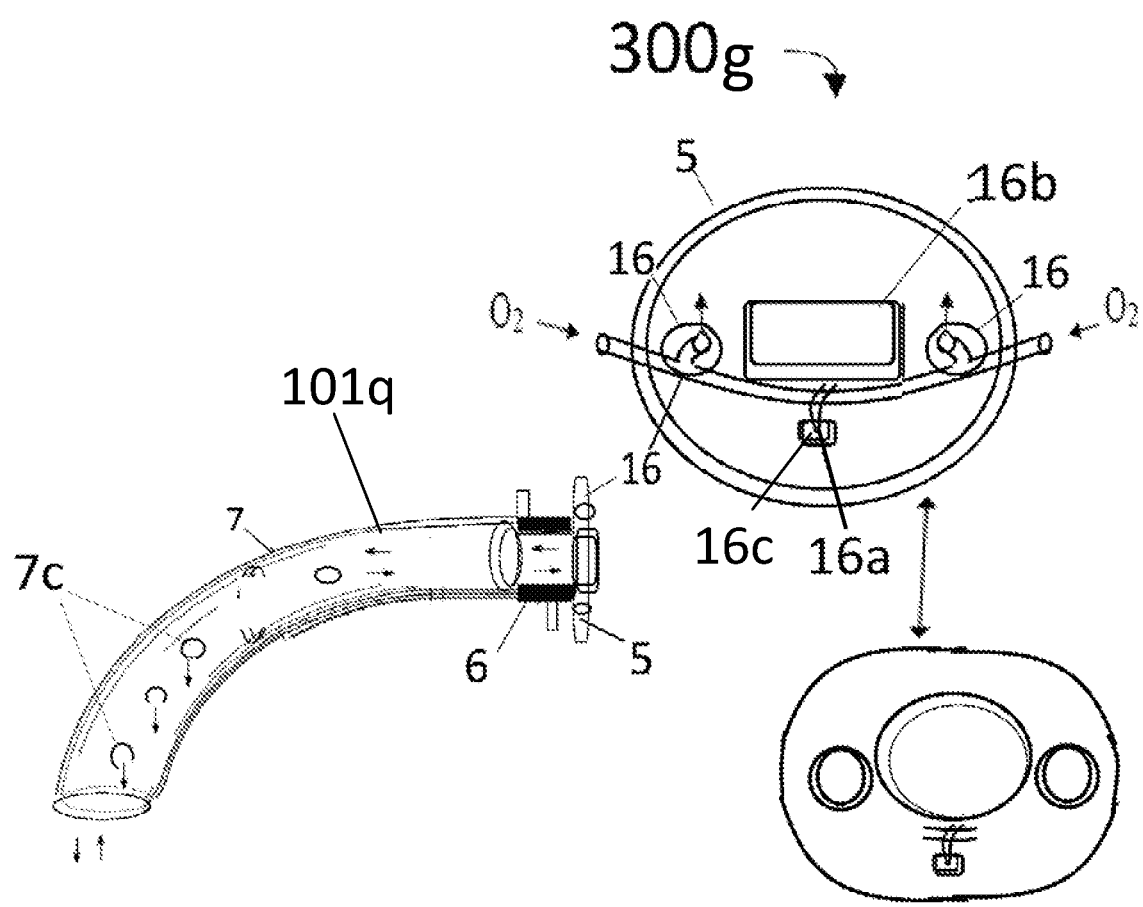
FIG. 3G is a diagram of an LJT mandibular protracting oral airway device having an airway flange with a nasal oxygen delivery cannula attached to a mandibular protracting flange held by a hook on a front lip flange, according to an embodiment.

FIG. 3G shows a diagram 300g of the LJT mandibular protracting oral airway device 101q with lip flange 5. It shows openings/holes/apertures 16 to be used for nasal oxygen delivery tube with a hook 16a, to hold it in position and can also be used to introduce a suction catheter to remove secretions of the oral cavity, keep the tongue wet, introduce an NG tube and deliver therapeutic agents or irrigate the oral cavity. These openings 16 surround the air entry and exit orifices 16b, which can be used to monitor end tidal carbon dioxide. The oxygen can be delivered through the nasal cannula and hook 16a as needed. These openings 16, when large enough, can also act as breathing channels adjacent to central airway lumen 16b during use of fiber optic scopes using the central lumen. Main airway size and shape of the lumen in the center of the oral airway is such that it allows the manipulation for inserting and advancing a fiberoptic scope through the proximal end and exiting the scope through the distal end with openings 16 on the side allow for breathing. With some modification, an oxygen sensor can be incorporated as additional embodiment added to or attached to the distal end of the LJT oral airway device 101q. LJT oral airway device 101q is provided with holes 7c on the dorsal plate that communicates with oval holes in the central ridge. This allows for suctioning of the secretions, delivering therapeutic agents, cleaning the mouth with saline besides delivery of oxygen to nasopharynx in case there is obstruction to oropharynx air passage. The double arrow points to the insert that can be different shape than oval.

The prongs of the nasal oxygen delivery catheter are positioned on the delivery holes 16 secured to the lip flange 5 by a hook 16a. When our airway with inserted configuration positioned in the throat of a patient, at least one aperture in the airway tube allows fluid, for example air or medical gas, to pass from and through the nasopharyngeal passage. Positioning at least one aperture 7c near the distal end of the airway tube facilitates the transfer of gas through the naso-pharyngeal air passage.

Use of Guedel type airway can block the nasopharyngeal air passage. The prevention of this nasopharyngeal airway block by using oral airway device 101q, which provides naso-pharyngeal ventilating holes 7c along the mid-lateral position of the airway on one or both sides, replaces the need to use nasal prongs with high flow of oxygen. They are not located in the mid sagittal place, to prevent being obstructed by coming in contact with the soft palate.

Figure 3H:
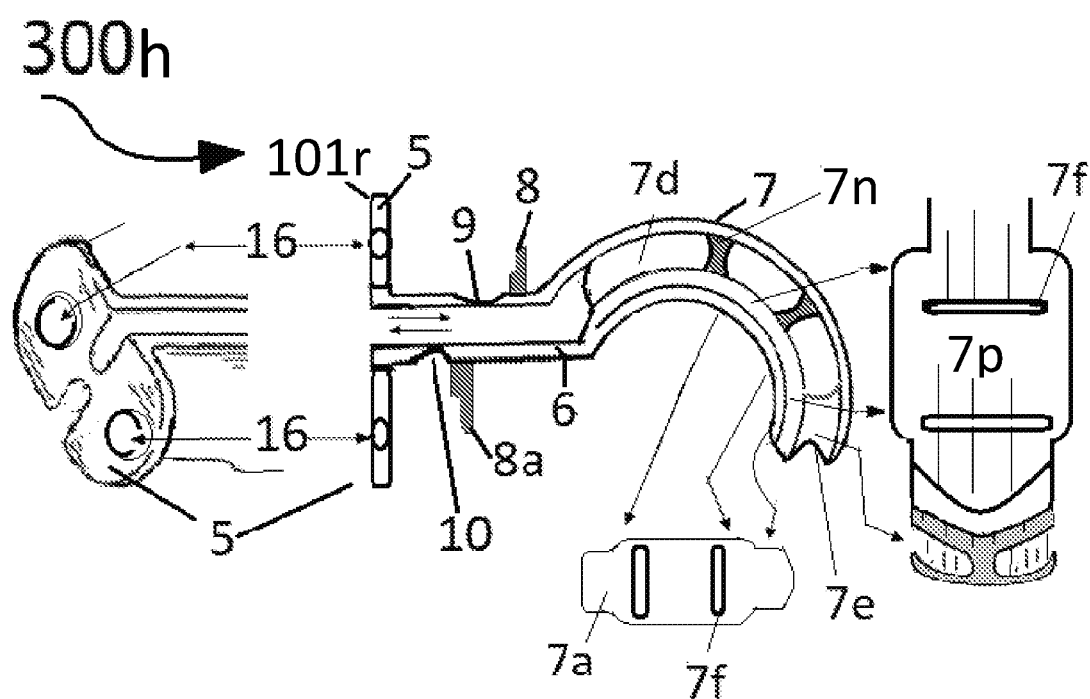
FIG. 3H is a diagram of an LJT mandibular protracting oral airway device having a ventral surface expansion to hold the tongue in place, according to an embodiment.

FIG. 3H is a diagram 300h of a LJT mandibular protracting oral airway device 101r showing the oral airway device with an expanded ventral surface at the distal end of the ventral plate 7a and 7p of the device expanded only part of it. The Guedel and Berman oral airway devices, as well as other oral airway devices in use, are not wide enough to provide side-to-side support for the tongue of the obese or short people and those with macroglossia and those who suffer from pituitary gland tumors or myxedema. Hence, the oral airway device 101r has added an oval or teardrop shaped thick plastic plate addition, as shown on ventral plates 7a and 7p. Only a distal segment of the ventral surface of Berman or any other airway of similar type is modified in such an embodiment. This ventral plate 7a and 7p extends about 1-2-3-4-5-6 mm beyond the lateral surface of the oral airway. The ventral plate is provided with horizontal bars or ridges 7f that prevent the tongue moving back with lapse of time. It has the smooth edges of this addition will prevent sliding back of the tongue completely from side to side and prevents its slippage to one or the other side at the same time open the airway to ventilate by mask or breath spontaneously. This plate will provide greater width of the curved lower member of the curved section of the oral airway which will give better support to the tongue laterally, thus increasing the side to side dimension of the airway opening. This addition will not alter the length or the radius of the curve of the airway. This additional embodiment will give better tongue support and therefore a larger opening of the patient's airway to facilitate easier ventilation of the patient. This would be especially helpful in obese patients with large tongues or due to any number of medical conditions. It is also useful for all patients being administered general anesthesia during induction and waking up. In the case of the Berman oral airway device, the ventral distal one third can be widened instead of adding a plate embodiment described. It also shows the round holes of about 5-7 mm located on the lip flange 5 and ventilating holes 16.

FIG. 3H shows a central ridge that is open to both sides providing openings 7d for communication with ventral and dorsal plates supported by rib or pillar 7n for stability. The tip 7e of the airway is flared as shown in the figure. This communication will facilitate the breathing through the nasopharyngeal airway and suctioning of the secretions and regurgitate with ease. The FIG. 3H also shows a maxillary flange 8 and a mandibular flange 8a present to protract the jaw with depression surfaces 9 and 10 on the bite block 6 to accommodate the sharp ends of incisor teeth. The lip flange 5 is provided with round openings 16 connected to a cannula of proper size to be used to deliver therapeutic agents, supplemental oxygen, and for the suction of secretions.

Figure 4:
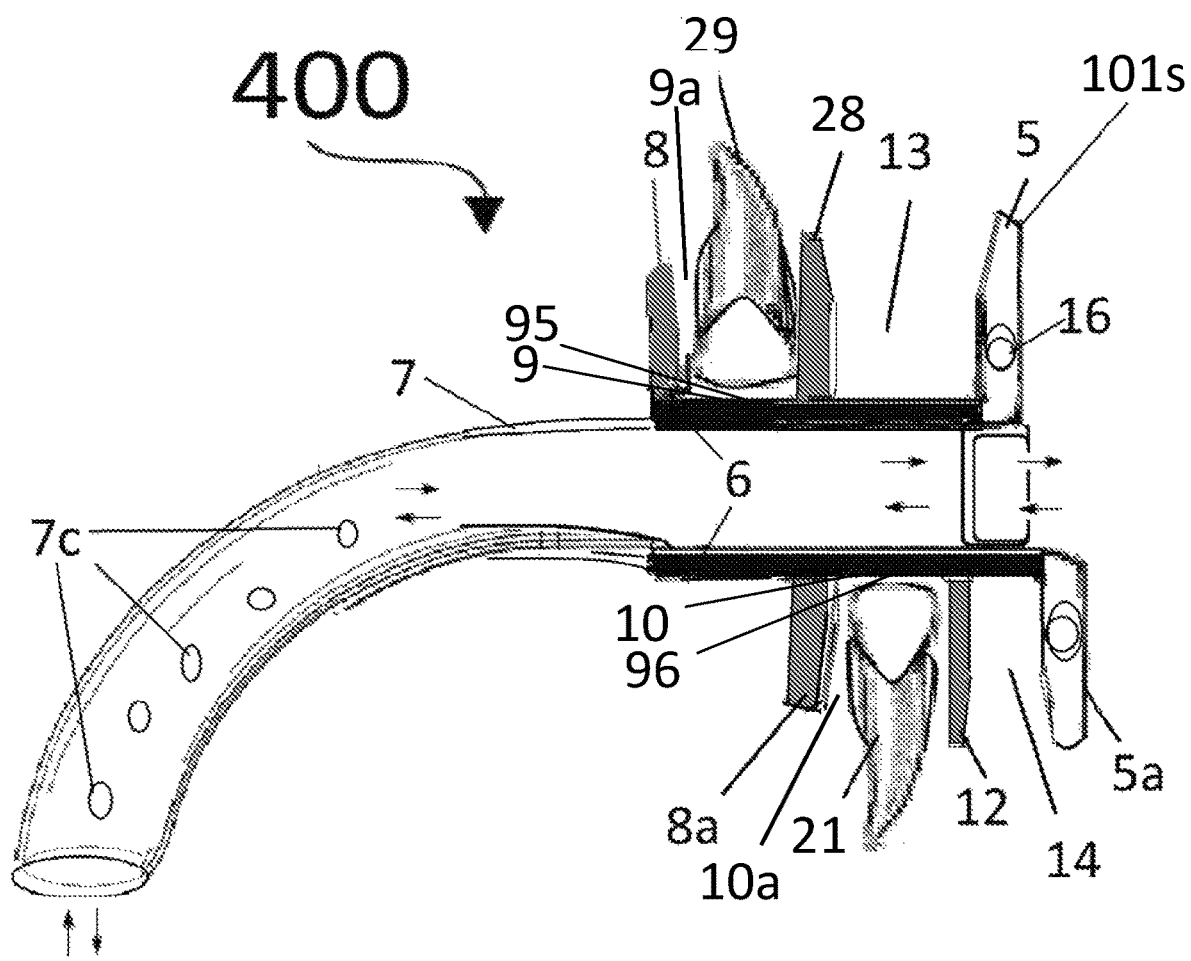
FIG. 4 is a diagram of an LJT mandibular protracting oral airway device showing patient incisor teeth in front of maxillary and mandibular flanges with pockets for patient lips, according to an embodiment.

FIG. 4 shows the diagram 400 of an LJT mandibular protracting oral airway device 101s for preventing a patient's tongue and palate from obstructing the oropharynx air passage using the oral airway curved main body 7. In general, the explanations of FIGS. 2 and 3 should be understood to apply to FIG. 4 as well. This LJT oral airway device 101s has a rigid main body 7, and a bite block 6 mouth piece. Bite block 6 is provided with multiple upper and lower projection flanges that, together with lip flanges 5 and 5a, create two isolated pockets behind each of the annular lip flanges 5 and 5a. The first set of maxillary projection flanges 8 and 28 create a pocket 9a for maxillary incisor teeth 29. Forward of the flanges 8 and 28 is a pocket 13 between flange 28 and lip flange 5. Space 13 is the receptacle for a patient's upper lips. The lower surface of the bite block 6 has a set of mandibular flanges 8a and 12 that create a pocket 10a to accommodate incisor teeth 21 of the mandible. The mandibular flange 12 and lower lip flange 5a creates a pocket 14 for a patient's lower lip as well. Accordingly, a patient's retracted lower jaw is held in position due to the position of the maxilla and mandible in their respective recesses or pockets 9a and 10a akin to thrusting of the jaw during CPR and maintaining an oral airway device in an unconscious or semiconscious person.

Certain embodiments, as shown in FIG. 4 for example, can include an LJT mandibular protracting oral airway device 101 wherein the bite block 6 contains a second mandibular flange 12 projecting outwardly from the lower ventral surface 10, the mandibular flange 8a and the second mandibular flange 12 forming a pocket 10a surrounding the second bite location 96 for mandibular incisor engagement. In FIG. 4, the bite block 6 contains a pair of maxillary flanges 8 and 28 outwardly projecting from the upper dorsal surface 9, the pair of maxillary flanges 8 and 28 forming a pocket 9a surrounding the first bite location 95 for maxillary incisor engagement.

Figure 5:
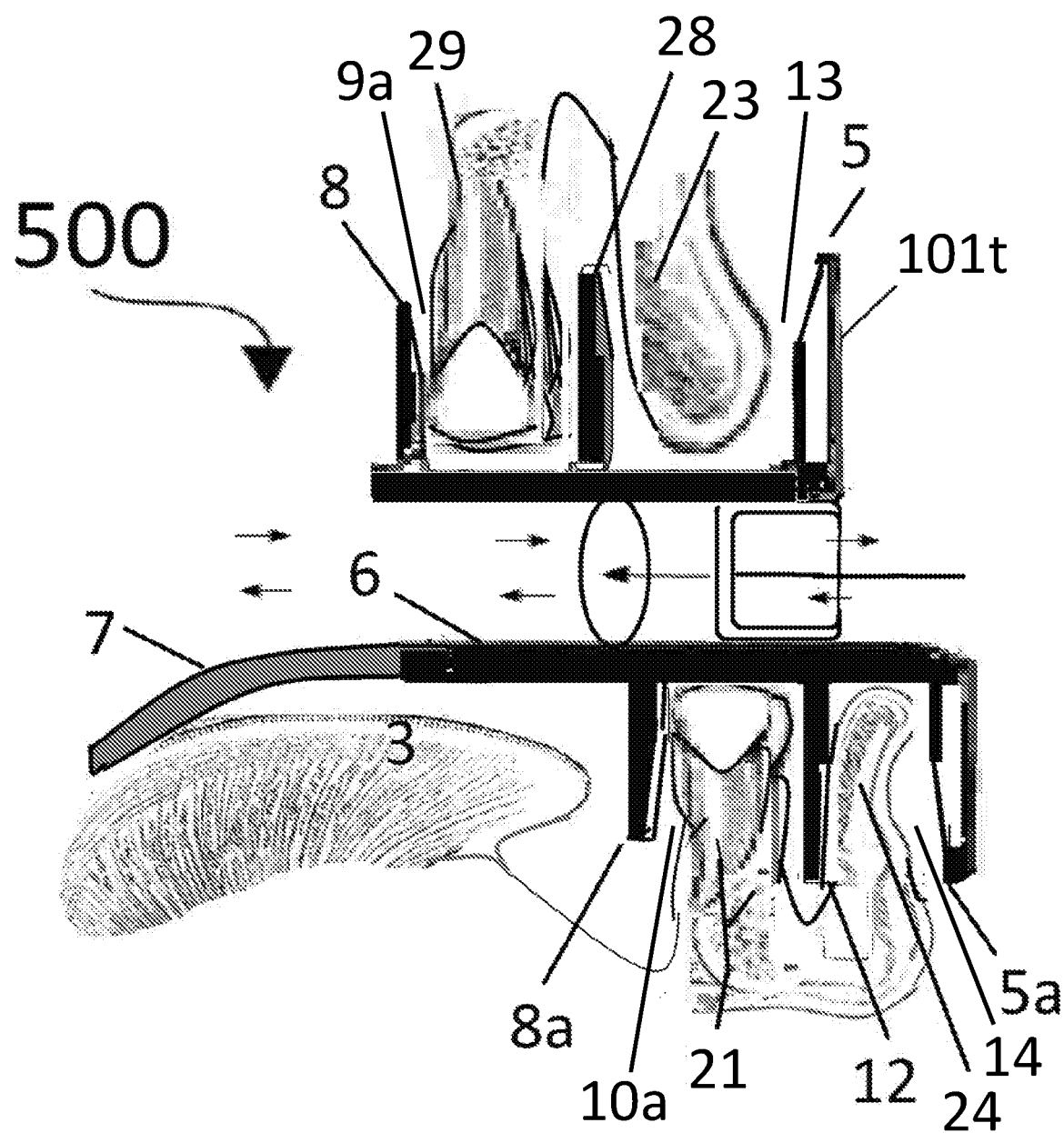
FIG. 5 is a diagram of an LJT mandibular protracting oral airway device showing maxillary and mandibular incisor teeth and lips in their pockets between flanges, according to an embodiment.

FIG. 5 shows a diagram 500 of a LJT mandibular protracting oral airway device 101t in the mouth of a patient to help explain how the tongue and palate are prevented from obstructing the patient's airway using the LJT oral airway device 101t and curved main body 7. Explanations of the LJT oral airway device 101 associated with prior figures should be understood to apply and correspond to the oral airway devices 101t of FIG. 5 as well. This oral airway device 101t has a rigid body 7 and a bite block 6.

Bite block 6 is provided with multiple upper and lower projection flanges that, together with lip flanges 5 and 5a, create two isolated pockets behind each of the annular lip flanges 5 and 5a. The first set of maxillary projection flanges 8 and 28 create a pocket 9a for maxillary incisor teeth 29. Forward of the flanges 8 and 28 is a pocket 13 between flange 28 and lip flange 5. Pocket 13 is the receptacle for a patient's upper lips. The lower surface of the bite block 6 has a set of mandibular flanges 8a and 12 that create a pocket 10a to accommodate incisor teeth 21 of the mandible. The mandibular flange 12 and lower lip flange 5a creates a pocket 14 for a patient's lower lip as well. This diagram shows the patient's maxillary teeth 29 and upper lip 23, and the patient's mandibular incisor teeth 21 and lower lip 24 in their respective pockets. Thus, the retracted lower jaw is held in position due to the position of the maxilla and mandible in their respective pocket recesses.

Figure 6:
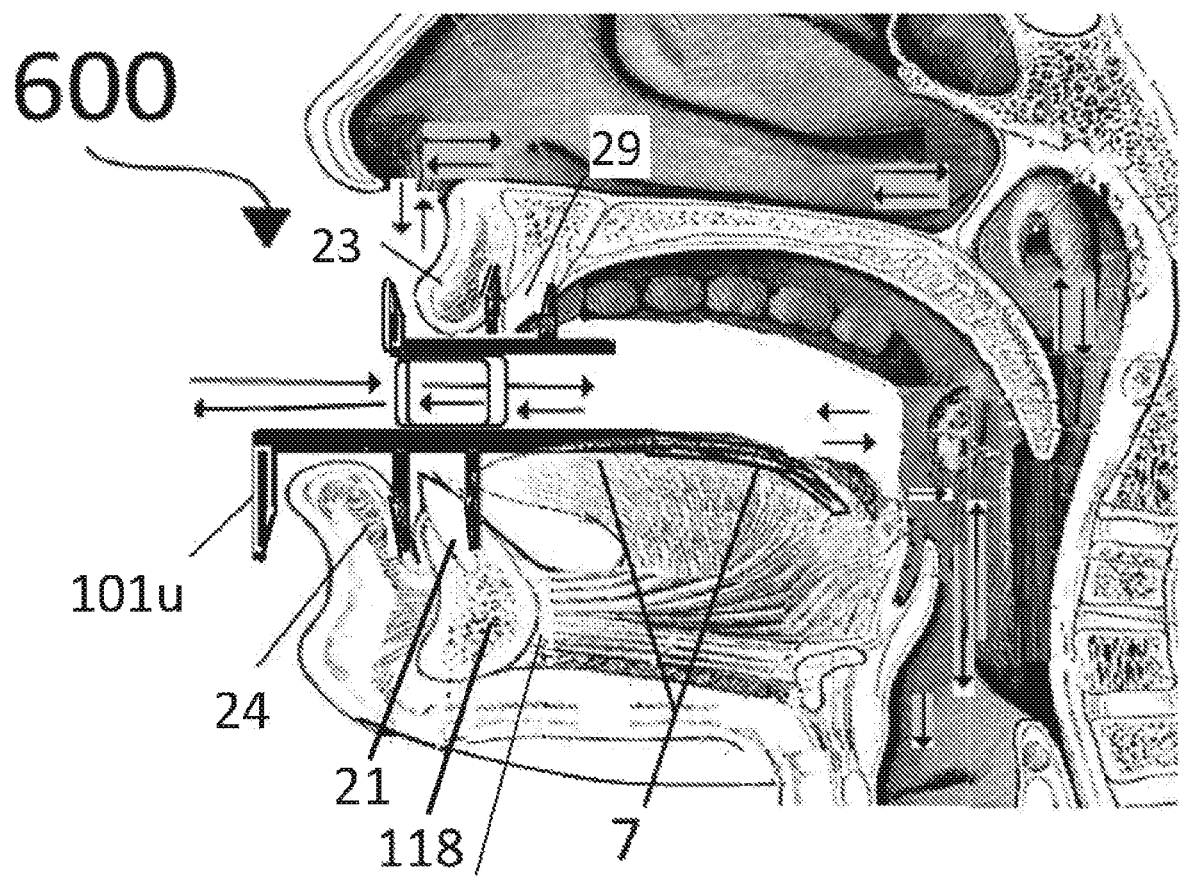
FIG. 6 is a diagram showing an LJT mandibular protracting oral airway device in a patient's mouth, according to an embodiment.

FIG. 6 shows a diagram 600 of a LJT mandibular protracting oral airway device 101u in a patient's mouth, showing how the tongue and palate are prevented from blocking the oropharynx air passage by a curved main body 7. Diagram 600 shows how the incisor teeth 29 and 21 of the maxilla and the mandible are located in their respective pockets. Further, upper lip 23 and lower lip 24 are located properly in their respective pockets in this LJT oral airway device 101u. The arrows point to the direction of the airflow to the respiratory system without the obstruction of the tongue and palate. The retracted lower jaw 118 is held in position due to the fixed position of the maxilla and the protracted mandible features in their respective recesses. Accordingly, the upper and lower lips 23 and 24 also help prevent movement backwards that could block the oropharyngeal passage. It is noted that the mandibular flanges can be located about ±0.25 to 1 inch in front of the maxillary flanges and can be located in front of the upper lip flange.

Figure 7:
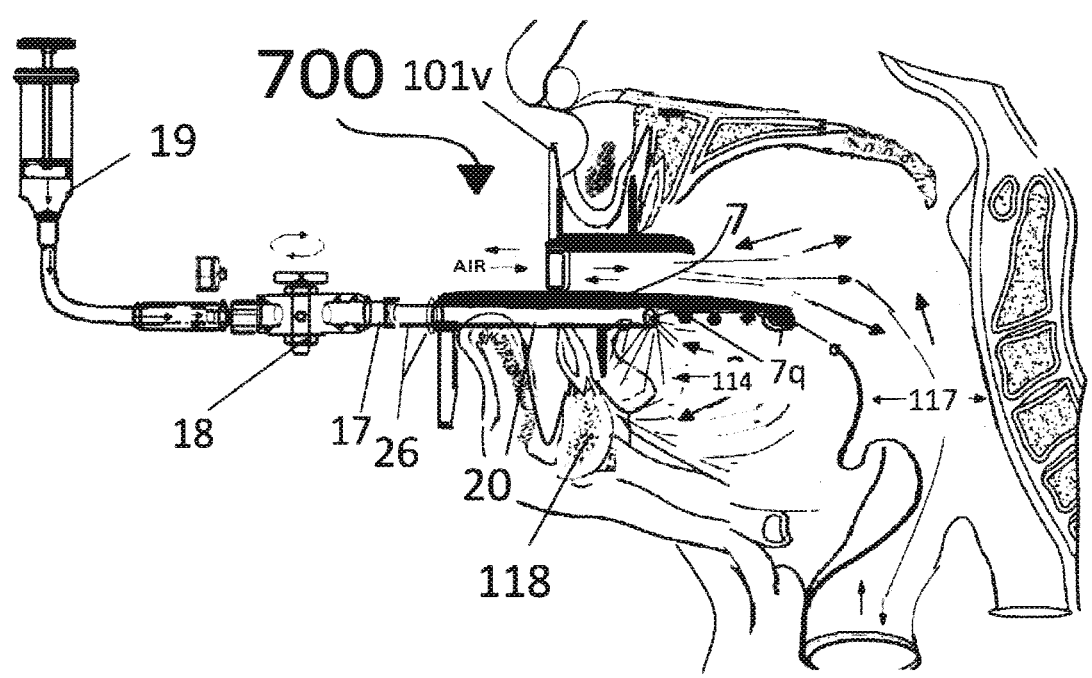
FIG. 7 is a diagram showing an LJT mandibular protracting oral airway device in position to deliver therapeutic agents to treat an oral affliction and halitosis, according to an embodiment.

FIG. 7 shows a diagram 700 including an LJT mandibular protracting oral airway device 101v in a patient's mouth showing how it prevents the tongue 114 and palate from coming in contact and moving on the oropharynx air passage 117 so as not to cause respiratory distress in unconscious and semiconscious patients that can be a serious health hazard if not corrected due to obstruction to airflow. Under the curved tongue retractors main body 7 or tongue restrainers there are microscopic projections or tiny suction cups 7q holding the tongue's dorsal surface and preventing its movement backwards during unconsciousness. Arrows are shown pointing to the direction of air moment in the oropharyngeal cavity. The explanation of this figure is generally corresponds with that of FIGS. 5 and 6. The openings on the flange 26 are fitted with delivery connector 20 which is in turn connected to syringe 19 through a three-way stopcock 18 connected to connector 17 to deliver therapeutic agents under the tongue to increase the tone of the genioglossus.

Figure 8:
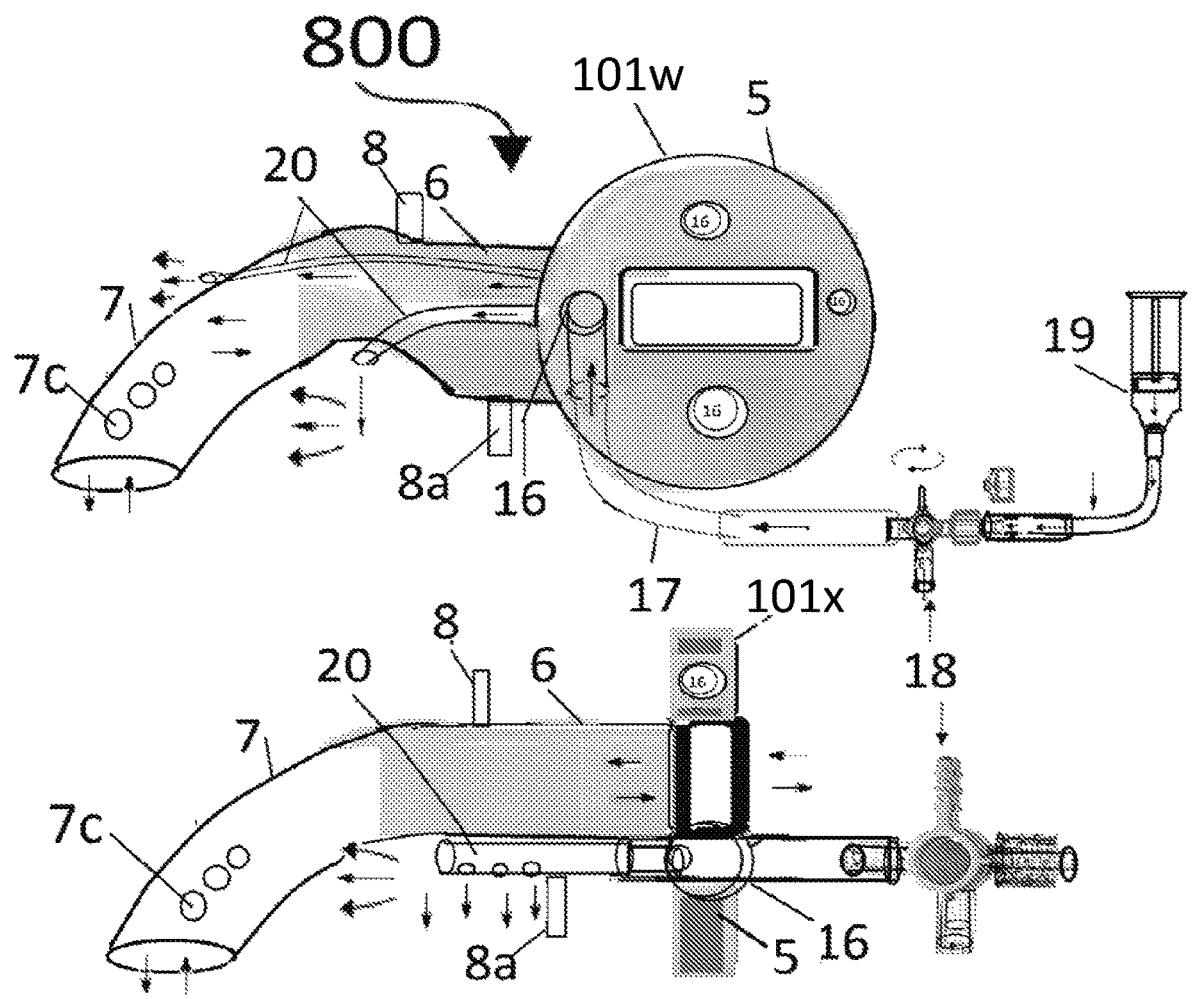
FIG. 8 is a diagram showing an LJT mandibular protracting oral airway device with a therapeutic agent delivery and suction catheter inserted through the opening in a flange to deliver therapeutic agents to treat oral afflictions or keep the mouth and tongue wet, according to an embodiment.

FIG. 8 shows a diagram 800 including embodiments of LJT mandibular protracting oral airway devices 101w and 101x for preventing patient's tongue and palate from obstructing the patient's oropharynx airway. The LJT oral airway devices 101w and 101x have a rigid main body 7 that comes in contact with the tongue and which is continuous with a bite block 6. Bite block 6 is a mouthpiece that is attached to a lip flange 5 which has ovals or rectangular aperture for air entry and exit venting. The flange 5 resides outside a patient's lips and helps to hold the oral airway device 101w or 101x in the mouth and prevents its movement into the patient's oral cavity. These LJT oral airway devices 101w and 101x, unlike others, are provided with a luer lock adapter or delivery tube or suction catheter or accesses to oral cavity through opening (outlet/orifice/vent passage orifice/conduit outlet) 16 on any side of the flange 5 adjacent to the air vent. The back of the tube adapter coming out of the orifice is provided with extension tubing 20 running along the bite block 6 to the middle of the rigid body. The external opening is attached to extension tubing 17 which is connected to three-way stopcock 18 and a syringe 19. These embodiments of an LJT oral airway device 101w and 101x are used to keep the tongue wet, to deliver therapeutic agents to the mouth, to deliver therapeutic agents to increase the tone of the genioglossus muscle, to wash the mouth, and to suction the mouth secretions in those who are intubated for days and weeks. The opening(s) 16 in the front flange are used for nasal catheter oxygen delivery also.

Figure 9:
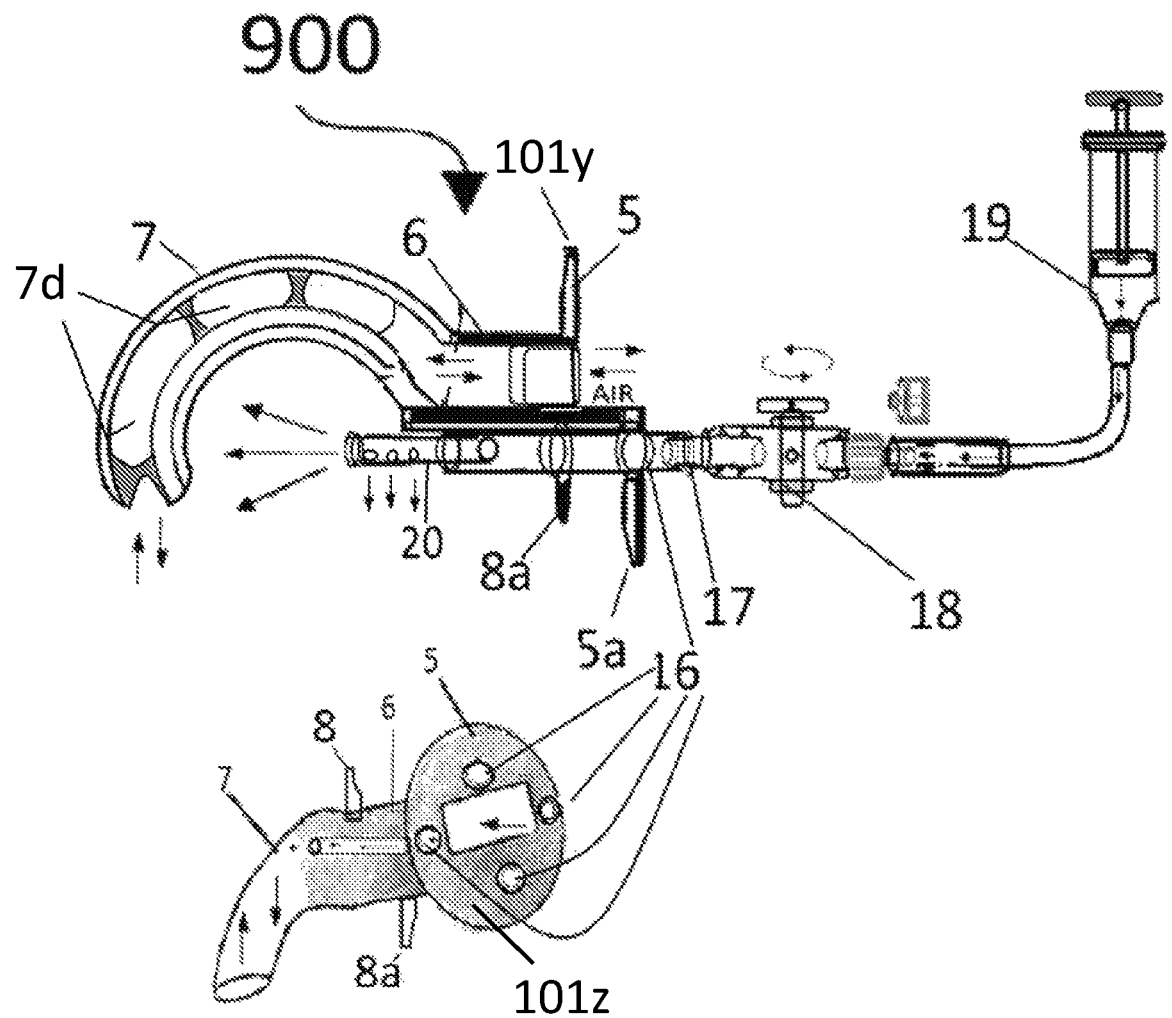
FIG. 9 is a diagram showing an LJT mandibular protracting oral airway device with bite block embodiments and a bite block holder, according to an embodiment.

FIG. 9 shows a diagram 900 including embodiments of LJT mandibular protracting oral airway devices 101y and 101z. These oral airway devices 101y and 101z, unlike others, are provided with a luer lock adapter or delivery tube or suction catheter or accesses to oral cavity through opening (outlet/orifice/vent passage orifice/conduit outlet) 16 on any side of the flange 5 adjacent to the air vent opening. The back of the tube adapter coming out of the orifice is provided with extension tubing 20 running along the bite block part to the middle of the rigid body. The external opening is attached to extension tubing 17 connected to a three-way stopcock 18 and to a syringe 19. These embodiments in the oral airway are used to keep the tongue wet, and to deliver therapeutic agents to the mouth, wash the mouth and suction the mouth secretions in those who are intubated for days and weeks. Therapeutic agents to increase the tone of the genioglossus muscle can be delivered through the tubing 20, directly delivered to sublingual space under the behind the mandibular incisor teeth. The opening 16 in the front flange is used for nasal catheter oxygen delivery also. Note that the median ridge of the Berman type airway is provided with openings 7d that communicate on both sides.

Figure 10:
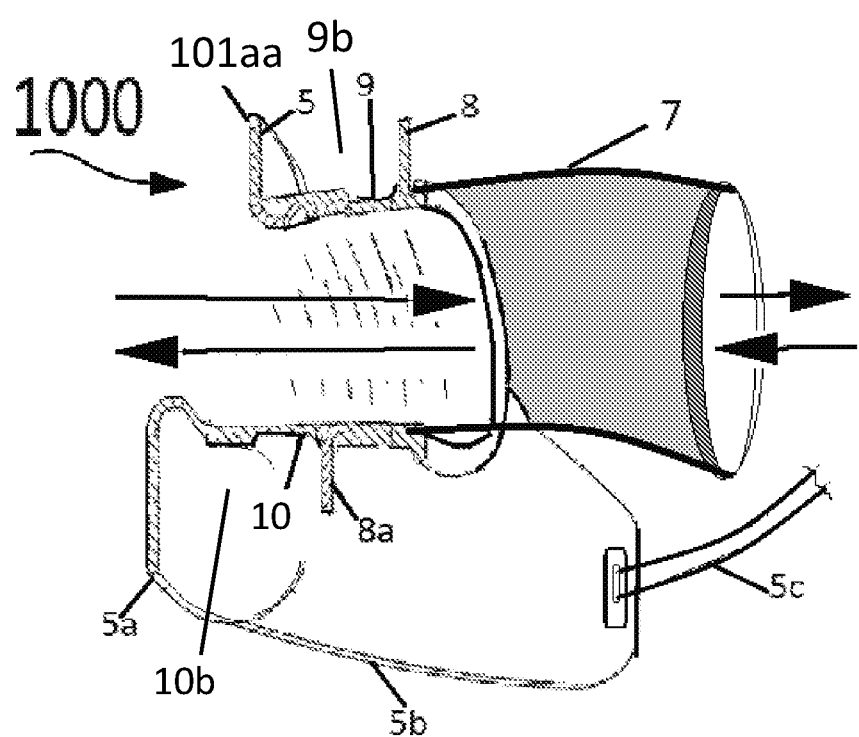
FIG. 10 is a diagram showing an LJT mandibular protracting oral airway device with a strap binding through the mouth flange, according to an embodiment.

FIG. 10 shows a diagram 1000 including an LJT mandibular protracting oral airway device 101aa including a bite block. The diagram 1000 shows that the bite block can be expanded posteriorly to form a short oral body 7 to guide air and fiberoptic devices. In this arrangement, incisor teeth of the maxilla and the mandible are located in their respective pockets 9b and 10b and up against surfaces 9 and 10, respectively. The upper lip and the lower lip are also located in the same respective pockets 9b and 10b. The arrows point to the direction of the airflow to the respiratory system without the obstruction of the tongue and palate. The semi-retracted lower jaw is held in position due to the fixed position of the maxilla flange 8 with respect to a depression surface 9 in the bite block. Further, a protracted mandible flange 8a with incisor teeth are located in a depression surface 11 in front of the mandibular flange 8a. Pocket 10b accommodates the lower lip also. Note that the location of the mandibular flange 8a can be about one quarter of an inch to one inch in front of the maxillary flange 8 in some embodiments. Other embodiments can have different spacing for these flanges. The mandibular flange 8a can also be placed further in front of upper lip flange 5, thus keeping the lower jaw pulled farther forwards to facilitate breathing and for passing any fiberoptic device. The LJT oral airway device 101aa is provided with plastic anchor patch 5b which extends from the lip flange 5 and 5a laterally with a hole and tape 5c to hold the oral airway in position without being spit out as the patient becomes conscious and are breathing on their own. One of the important functions of this bite block is to prevent biting the tongue and maintaining an air passage without the tongue falling back so as not to cause an obstruction.

Figures 11A, 11B:
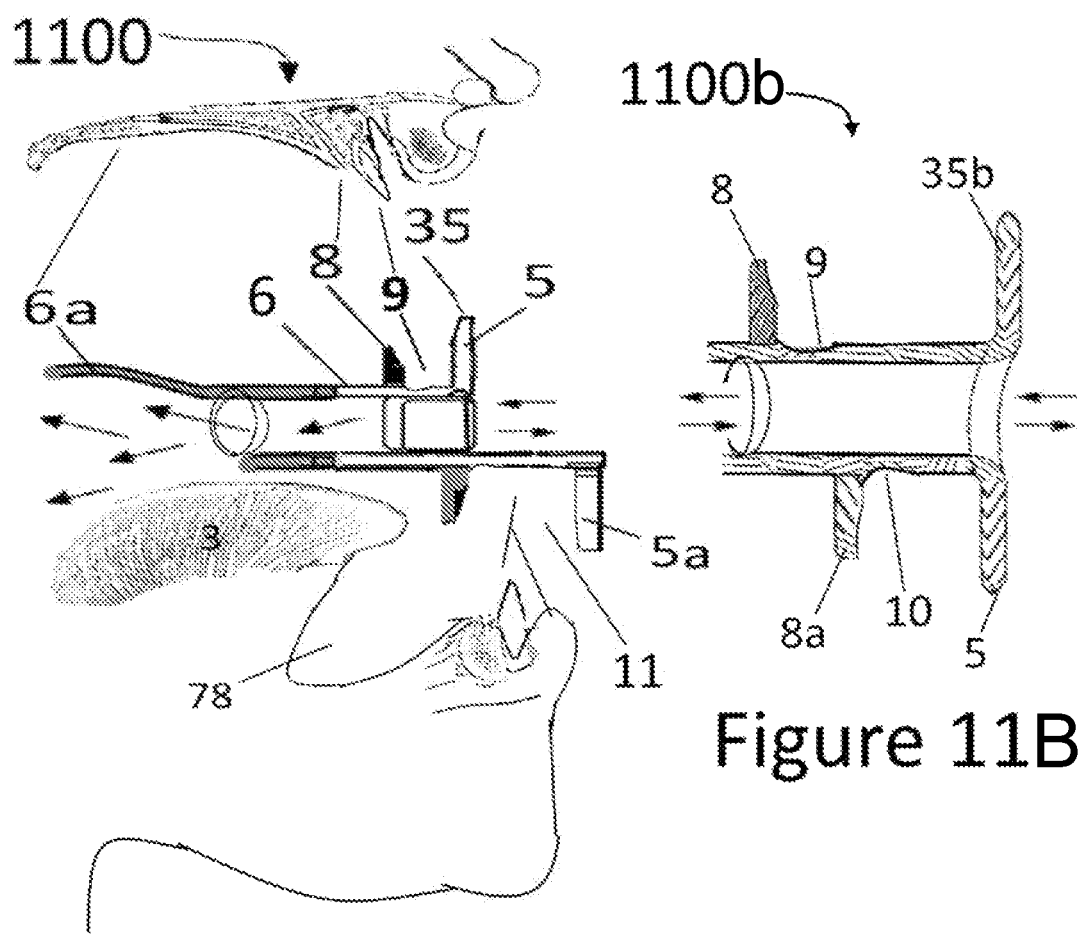
FIGS. 11A and 11B are diagrams showing LJT mandibular protracting oral airway devices used to keep the mouth open and keep the mandible protracted as a bite block, according to an embodiment.
Figure 12B:
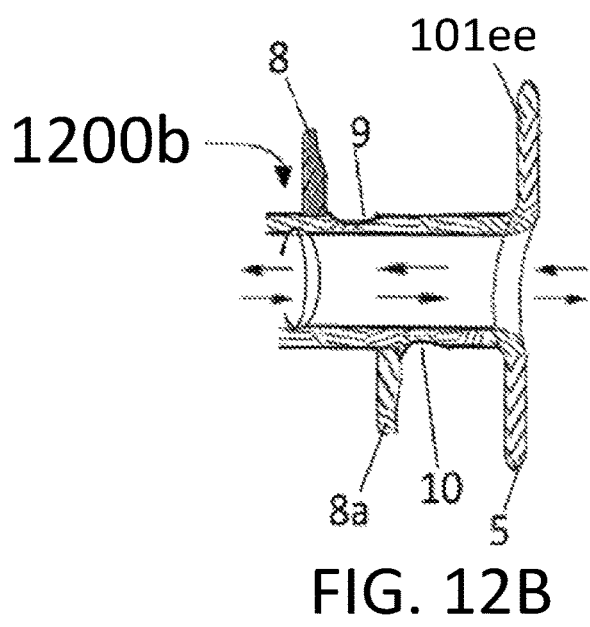
FIG. 12A-C are diagrams showing LJT mandibular protracting oral airway devices for intubation with fiberoptic scopes, according to an embodiment.
Figure 12C:
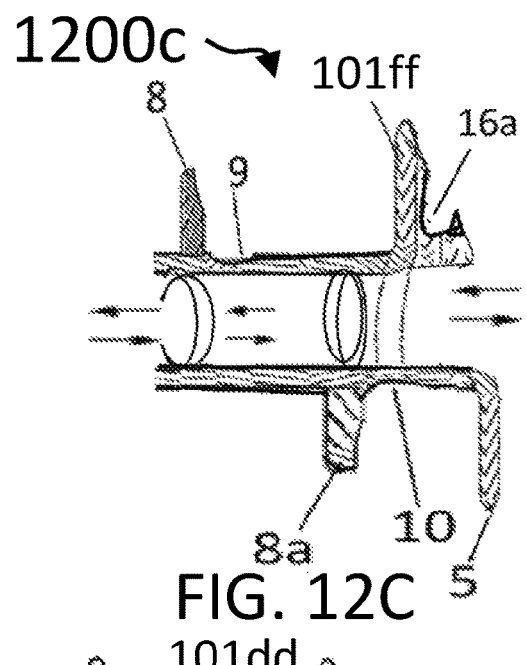
Figure 12A:
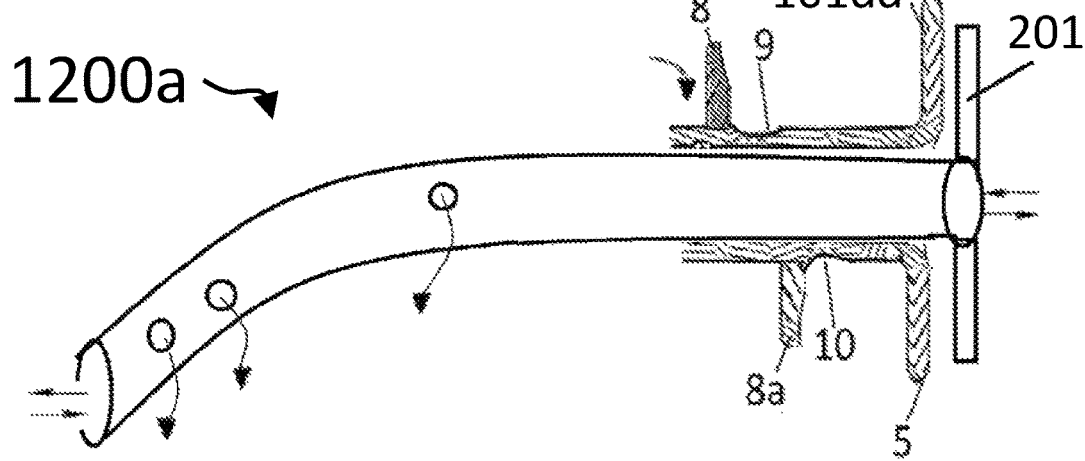

FIGS. 11A-B and 12A-C respectively show diagrams 1100a, 1100b, 1200a, 1200b, and 1200c including LJT mandibular protracting oral airway devices 101bb, 101cc, 101dd, 101ee, 101ff. In FIG. 11A, an LJT oral airway device 101bb is shown in a patient's mouth. For these FIGS. 11A-B and 12A-C, the explanation is generally the same as FIG. 9. Further, the ventral surface of the main body is short and adapts to the shape of the tongue. However, the dorsal surface has a smooth convex surface facing the concave surface of a patient's soft palate, all the way to its middle so as to prevent the tongue from moving back with the palate in semiconscious persons breathing spontaneously. LJT oral airway device 101cc generally provides a simple bite block to keep a patient's jaw protruded when a patient's jaw is loose and falls back to obstruct the airway. The LJT oral airway device 101cc is used to pull the jaw and maintain the airway in awake or spontaneous breathing patients. The upper lip flange 5 can be provided with a hook-like projection 16a (See FIG. 12C) that accommodates the nasal oxygen delivery catheter and holds it in position. FIG. 12A shows a device 201 that is the soft semi rigid oral airway that can be inserted through the device 101dd that acts as oral airway, and through which, the fiberoptic endoscopes can be inserted with ease and secretion can be suctioned out.

Figure 13:
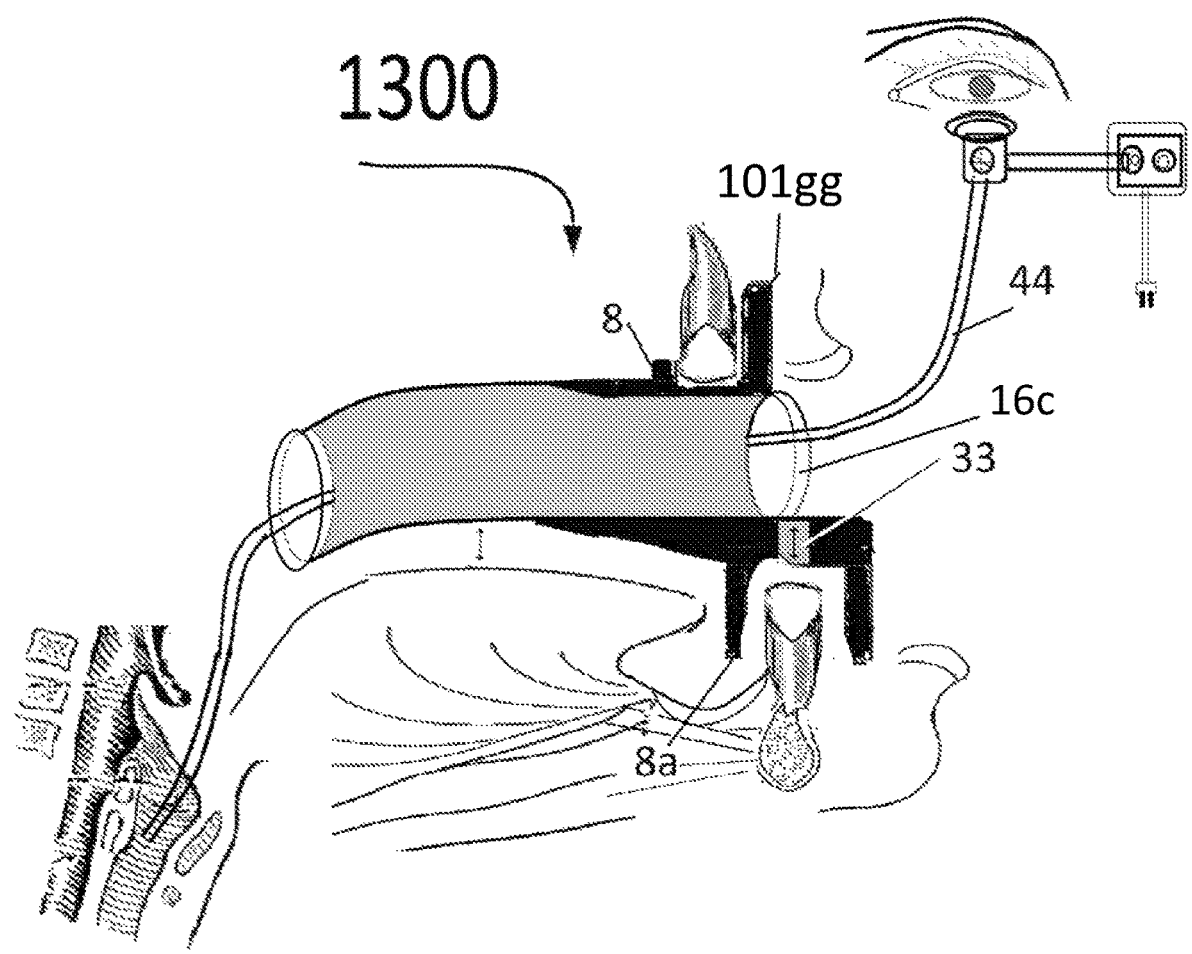
FIGS. 13 and 14 are diagrams showing LJT mandibular protracting oral airway devices, modified for use with diagnostic fiber optic scopes and for introducing endotracheal tubes, according to an embodiment.
Figure 14:
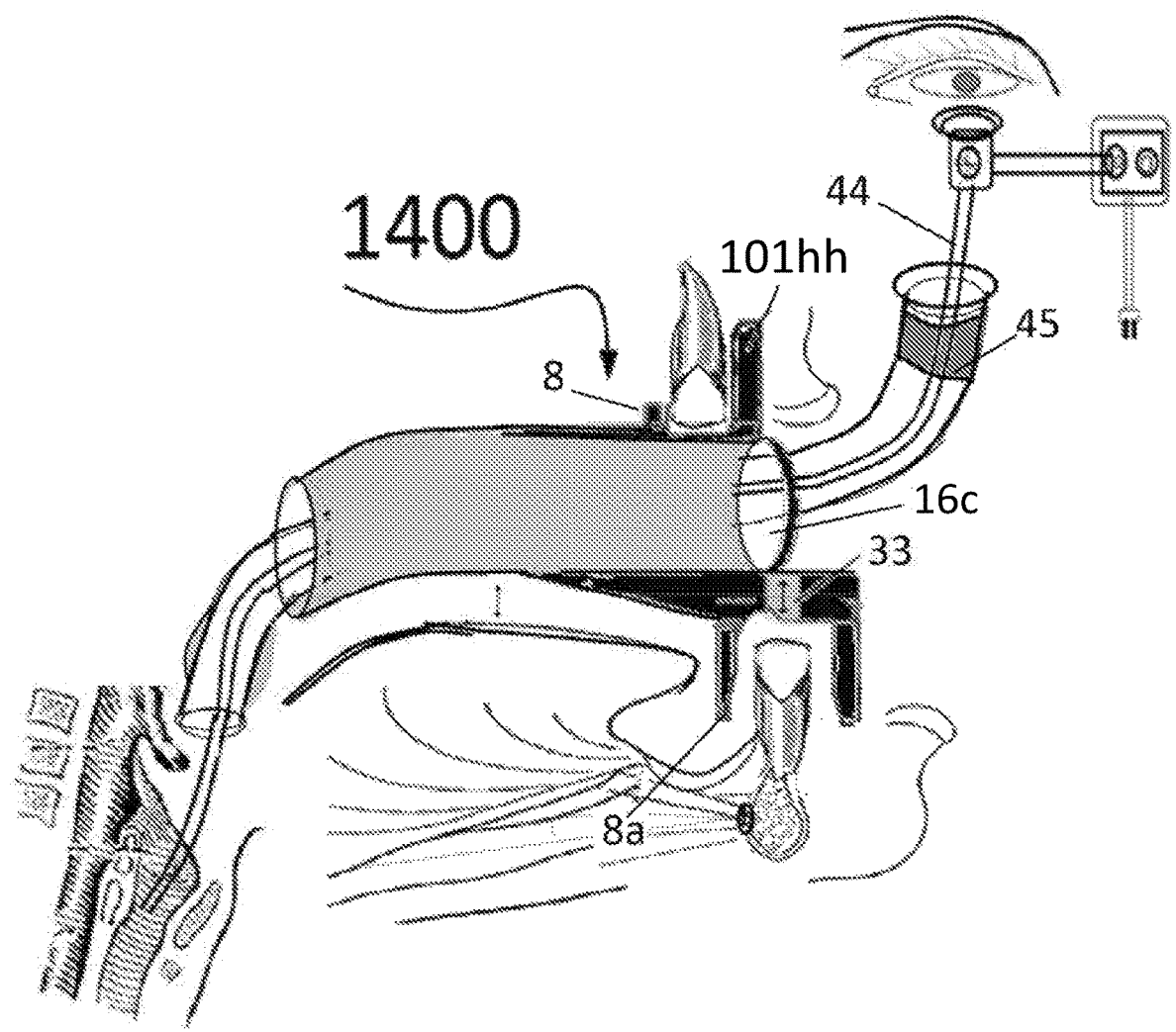

FIGS. 13 and 14 show diagrams 1300 and 1400 including modified endoscopic facilitating LJT mandibular protracting oral airway devices 101gg and 101hh in a patient's mouth. The devices 101gg and 101hh consist of: a short mouthpiece extending from the posterior end of the bite block with maxillary nub; a mandibular flange 8a to protract the jaw; and guidance tube openings 16c for the introduction of fiber optic scopes 44 or endotracheal tube 45 on a guide wire or on fiberoptic guidance. The oral guidance opening is placed higher on the mandibular flange 33 and is larger in diameter than in other oral airway devices, thus the guidance opening is closer to the hard palate than the tongue and is almost free floating so as to facilitate insertion of fiber optic device or endotracheal tube on guide scopes and at the same time protrudes the lower jaw pulling tongue with it to facilitate the insertion of the fiberoptic scopes or endotracheal tube placement. The devices 101gg and 101hh provide a new tool for management of difficult airways and it facilitates Awake Minimally Invasive Bronchoscopic Intubation (AMIBI) and other endoscopic procedures through the mouth. These modified LJT oral airway devices 101gg and 101hh provide a new approach to managing difficult airways in semiconscious or unconscious or tropicalizes patients. Medical applications and embodiments beyond use as an appliance to allow awake intubation and fiber optic procedures under mild sedation with or without the topicalization are possible. Other new rapid oral tracheal intubation guidance system (ROTIGS) intubation oral airways exist but do not have a mandibular protracting jaw thrusting embodiment. This feature can help pull the jaw and hold it during these procedures for easy passage of the devices. This mandibular protracting jaw thrusting maneuver, with placement of a scoping opening high above close to the soft palate, will open a patient's airway and facilitate these procedures. Further, the ventral bite block is placed farther below the external opening of the airway, thus preventing the ventral surface of the airway from coming in close contact with the dorsal surface of the tongue. Due to its mouthpiece and integral bite block, the LJT oral airway devices 101gg and 101hh keep the device centered and floating, thus permitting a midline bronchoscopic approach to the larynx and esophagus, as shown in the figures. The device also creates a space between the LJT oral airway device and the tongue. By creating a gag free approach to the larynx and esophagus, the LJT oral airway device facilitates safe, awake, guided trans-oral intubation for the occasional intermittent endoscopist. The device hardly rests on the tongue, and due to its short size of the C-part of the mouth piece and the way the opening is placed, there is a reduced opportunity for gag reflex or retching during the intubation and scope use. FIG. 13 shows the fiberoptic scope within an intubating airway according to embodiments disclosed herein and FIG. 14 shows the endotracheal tube placement using a fiberoptic scope using an intubating oral airway according to embodiments disclosed herein.

Figure 15:
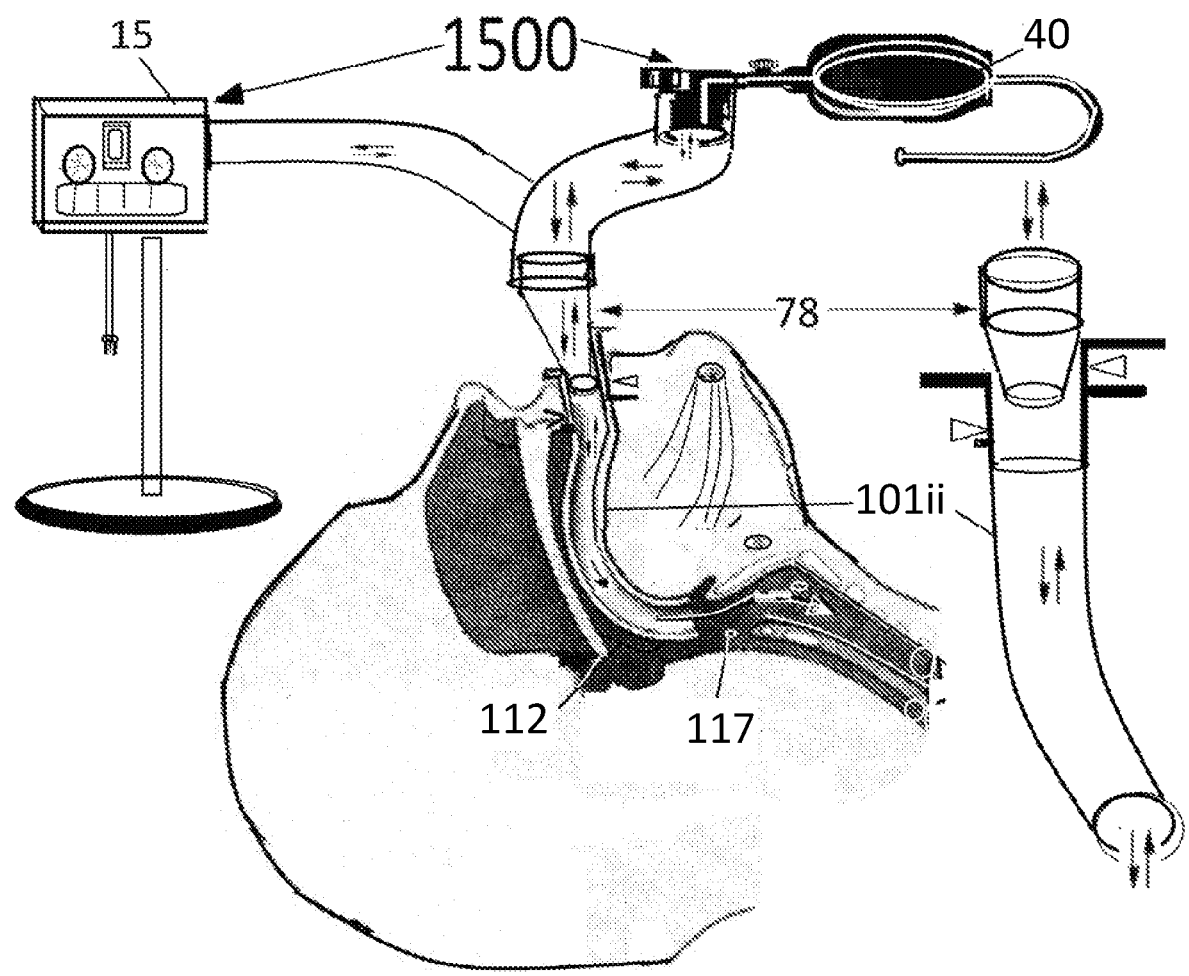
FIGS. 15 and 16 are diagrams showing LJT mandibular protracting oral airway devices, attached to a connector for ventilating with a mechanical ventilator or to ventilate using an Ambu bag, according to an embodiment.
Figure 16:
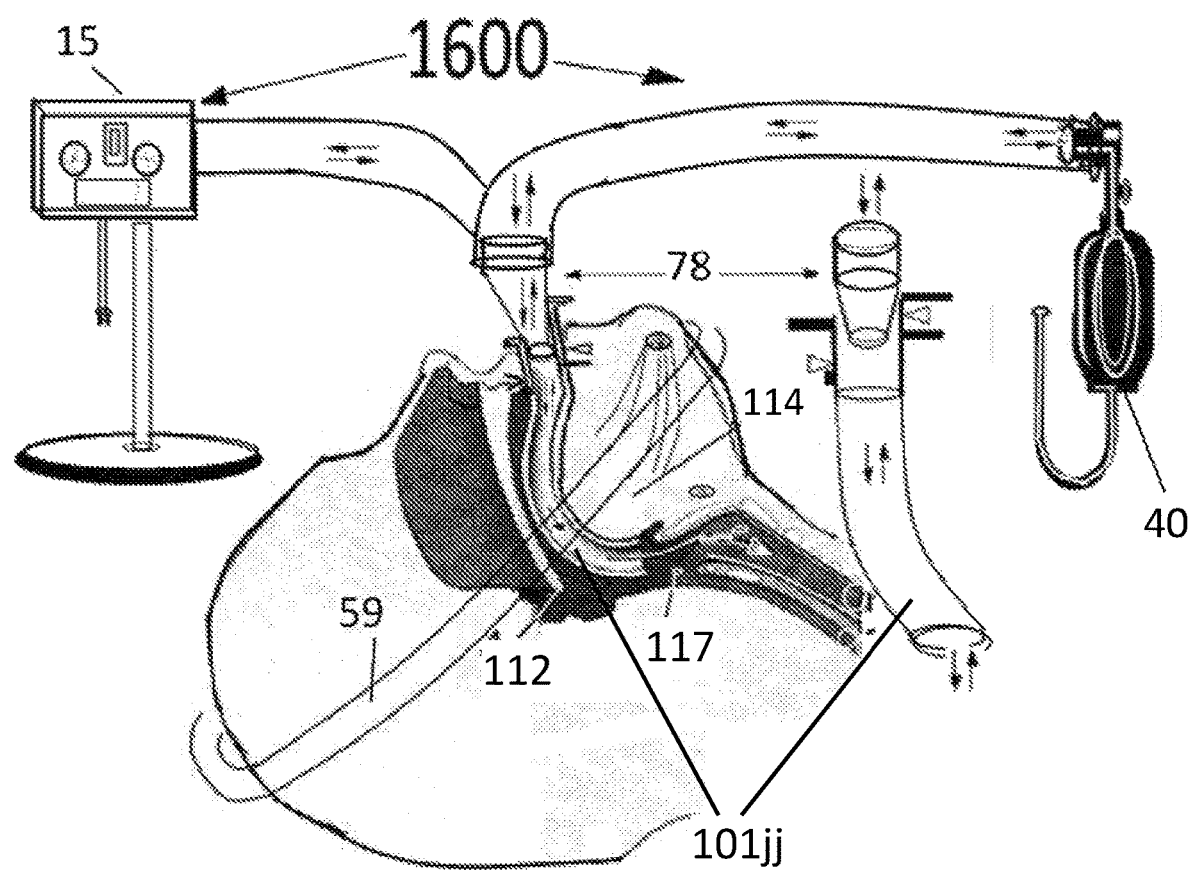

FIGS. 15 and 16 are diagrams 1500 and 1600 showing systems with embodiments of endoscopic facilitating LJT mandibular protracting oral airway devices 101ii and 101jj located in a patient's mouth. The devices 101ii and 101jj consists of a short mouthpiece, bite block with maxillary nub, mandibular flange to protract the jaw, and guidance tube openings for the introduction of fiber optic scopes as described above. The opening of the devices 101ii and 101jj is provided with a connector 78 which connects to mechanical ventilator 15 or Ambu bag 40 away from the patient's body, freeing the hands of the caregiver to attend to other patient needs. Further, as shown in the figures, devices 101*ii* and 101*jj* can be connected to Ambu bag operated by another person away from the face. A simple mandibular elastic strap 59 can used to pull and proximate the upper and lower jaws, hold the device 101*jj* in contact with the patient's lips, and thus prevent any air leak as air/oxygen is delivered through the tubing with these devices as shown in the figures. Diagrams 1500 and 1600 show the tongue 114, palate 112 and laryngeal inlet 117. Accordingly, LJT mandibular protracting oral airway device can include an extension connector 78 that accommodates a ventilating opening in the lip flange for a mechanical ventilator 15 or an Ambu bag 40.

It is noted that oral airway devices are widely used when a manual resuscitator set, commonly called an Ambu bag, is used. This type of bag valve mask is a hand-held device used to provide positive pressure to inflate the lungs of an unconscious person who is not breathing or who is breathing inadequately in order to keep them oxygenated and alive. The device is a normal part of a resuscitation kit for trained professionals, such as ambulance crew, emergency medical techs (EMT) and is also used in hospitals, and is an essential part of a crash cart. The device is used extensively in the operating room to ventilate (bagging) an anaesthetized patient minutes before a mechanical ventilator is attached with an oral airway in combination. The device is self-filling with air, although additional oxygen (02) can be added. In this invention, we are providing the simple connector to be attached to the proximal opening of this oral airway invention and Ambu bag. When the Ambu bag 40 is squeezed, the device forces air through into the patient's lungs; when the bag is released, it self-inflates from its other end, drawing in either ambient air or a low-pressure oxygen flow supplied by a regulated cylinder, while also allowing the patient's lungs to deflate to the ambient environment (not the bag) past the one-way valve. In order to be effective, a bag valve mask must deliver between 500 and 800 milliliters of air to an adult patient's lungs, by a caregiver squeezing the bag twelve times a minute. Most commonly, Ambu bags require two people, to maintain ventilation. However, various embodiments of LJT mandibular protracting oral airway devices, such as 101*ii* and 101*jj*, can facilitate only one person maintaining ventilation. A connector 78 to Ambu bag 40 and LJT mandibular protracting oral airway devices 101*ii* and 101*jj* is shown in FIGS. 15 and 16.

Figure 17:
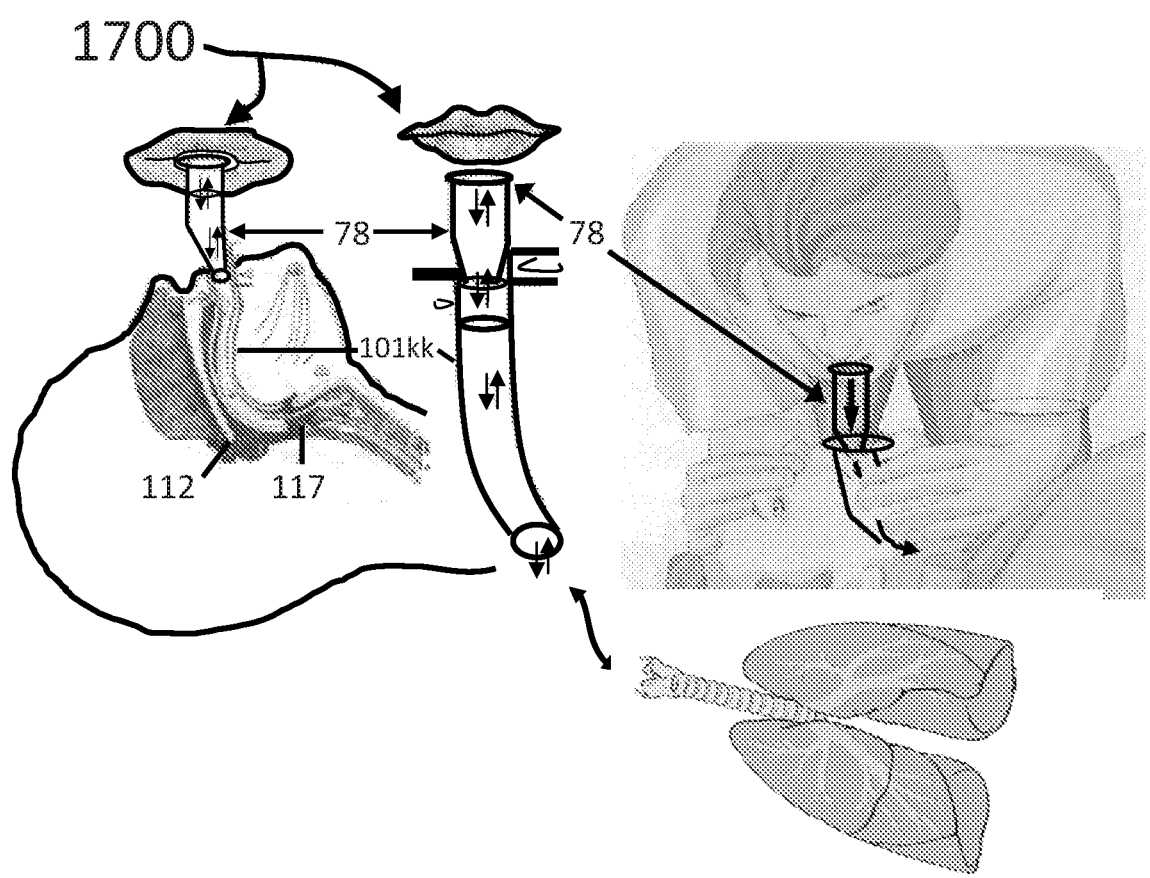
FIG. 17 is a diagram showing LJT mandibular protracting oral airway device used during CPR where air is delivered to the patient's lungs without touching the lips of the patient by the caregiver who is breathing air into lungs of the afflicted, according to an embodiment.

FIG. 17 and show diagram 1700 including LJT mandibular protracting oral airway device 101*kk* used during CPR for mouth-to-mouth breathing. The air is delivered to the lungs without touching the lips of the patient by the CPR care providers lip and oral cavity. An adapter 78 is provided to connect the air exit of the oral airway device 101*kk* and the mouth of the air delivering person without touching the patient's lips. Accordingly, LJT mandibular protracting oral airway device 101*kk* can simplify and aid persons conducting CPR. In some embodiments, vehicles can be equipped with such devices. In some embodiments, LJT mandibular protracting oral airway devices 101*kk* can be provided with a flat wood tongue depressor. Such a tongue depressor can make it convenient to insert an LJT oral airway device in an unconscious or semiconscious patient requiring ventilation.

Unlike a ventilator and endotracheal tubes, or other resuscitators, an oral airway device is designed to be inserted by opening of the mouth (or the nose in the case of a nasopharyngeal airway) to keep the airway open. It is often the case that the mouth and the nose may be covered with a mask, a breathing apparatus or other apparatus. For example, during anesthesia, masks or ventilator circuits may include equipment that is positioned over the nose and mouth of a patient. So that there is no inadvertent blocking, hitting or dislodging of the airway, or impairment of the function of the airway, the less that the airway extends past the nasal or mouth cavity, the less risk that is present. Devices of the prior art, accordingly, are generally not suitable for use, and would be difficult to couple such an airway without degrading the performance.

In some embodiments it is possible to monitor the rate of breathing and carbon dioxide content of the expired air, employing a loud noise maker when the breathing stops, which can endanger the life and provide an indicator as to whether or not the patient is breathing effectively. By monitoring breathing, the caregivers are able to adjust monitoring and adjust the airway as explained to reposition.

Embodiments of LJT oral airway devices can be latex-free and may be produced in a variety of sizes ranging from neonatal to large adult sizes and can be color-coded so as to indicate size upon quick visual observation.

An a LJT mandibular protracting oral airway device, in accordance with this disclosure and embodiments, can be adapted, configured, or manufactured to provide a desirable smell and/or taste with a coating. A flavoring material such as food, a natural flavor, or an artificial flavor including, but not limited to, bubble gum or a fruit, such as an orange, can be applied during or after the manufacture of the device. This can result in a desirable pleasing flavor being experienced when an LJT mandibular protracting oral airway device is utilized in the mouth in semiconscious, conscious and spontaneously breathing patients and have a pleasing effect after removal of the oral airway device. The scent or odor may be that of a food or other pleasant item with color coating for particular taste and smell.

By this disclosure one or more embodiments should be understood as relating to devices used as replacements to existing oral airway devices which do not incorporated lower jaw thrust when placed in a patient's mouth to retrain the tongue from obstructing the oral air passage.

In this application, various terms are used throughout the preceding discussion. Definitions and explanations of some of these terms are included for clarity:

The term "bite block" denotes the part of the oral airway device located between upper and lower jaws between the incisor teeth.

The term "C curve" of the oral airway denotes the part of the airway located between the palate and the tongue when inserted.

The term "mandibular" denotes the part of the extension on the ventral surface of the oral airway bite block that holds the protracted jaw in position and is positioned behind the mandibular incisor.

The term "ventilation" is a volume of gas entering and exiting the lungs. Gas exchange at the level of the alveolus, alveolar ventilation, determines the arterial tension of carbon dioxide.

The term "lip flange" denotes the part of an oral airway device located in front of the bite block, that holds the oral airway device in position and prevent it from being dislocated into a patient's oral cavity. The center of the lip flange can contain a hole to allow ventilating and side holes for suctioning.

The term "lower jaw" denotes the mandible with incisor teeth, and the "upper jaw" denotes maxilla with incisor teeth.

The term "general anesthesia" is a type of sedation that uses several medications to render a patient unconscious and unable to move. It makes a patient sleep through any number of surgical and non-surgical procedures. General anesthesia also paralyzes a patient. This paralysis affects most of the muscles of the body, including the lungs, but does not stop the heart from working.

The term "unconscious" is a state like sleep because of an injury or illness, and may not permit use of one's senses, may not permit breathing, or may involve breathing with difficulty The term "semiconscious" is partially awake or half aware. A person who is emerging from anesthesia or sedation, or woken up from a dream, but easily falls back asleep is an example of someone who is semiconscious. An example of semiconscious is the state of a very sick patient who is drifting in and out of awareness.

The term "sleep" is defined as a naturally recurring state of mind and body characterized by altered consciousness, relatively inhibited sensory activity, inhibition of nearly all voluntary muscles, and reduced interactions with surroundings The term "obstructive sleep apnea" refers the occurrence of daytime sleepiness, loud snoring, breathing interruptions, or awakenings due to gasping or choking in the presence of obstructive respiratory events (apneas, hypopneas or respiratory effort resulting in arousals) many times per hour of sleep.

The term "apnea" refers to suspension of external breathing. Apnea causes airflow cessation in the upper airway of a subject, hence to the lungs and low blood oxygen levels with increased $CO_2$.

The term "snoring" refers to with a rough hoarse noise due to vibration of respiratory structures, mainly soft palate muscle due to breathing during sleep.

The term "obesity" or "being obese" used herein refers to a condition of excess body fat that may have an adverse effect on health, leading to reduced life expectancy and/or increased health problems. People having a body mass index (BMI) greater than 30 kg/m² are usually considered obese.

Various embodiments of systems, devices, and methods have been described herein. These embodiments are given only by way of example and are not intended to limit the scope of the claimed subject matter. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed subject matter.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

EXAMPLES

The following examples are also intended as illustrative and in no manner limiting as to the scope and breadth of the foregoing description and the accompanying drawings to those of skill in the art.

I. A lower jaw thrusting (LJT) mandibular protracting oral airway device, comprising:
  a semi-rigid tubular member oral mouth piece;
  a bite block coupled to the semi-rigid tubular member oral mouth piece;
  wherein the semi-rigid tubular member oral mouth piece contains a lumen extending from a back portion of the bite block to an end for insertion to the root of a patient's tongue,
  wherein the bite block includes a dorsal surface with a maxillary flange having a maxilla movement blocker acting as a fulcrum;
  wherein the bite block includes a mandibular flange to hold the lower mandibular jaw in position, located anterior to the maxillary flange on a ventral surface of the bite block;
  wherein a front flange and a rear flange are connected with the bite block;
  wherein a front part of the bite block is provided with an upper lip flange and a lower lip flange which are provided to overlie a patient's lips to hold the oral airway device fixed without backward movement or accidental swallowing;
  a resilient, annular tooth-engaging member for mandible positioning between the front flange and the mandibular flange for positioning and maintaining a protracted mandibular position with an incisor teeth notch on the bite block of the ventral surface;
  wherein a patient's upper teeth are in a first position and are adapted to engage a patient's lower teeth and position and maintain a patient's mandible thrust forward in a protracted position relative to the first position of the maxillary teeth, with maxillary teeth acting as fulcrum;
  a tongue positioning means for positioning and maintaining the patient's tongue in a forward position, preventing its movement backwards postero-inferiorly towards the patient's oropharynx airway, hence the tongue does not obstruct the patient's oro-naso-laryngo-pharynx airway comprising a semi rigid and curved rearward extension on the rigid tubular or nontubular member from the bite block, which is adapted to engage the top of the patient's tongue.

II. The LJT mandibular protracting oral airway device of Example I, wherein the bite block between the front flange and rear flange of tooth-engaging member comprises a maxillary movement blocker behind the front upper lip flange and a mandibular block behind the lower lip flange a distance in front of the maxillary flange, wherein the lip flange keeps a proximal end of the oral airway device from entering the patient's mouth; wherein a body is sized such that the distal end of the body is disposed within the pharynx above and in front of the epiglottis; wherein a channel is included that forms an airway between the proximal end and distal end.

III. The LJT mandibular protracting oral airway device of Example I, wherein a rigid or malleable curved rearward oral extension from the back of the bite block is flat, tubular, or open on both side with a central rigid rib in transverse cross section and extends rearwardly from the rigid tubular bite block and curves downwardly relative thereto to form a gently C-shaped flat tongue retractor portion which engages a patient's tongue so as to hold it forward and not allow moving backwards with jaw thrust.

IV. The LJT mandibular protracting oral airway device of Example I, wherein the ventral surface is provided with an oval or rectangular plate wide enough from side to side which will give better support to the tongue lateral to the inserted LJT oral airway, thus increasing the side to side dimension of the airway opening provide enough support for the large tongue that is needed to open the patient's airway to ventilate.

V. The LJT mandibular protracting oral airway device of claim 4, further including a horizontal bar on the ventral plate to prevent the sliding back of the flaccid slimy tongue under the oral airway.

VI. The LJT mandibular protracting oral airway device of Example I, further including an oval elevation in the middle of the distal end ventral plate of the oral airway which will prevent the root of the tongue falling back on the epiglottis and posterior pharyngeal wall, thus keep the nasopharynx, oropharynx and laryngopharynx open for unobstructed airflow from lips, mouth, oropharynx and laryngeal passage then to tracheobronchial passage to lung alveoli.

VII. The LJT mandibular protracting oral airway device of Example I, further including holes on the dorsal plate to allow the air and oxygen to enter the naso-pharynx if the oropharynx is obstructed due to any number of reasons and allowing easy suctioning of the secretions and regurgitated material.

VIII. The LJT mandibular protracting oral airway device of Example I, wherein an oval or rectangular opening is provided in the center of a bite portion of the bite block, disposed between the mandibular and maxillary flanges placed at different distances from the front lip flanges, and allows bite block and the oval shaped opening through the bite portion functions as an intubation guide to facilitate insertion of an endotracheal tube, endoscopes and related medical instruments, such as a fiber-optic intubating stylet with an attached endotracheal tube or insert a cannula to deliver supplementary oxygen or pass a nasogastric tube.

IX. The LJT mandibular protracting oral airway device of Example I, wherein said rigid tubular member and said access port are generally oval or rectangular or oval shaped in transverse cross section.

X. The LJT mandibular protracting oral airway device of Example I, wherein the lip flanges are provided with holes to deliver nasal oxygen with a hook on the upper or lower lip flange.

XI. The LJT mandibular protracting oral airway device of Example I, wherein the device is made up of synthetic or semisynthetic material which is non-reacting and hypoallergic to the user, and which are color coded for easy identification of the size of oral airway to be selected.

XII. The LJT mandibular protracting oral airway device of Example I, wherein the device is made up of transparent, to enable observation of the oral cavity of the subject during the endoscopic procedure and the lip flange has an oval extension with holes to secure the airway with a strap that binds the device around the head or ears.

XIII. The LJT mandibular protracting oral airway device of Example I, wherein the device is made up of the bite block wherein said oral breath directing element is designed to retract and extend in order to bring said bite block closer and farther, correspondingly, from said oral-nasal cannula, thereby accommodating the facial dimensions of the subject.

XIV. The LJT mandibular protracting oral airway device of Example I, wherein the rear mandibular flange can be pulled forward to enhance the thrusting of the lower jaw much more depending upon the mandibular size and physical movement of the mandible of the individual and mobility of the lower jaw.

XV. The LJT mandibular protracting oral airway device of Example I, further including a tubing hole which engages a Leuer lock syringe, connected by tubing to the tongue retractor part through which the fluids can be delivered to the tongue and oro-naso-laryngo-pharynx in patient to keep the oral mucosa wet during prolonged intubation; wherein this tubing hole also can be used to deliver therapeutic agents for any afflictions of the oral cavity or deliver to the fluids, nutrition therapeutic agents to the stomach through the NG tube in the intubated patients and allow breathing during endoscopy use through the central large airway opening.

XVI. The LJT mandibular protracting oral airway device of Example I, further including an injection/delivery inlet positioned on the lip flange, which accommodates a luer lock or three way stop-cock to which delivery to the luer lock syringe with or without the tubing are attached, to deliver liquids to keep the oral cavity moist and also deliver therapeutic agents, to insert NG tube to intubated patients, and also can act as suction catheter inlet or to attach nasal oxygen delivery system deliver supplemental oxygen.

XVII. The LJT mandibular protracting oral airway device of Example I, further including a short buccal bite block to be used with the endoscopic bite wherein at least part of said upper and lower outer surfaces of said central channel comprise a material softer than that of said upper and lower inner surfaces.

XVIII. The LJT mandibular protracting oral airway device of Example I, further including a breathing air collection tube is disposed upper wall of said central channel, such that it enters said breath sampling channel in a direction facing a stream of exhaled oral breath.

XIX. The LJT mandibular protracting oral airway device of Example I, wherein at least one of said upper and lower outer surfaces of the bite block has a generally flattened portion with curved notch for edges of the upper and lower incisor teeth curved to accommodate a human jaw.

XX. The LJT mandibular protracting oral airway device of Example I, wherein the mandibular flange is attached to the bite block of any existing oral airways such as Guedel, Berman, Miller, Ovassapian and such in the market modified by to fit the specific needs to convert into a mandibular protracting LJT oral airway device.

XXI. The LJT mandibular protracting oral airway device of Example I, further including an extension attachment that accommodates the ventilating opening in the lip flange to which the mechanical ventilator or Ambu bag with extension is attached which will free the hands of the caregiver; wherein the Ambu bag is attached to a flexible extension tubing that can be managed by another caregiver.

XXII. The LJT mandibular protracting oral airway device of Example I, further including long tubing that attaches to the ventilatory end of the oral airway and the distal end is used by another person to inflate the lungs during CPR without coming in contact with the mouth of the unconscious patient.

XXIII The LJT mandibular protracting oral airway device of Example I, wherein the device is modified so as to accommodate fiber optic examination or intubation with ease by making the tongue piece short, and float on the mouth, and allow insertion of these devices with ease.

XXIV. The LJT mandibular protracting oral airway device of Example I, wherein the device is modified so as to accommodate a luer lock syringe outlet provided on the lower lip flange to deliver therapeutic agents under the tongue to treat obstructive sleep apnea and other afflictions of the oral cavity.

XXV. The LJT oral airway use facilitates ventilation due to lower jaw thrust opening the airway no matter how difficult it is to intubate based on various parameters of preoperative airway assessment (including Mallapati's) and allows anesthesiologist time to evaluate options for successful intubation when faced with difficult intubation and ventilation situations after induction of anesthesia. Thus, preventing any undesirable results due to difficulty in establishing effective ventilation. Difficult airway management is one of the principal challenges faced by anesthesiologists in their practice resulting in inadequate ventilation and esophageal intubation that are the principal factors responsible for morbidly and mortality, including possible brain damage.

What is claimed is:

1. A lower jaw thrusting (LJT) mandibular protracting oral airway device, comprising:
    an elongate member having a distal end and a proximal end defining an air passageway channel therebetween, the elongate member sized for insertion in a patient's mouth such that the distal end is able to be disposed adjacent the patient's tongue root while the proximal end remains disposed outside the patient mouth, the elongate member comprising:
    a lip flange located at the proximal end of the elongate member having an outwardly projecting surface configured to overlie lips of the patient;
    a curved main body extending to the distal end of the elongate member, that provides downward and inferior tongue pressure resistive to backward tongue movement; and
    a bite block disposed between the lip flange and the curved main body, including an upper dorsal surface having a first bite portion for maxillary incisor teeth engagement and a lower ventral surface having a second bite portion for mandibular incisor teeth engagement, the bite block including a mandibular flange projecting downwardly from lower ventral surface, located distal to the second bite portion for mandibular incisor teeth engagement and proximal to the first bite portion for maxillary incisor teeth engagement,
    wherein the lip flange is comprised of an upper lip flange and a lower lip flange, and wherein the mandibular flange is located 0.25 to 1 inch proximal from the upper lip flange as to extend the mandibular jaw.

2. The LJT mandibular protracting oral airway device of claim 1, wherein the upper dorsal surface provides a depression at the first bite portion and the lower ventral surface provides a depression at the second bite portion.

3. The LJT mandibular protracting oral airway device of claim 1, wherein the bite block includes a maxillary flange upwardly projecting from the upper dorsal surface, the maxillary flange located distal to the mandibular flange along the elongate member.

4. The LJT mandibular protracting oral airway device of claim 1, wherein the air passageway channel of the elongate member is generally substantially arcuate and tubular in shape.

5. The LJT mandibular protracting oral airway device of claim 1, wherein the air passageway channel of the elongate member is C-shaped and defines openings along the curved main body.

6. The LJT mandibular protracting oral airway device of claim 1, wherein the upper dorsal surface and lower ventral surface of the bite block comprise resilient material.

7. The LJT mandibular protracting oral airway device of claim 1, wherein the curved main body includes a round nub near the distal end of the elongate body that is configured to engage the patient's tongue root in front of the epiglottis thereby restricting distal backward movement of the tongue root.

8. The LJT mandibular protracting oral airway device of claim 1, wherein the curved main body includes a pair of lateral extensions extending along the sides of the ventral surface that restrict tongue movement.

9. The LJT mandibular protracting oral airway device of claim 1, wherein the curved main body includes a dorsolateral plate containing a plurality of holes.

10. The LJT mandibular protracting oral airway device of claim 1, wherein the bite block contains a second mandibular flange projecting outwardly from the lower ventral surface, the mandibular flange and the second mandibular flange forming a pocket surrounding the second portion for mandibular incisor teeth engagement.

11. The LJT mandibular protracting oral airway device of claim 1, wherein the bite block contains a pair of maxillary flanges outwardly projecting from the upper dorsal surface, the pair of maxillary flanges forming a pocket surrounding the first portion for maxillary incisor teeth engagement.

12. The mandibular protracting oral airway device of claim 1, further including an extension attachment that accommodates a ventilating opening in the lip flange surrounded by an external opening in the oral airway device for connecting to a mechanical ventilator or an Ambu bag.

13. The LJT mandibular protracting oral airway device of claim 1, wherein the air passageway channel is generally oval or rectangular in cross section.

14. The LJT mandibular protracting oral airway device of claim 1, wherein the elongate member is semi-rigid distal to the lip flange and resistant to collapse.

15. The LJT mandibular protracting oral airway device of claim 1, wherein the mandibular flange permits proximally forward pulling that enhances thrusting of the lower jaw, along with the root of the tongue.

16. The LJT mandibular protracting oral airway device of claim 1, wherein the lip flange includes at least one hole adapted for nasal oxygen delivery or delivery tubing tetheted to a hook.

17. The LJT mandibular protracting oral airway device of claim 1, wherein the curved main body has a short length, large diameter configuration that accommodates fiber optic examination or intubation.

18. The LJT mandibular protracting oral airway device of claim 1, wherein the lip flange incorporates liquid transfer tubing of different lengths running above or below the bite block, that can be attached to a three-way stopcock outside the patient's mouth, to transport therapeutic agents or mouth rinsing fluids under or above the patient's tongue.

19. A lower jaw thrusting (LJT) mandibular protracting oral airway device, comprising:
- an elongate member having a distal end and a proximal end defining an air passageway channel therebetween, the elongate member sized for insertion in a patient's mouth such that the distal end is disposed adjacent the patient's tongue root while the proximal end remains disposed outside the patient mouth, the elongate member comprising:
- a lip flange located at the proximal end of the elongate member, the lip flange comprising an upper lip flange and a lower lip flange, each comprising a vertically-disposed member generally projecting outwardly relative to a central opening of the air passageway channel, wherein the upper lip flange has a first distal surface that is generally vertically-disposed for proximal placement relative to an upper lip of the patient's mouth, and wherein the lower lip flange has a second distal surface that is generally vertically disposed for proximal placement relative to a lower lip of the patient's mouth, wherein the first distal surface of the upper lip flange is located distal to the second distal surface of the lower lip flange;
- a curved main body extending to the distal end of the elongate member, that provides downward and inferior tongue pressure resistive to backward tongue movement; and
- a bite block disposed between the lip flange and the curved main body, including an upper dorsal surface for maxillary incisor teeth engagement and a lower ventral surface for mandibular incisor teeth engagement, the bite block including a mandibular flange projecting downwardly from lower ventral surface, the mandibular flange having a surface located proximal to the first distal surface of the upper lip flange, wherein the lip flange is comprised of an upper lip flange and a lower lip flange and wherein the mandibular flange is located 0.25 to 1 inch proximal from the upper lip flange as to extend the mandibular jaw.

* * * * *